United States Patent [19]

Banno et al.

[11] Patent Number: 4,824,840
[45] Date of Patent: Apr. 25, 1989

[54] CARBOSTYRIL DERIVATIVES AND PHARMACEUTICAL PREPARATIONS CONTAINING SAME

[75] Inventors: Kazuo Banno; Takafumi Fujioka; Yasuo Oshiro; Kazuyuki Nakagawa, all of Tokushima, Japan

[73] Assignee: Otsuka Pharmaceutical Co., Ltd., Japan

[21] Appl. No.: 25,193

[22] Filed: Mar. 12, 1987

Related U.S. Application Data

[62] Division of Ser. No. 24,602, Mar. 28, 1979, Pat. No. 4,734,416.

[30] Foreign Application Priority Data

Mar. 30, 1978 [JP] Japan .................... 53-37783

[51] Int. Cl.$^4$ .................... A61K 31/495; C07D 403/02
[52] U.S. Cl. ................... 514/218; 544/363; 546/157; 546/158
[58] Field of Search .................... 540/575; 514/218

[56] References Cited

U.S. PATENT DOCUMENTS

| 3,362,956 | 1/1968 | Archer | 544/295 |
|---|---|---|---|
| 3,511,841 | 5/1970 | Archer | 544/295 |
| 3,654,277 | 4/1972 | Winter et al. | 544/399 |
| 3,703,522 | 11/1972 | Plostnicks | 546/156 |
| 3,706,749 | 12/1972 | Plostnicks | 546/156 |
| 3,810,896 | 5/1974 | Witte et al. | 544/361 |
| 3,810,898 | 5/1974 | Witte et al. | 544/361 |
| 3,919,226 | 11/1975 | Thiel et al. | 544/277 |
| 3,932,411 | 1/1976 | Braun et al. | 544/399 |
| 3,936,459 | 2/1976 | Kato et al. | 546/186 |
| 3,940,397 | 2/1976 | Wade et al. | 544/362 |
| 3,981,864 | 9/1976 | Tanaka et al. | 546/18 |
| 3,983,121 | 9/1976 | Murthi et al. | 544/363 |

(List continued on next page.)

FOREIGN PATENT DOCUMENTS

| 801037 | 12/1968 | Canada . |
| 0005828 | 3/1981 | European Pat. Off. . |
| 1932384 | 1/1969 | Fed. Rep. of Germany . |
| 2354145 | 5/1974 | Fed. Rep. of Germany . |
| 2631317 | 2/1977 | Fed. Rep. of Germany . |
| 2706752 | 9/1977 | Fed. Rep. of Germany . |

(List continued on next page.)

OTHER PUBLICATIONS

"Chemical Abstracts", vol. 95, 1981, cols. 95:25121q and 95:25127w.

(List continued on next page.)

*Primary Examiner*—Glennon H. Hollrah
*Assistant Examiner*—James H. Turnipseed

*Attorney, Agent, or Firm*—Finnegan, Henderson, Farabow, Garrett & Dunner

[57] ABSTRACT

Carbostyril derivatives having antihistaminic action and central nervous controlling action are useful as antihistaminic agents or central nervous controlling agents. The derivatives are represented by the general formula,

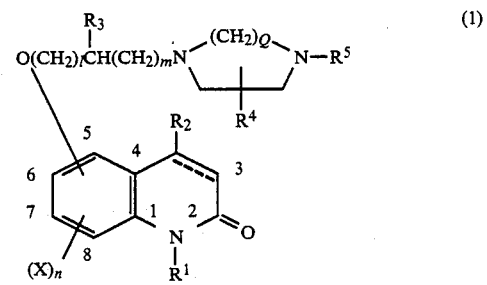

wherein $R^1$ is a hydrogen atom, an alkyl group having 1 to 6 carbon atoms, an alkenyl group having 2 to 4 carbon atoms, an alkynyl group having 2 to 4 carbon atoms or a phenylalkyl group, an alkylene group containing 1 to 4 carbon atoms; $R^2$ is a hydrogen atom, an alkyl group having 1 to 4 carbon atoms or a phenyl group; $R^3$ is a hydrogen atom, a hydroxy group, an alkyl group having 1 to 4 carbon atoms, an alkanoyloxy group having 1 to 4 carbon atoms or a 3,4,5-trimethoxybenzoyloxy group; $R^4$ is a hydrogen atom or an alkyl group having 1 to 4 carbon atoms; $R^5$ is a cycloalkyl group having 3 to 8 carbon atoms, a phenyl group (which may have 1 to 3 substituted groups selected from the group consisting of halogen atoms, alkyl groups having 1 to 4 carbon atoms and alkoxy groups having 1 to 4 carbon atoms), an alkyl group having 1 to 4 carbon atoms (having one substituted group such as a hydroxy group, a phenyl group or an alkanoyloxy group having 1 to 4 carbon atoms), an alkanoyl group having 1 to 4 carbon atoms or benzoyl group; X is a halogen atom; n is 0, or an integer of 1 or 2; Q is an integer of 2 or 3, l and m are respectively an integer of 0 to 1–6, but the sum of l and m should not exceed 6; the carbon-carbon bond at the 3- and 4-positions in the carbostyril skeleton is a single or double bond and; the substituted position of the side chain of

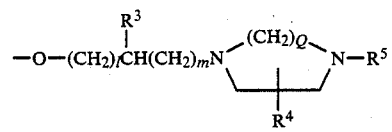

is any one of the 4-, 5-, 6-, 7- or 8-positions.

15 Claims, No Drawings

U.S. PATENT DOCUMENTS

| | | | |
|---|---|---|---|
| 3,994,900 | 11/1976 | Krapcho et al. | 260/286 |
| 4,026,895 | 5/1977 | Tanaka et al. | 544/368 |
| 4,032,528 | 6/1977 | Hardtmann | 546/156 |
| 4,060,526 | 11/1977 | Shetty | 544/60 |
| 4,110,449 | 8/1978 | Wade et al. | 544/368 |
| 4,117,228 | 9/1978 | Tanaka et al. | 544/377 |
| 4,147,869 | 4/1979 | Nakagawa et al. | 544/363 |
| 4,166,116 | 8/1979 | Coutts et al. | 544/377 |
| 4,210,753 | 7/1980 | Tominaga et al. | 544/128 |
| 4,234,584 | 11/1980 | Lattrell et al. | 424/250 |
| 4,234,585 | 11/1980 | Winter et al. | 424/250 |
| 4,256,890 | 3/1981 | Nakagawa et al. | 546/158 |

FOREIGN PATENT DOCUMENTS

| | | |
|---|---|---|
| 1561911 | 2/1969 | France . |
| 2179715 | 12/1976 | France . |
| 2344538 | 7/1980 | France . |
| 1075156 | 7/1967 | United Kingdom . |
| 1111785 | 5/1968 | United Kingdom . |
| 1212174 | 11/1970 | United Kingdom . |
| 1451900 | 10/1976 | United Kingdom . |
| 1572920 | 8/1980 | United Kingdom . |

OTHER PUBLICATIONS

Principles of Medicinal Chemistry, (Foye Ed. 1974), pp. 454–456.

Cutting's Handbook of Pharmacology, (1972), pp. 312–325.

Petigara et al., J. Med. Chem., 11 (2), 332–336.

Zejc et al., Pol. J. Pharmacol. Pharm., 1976, 28, 369–374.

Chem. Abstract, 112035q.

Fielden et al., Journal of Medicinal Chemistry, 1973, vol. 16, No. 10, 1124–1128.

Pp. 47–53, 153–197 and 590–623 of The Pharmacological Basis of Therapeutics, (Goodman and Gilman Ed., 1975).

Kazuyuki Nakagawa et al.; Derivatives of 3,4-Dihydrocarbostyril As $\beta$-Adrenergic Blocking Agents; Journal of Medicinal Chemistry, 1974, vol. 17, No. 5, pp. 529–533.

CARBOSTYRIL DERIVATIVES AND PHARMACEUTICAL PREPARATIONS CONTAINING SAME

This is a divisional application of Ser. No. 06/024,602 filed Mar. 28, 1979, now U.S. Pat. No. 4,734,416.

The present invention relates to novel carbostyril derivatives. More particularly, the present invention relates to novel carbostyril derivatives and acid addition salts thereof represented by the general formula (1) as follows:

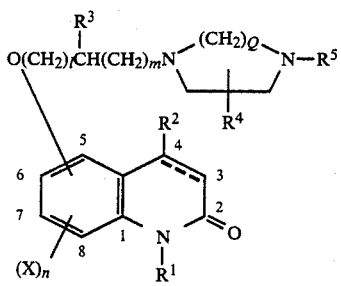

wherein $R^1$ is a hydrogen atom, an alkyl group having 1 to 6 carbon atoms, an alkenyl group having 2 to 4 carbon atoms, an alkynyl group having 2 to 4 carbon atoms or a phenyl alkyl group containing an alkylene group having 1 to 4 carbon atoms; $R^2$ is a hydrogen atom, an alkyl group having 1 to 4 carbon atoms or a phenyl group; $R^3$ is a hydrogen atom, a hydroxy group, an alkyl group having 1 to 4 carbon atoms, an alkanoyloxy group having 1 to 4 carbon atoms or a 3,4,5-trimethoxybenzoyloxy group; $R^4$ is a hydrogen atom or an alkyl group having 1 to 4 carbon atoms; $R^5$ is a cycloalkyl group having 3 to 8 carbon atoms, a phenyl group (which may have 1 to 3 substituted groups selected from the group consisting of halogen atoms, alkyl groups having 1 to 4 carbon atoms and alkoxy groups having 1 to 4 carbon atoms), an alkyl group having 1 to 4 carbon atoms (having one substituted group such as a hydroxy group, a phenyl group or an alkanoyloxy group having 1 to 4 carbon atoms), an alkanoyl group having 1 to 4 carbon atoms or a benzoyl group; X is a halogen atom; n is 0 or an integer of 1 or 2; Q is an integer of 2 or 3; l and m are respectively 0 or an integer of 1 to 6, but the sum of l an m should not exceed 6; the carbon-carbon bond at the 3- and 4-positions in the carbostyril skeleton is a single or double bond; and the substituted position of the side chain of

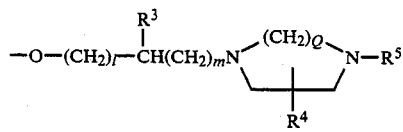

is any one of the 4-, 5-, 6-, 7- or 8-positions.

The compounds of the present invention have an antihistaminic effect and a central nervous controlling effect and are useful as antihistamininic agents and central nervous controlling agents.

As described generally in various articles of medical and pharmaceutical publications, for example, Goodman, Gilman: "Pharmacology" (the first volume); "YAKUBUTSU CHIRYL NO KISO TO RINSHO" (Fundamental and Clinic of Pharmacotherapy), pages 781–835 [published from Hirokawa Shoten Co., (1974)]; "SHIN-OYO YAKURIGAKU" (New applied pharmacology) by Hisashi Uno, pages 307 to 319 [published from Nagai Shoten Co., (1970)]; "SHIN'YAKU TO RINSHO" (Journal of New Remedies & Clinic), Vol. 20, No. 11, pages 129-133 (1971); and "KISO TO RINSHO" (Laboratory and Clinic), Vol. 10, No. 10, pages 17–27 (1976), an antihistaminic agent does not inhibit the isolation of a combined type histamine produced by the antigen-antibody reaction of allergy, but inhibits the combination (a competitive antagonism) of an active type histamine with a histamine-acceptor to show an antihistaminic effect. Therefore, the antihistaminic agents according to the present invention are effective as treating agents and prophylactic agents for various allergic diseases and symptoms caused by the combination of histamine and histamine-acceptor, such as sneezing, snuffles, prickling at eyes, nose and throat, allergic symptoms of respiratory tract, hay fever, pollinosis, acute uriticaria (itching, edema, flare and the like), vascular edema, pruritus, atpic dermatitis, insect bite, contact-type dermatitis such as "urushi kabure", ulticaria at serum disease, edemic disorder, allergic rhinitis, allergic cunjunctivitis or corneitis. Furthermore, antihistamininic agent can also be used as a supplemental agent for curing general anaphylaxis in which autocoids other than histamine may perform an important role. Additionally, an antihistaminic agent can also be used as a diagnostic reagent for measuring gastric acidity.

Some pharmaceutical literature reports that 5-(3-tert-butylamino-2-hydroxy)propoxy-3,4-dihydrocarbostyril hydrochloride of the following formula,

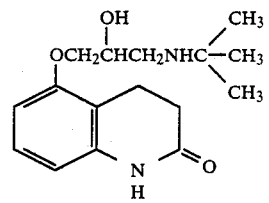

has an antihistaminic effect to a certain extent $(pA_2=5.02)$, [OYO KAKURI (Applied Pharmacology), vol. 11, No. 4, pages 437–462 (1976)]. Furthermore, German Patent Application (Laid-open) No. 2302027 (corresponding to U.S. Pat. No. 3,910,924) discloses (2-hydroxy-3-amino)-propoxy-(3,4-dihydro)-carbostyril derivatives having $\beta$-adrenergic blocking action.

However, it has not previously been known that novel compounds of the present invention have antihistaminic effects and central nervous controlling effects.

Central nervous controlling activities of compounds according to the present invention are characterized in that they have strong controlling activities for the fighting motion of a mouse isolated from others for a long period of time. Thus as compared with Diazepam, which have been known as a compound having such strong activities, compounds of the present invention have outstanding controlling effect for the fighting motion of a mouse; therefore, the present compounds are quite useful particularly as sedatives, antianxiety drugs, and anti-manic depressive psychosis drugs. Furthermore, compounds of the present invention have strong effects for increasing anesthesia and sleep when used in combination with anesthetics and hypnotics.

Compounds of the present invention are also useful for pre-anesthetics and sleep-inducing agents in addition to the above-mentioned strong controlling effect on the fighting motion of a mouse.

Furthermore, as to the central nervous controlling activities, the present compounds have various pharmacological activities such as muscle relaxing action, apomorphine-vomiting inhibitory action, ptosis action, hypothermy action, spontaneous movement controlling action, hypermotion controlling action of rats, anti-methanphetamine action, methanphetamine group toxicities lowering action, analgetic action and antinoradrenaline action but they have only weak activities in anticholine action, cardio-inhibitory action and catalepsy-inducing action. Therefore, compounds of the present invention are useful for central nervous controlling agents such as central muscle relaxizating agents, sleep-inducing agents, pre-operative drugs, anti-schizophrenia agents, sedatives, antianxiety drugs, anti-manic depressive psychosis agents, antipyretic agents, analgetic agents and depressors, without showing side-effects such as feeling thirst, constipation, tachycordia, parkinsonism, and/or delayed dyscinesia which exist with conventional central nervous controlling agents.

In the present specification, the term "an alkyl group having 1 to 6 carbon atoms" means an alkyl group having straight or branched form having 1 to 6 carbon atoms and examples include methyl group, ethyl group, propyl group, isopropyl group, butyl group, isobutyl group, tert-butyl group, sec-butylpentyl group, hexyl group and the like.

The term "an alkenyl group having 2 to 4 carbon atoms" means an alkenyl group having straight or branched chain form having 2 to 4 carbon atoms and examples include vinyl group, allyl group, 2-butenyl group, 1-methyl-allyl group and the like. Examples of the term "an alkynyl group having 2 to 4 carbon atoms" include ethynyl group, 2-propynyl group, 2-butynyl group, 1-methyl-2-propynyl group and the like. The term "a phenylalkyl group of which the alkylene group has 1 to 4 carbon atoms" means a phenylalkyl group composed of a phenyl group with an alkylene group having straight or branched form having 1 to 4 carbon atoms and examples thereof include benzyl-2-phenylethyl group, 1-phenylethyl group, 3-phenylpropyl group, 4-phenylbutyl group, 1,1-dimethyl-2-phenylethyl group and the like. The term "an alkyl group having 1 to 4 carbon atoms" means an alkyl group having straight or branched chain having 1 to 4 carbon atoms, and examples thereof include methyl group, ethyl group, propyl group, isopropyl group, butyl group, isobutyl group, tert-butyl group and the like. The examples of the term "a halogen atom" include florine atom, chlorine atom, bromine atom and iodine atom. The term "an alkanoyloxy group having 1 to 4 carbon atoms" means an alkanoyloxy group having straight or branched chain having 1 to 4 carbon atoms and the examples thereof include formyloxy group, acetyloxy group, propionyloxy group, butyryloxy group and the like. The term "$C_{3-8}$ cycloalkyl group" means a cycloalkyl group having 3 to 8 carbon atoms and examples thereof include cyclopropyl group, cyclopentyl group, cyclohexyl group, cycloheptyl group, cyclooctyl group and the like. The term "$C_{1-4}$ alkoxy group" means a straight or branched alkoxy group having 1 to 4 carbon atoms and examples thereof include methoxy group, ethoxy group, propoxy group, isopropoxy group, butoxy group, isobutoxy group, tert-butoxy group and the like.

Concrete examples of a phenyl group which may have 1 to 3 substituted groups selected from the group consisting of halogen atoms, $C_{1-4}$ alkyl groups and $C_{1-4}$ alkoxy groups include phenyl group, 2-methoxyphenyl group, 4-methoxyphenyl group, 3-methoxyphenyl group, 2-ethyoxyphenyl group, 4-butoxyphenyl group, 3,4-dimethoxyphenyl group, 3,4,5-trimethoxyphenyl, 3-isopropoxyphenyl group, 2-methylphenyl group, 3-methylphenyl group, 4-methylphenyl group, 2-ethylphenyl group, 4-butylphenyl group, 3,4-diethylphenyl group, 3,4,5-trimethylphenyl group, 2-chlorophenyl group, 3-bromophenyl group, 4-fluorophenyl group, 3-chlorophenyl group, 4-chlorophenyl group, 2-fluorophenyl group, 3,4-dichlorophenyl group, 3,4,5-trichlorophenyl group, 4-chloro-3-methylphenyl group, 2-methoxy-3-chlorophenyl group, 4-bromophenyl group, 2-bromophenyl group, 4-iodophenyl group and the like.

The term "$C_{1-4}$ alkanoyl group" means a straight or branched chain alkanoyl group having 1 to 4 carbon atoms and the examples thereof include formyl group, acetyl group, propionyl group, butyryl group, isobutyryl group and the like.

Concrete examples of $C_{1-4}$ alkyl group which may have one substituted group such as a hydroxy group, phenyl group or $C_{1-4}$ alkonoyloxy group include hydroxymethyl group, 2-hydroxyethyl group, 3-hydroxypropyl group, 4-hydroxybutyl group, 2-hydroxypropyl group, acetyloxymethyl group, 2-acetyloxyethyl group, 2-propionyloxyethyl group, 3-acetyloxypropyl group, 4-butyloxybutyl group, 2-acetyloxypropyl group, benzyl group, 2-phenylethyl group, 1-phenylethyl group, 3-phenylpropyl group, 4-phenylbutyl group, 1,1-dimethyl-2-phenylethyl group and the like.

Listed below are representative examples of compounds according to the present invention. 3,4-dehydro compounds means that the carbon-carbon bond between the 3- and 4-positions in the carbostyril skeleton is a double bond. For example, "5-[2-hydroxy-3-(4-phenylpiperazinyl)-propoxy]-3,4-dihydrocarbostyril and 5-[2-hydroxy-3-(4-phenylpiperazinyl)propoxy]carbostyril" will be described as "5-[2-hydroxy-3-(4-phenylpiperazinyl)propoxy]-3,4-dichydrocarbostyril and its 3,4-dehydro compound".

6-[2-Hydroxy-3-(4-phenylpiperazinyl)propoxy]-3,4-dihydrocarbostyril and its 3,4-dehydro compound 7-[2-Hydroxy-3(4-phenylpiperazinyl)propoxy]-3,4-dihydrocarbostyril and its 3,4-dehydro compound 6-[3-Hydroxy-3-(4-phenylpiperazinyl)propoxy]-3,4-dihydrocarbostyril and its 3,4-dehydro compound 7-[4-Hydroxy-5-(4-phenylpiperazinyl)pentyloxy]-3,4-dihydrocarbostyril and its 3,4-dehydro compound 1-Methyl-5-[2-hydroxy-3-(4-phenylpiperazinyl)propoxy]-3,4-dihydrocarbostyril and its 3,4-dehydro compound 1-Ethyl-6-[2-hydroxy-3-(4-phenylpiperazinyl)propoxy]-3,4-dihydrocarbostyril and its 3,4-dehydro compound 1-Methyl-7-[2-hydroxy-3-(4-phenylpiperazinyl)propoxy]-3,4-dihydrocarbostyril and its 3,4-dehydro compound 1-Methyl-8-[2-hydroxy-3-(4-phenylpiperazinyl)propoxy]-3,4-dihydrocarbostyril and its 3,4-dehydro compound 1-(3-Methylbutyl)-5-[2-hydroxy-3-(4-phenylpiperazinyl)propoxy[-3,4-dihydrocarbostyril and its 3,4-dehydro compound 1-Hexyl-6-[2-hydroxy-3-(4-phenylpiperazinyl)propoxy]-3,4-dihydrocarbostyril and its 3,4-dehydro compound 1-Allyl-5-[2-hydroxy-3-(4-phenylpiperazinyl)propoxy]-3,4-dihydrocarbostyril and its 3,4-dehydro compound 1-(2-Butenyl)-6-[2-hydroxy-3-(4-phenylpiperazinyl)-propoxy]-3,4-dihydrocarbostyril and its 3,4-dehydro compound 1-Allyl-7-[2-hydroxy-3-[4-phenylpiperazinyl)propoxy]-3,4-dihydrocarbostyril and its 3,4-dehydro compound 1-Benzyl-5-[2-hydroxy-3-(4-phenylpiperazinyl)propoxy]-3,4-dihydrocarbostyril and its 3,4-dehydro compound.

1-(3-Phenylpropoxy)-5-{2-hydroxy-3-[4-(4-methylphenyl)piperazinyl]propoxy}-3,4-dihydrocarbostyril and its 3,4-dehydro compound 1-(4-Phenylbutyl)-6-[2-hydroxy-3-(4-phenylpiperazinyl)propoxy]-3,4-dihydrocarbostyril and its 3,4-dehydro compound 1-Benzyl-7-[2-hydroxy-3-(4-phenylpiperazinyl)propoxy]-3,4-dihydrocarbostyril and its 3,4-dehydro compound 1-Benzyl-8-[2-hydroxy-3-(4-phenylpiperazinyl)propoxy]-3,4-dihydrocarbostyril and its 3,4-dehydro compound 1-Methyl-5-bromo-6-[2-hydroxy-3-(4-phenylpiperazinyl)propoxy]-3,4-dihydrocarbostyril and its 3,4-dehydro compound 6-Fluoro-7-[2-hydroxy-3-(4-phenylpiperazinyl)propoxy]-3,4-dihydrocarbostyril and its 3,4-dehydro compound 1-Benzyl-5-chloro-8-[2-hydroxy-3-(4-phenylpiperazinyl)propoxy]-3,4-dihydrocarbostyril and its 3,4-dehydro compound 6,8-Dichloro-5-[2-hydroxy-3-(4-phenylpiperazinyl)-propoxy-3,4-dihydrocarbostyril and its 3,4-dehydro compound 6-Chloro-8-bromo-7-[2-hydroxy-3-(4-phenylpiperazinyl)propoxy]-3,4-dihydrocarbostyril and its 3,4-dehydro compound 1-Methyl-5,6-dibromo-8-(2-hydroxy-3-(4-phenylpiperazinyl)propoxy]3,4-dihydrocarbostyril and its 3,4-dehydro compound 1-Methyl-5-{2-hydroxy-3-[4-(2-chlorophenyl)-piperazinyl]propoxy}-3,4-dihydrocarbostyril and its 3,4-dehydro compound 6-{2-Hydroxy-3-[4-(3-bromophenyl)piperazinyl]-propoxy}-3,4-dihydrocarbostyril and its 3,4-dehydro compound 7-{2-Hydroxy-3-[4-(4-fluorophenyl)piperazinyl]-propoxy}-3,4-dihydrocarbostyril and its 3,4-dehydro compound 5-{2-Hydroxy-3-[4-(2-methylphenyl)piperazinyl]-propoxy}3,4-dihydrocarbostyril and its 3,4-dehydro compound 1-Benzyl-6-{2-hydroxy-3-[4-(3-methylphenyl)-piperazinyl]propoxy}-3,4-dihydrocarbostyril and its 3,4-dehydro compound 1-Methyl-5-{2-hydroxy-3-[4-(4-ethylphenyl)-piperazinyl]propoxy}-3,4-dihydrocarbostyril and its 3,4-dehydro compound 6-{2-Hydroxy-3-[4-(2-propylphenyl)piperazinyl]-propoxy}-3,4-dihydrocarboxtyril and its 3,4-dehydro compound 5-{2-Hydroxy-3-[4-(2-methoxyphenyl)piper azinyl]-propoxyL}-3,4-dihydrocarbotyril and its 3,4-dehydro compound.

1-Methyl-6-{2-hydroxy-3-[4-(3-methoxyphenyl)-piperazinyl]propoxy}-3,4-dihydrocarbostyril and its 3,4-dehydro compound 7-{2-Hydroxy-3-[4-(4-methoxyphenyl)piperazinyl]-propoxy}-3,4-dihydrocarbostyril and its 3,4-dehydro compound 6-{2-Hydroxy-3-[4-(2-ethoxyphenyl)piperazinyl]-propoxy}-3,4-dihydrocarbostyril and its 3,4-dehydro compound 8-Chloro-5-{2-hydroxy-3-[4-(4-chlorophenyl)-piperazinyl]propoxy}-3,4-dihydrocarbostyril and its 3,4-dehydro compound 1-Methyl-6-chloro-7-{2-hydroxy-3-[4-(4-chlorophenyl)piperazinyl]propoxy}-3,4-dihydrocarbostyril and its 3,4-dehydro compound 1-Allyl-6-chloro-7-{2-hydroxy-3-[4-(4-methoxypheny)-piperazinyl]propoxy}-3,4-dihydrocarbostyril and its 3,4-dehydro compound 6-Chloro-5-{2-hydroxy-3-[4-(4-methylphenyl)-piperazinyl]propoxy}-3,4-dihydrocarbostyril and its 3,4-dehydro compound 6,8-Dibromo-5-{2-hydroxy-3-[4-(4-methylphenyl)-piperazinyl]propoxy}-3,4-dihydrocarbostyril and its 3,4-dehydro compound 5-(4-Phenylpiperazinylmethoxy-3,4-dihydrocarbostyril and its 3,4-dehydro compound 5-[2-(4-Phenylpiperazinyl)ethoxy]-3,4-dihydrocarbostyril and its 3,4-dehydro compound 7-[2-(4-Phenylpiperazinyl)ethoxy]-3,4-dihydrocarbostyril and its 3,4-dehydro compound 8-[2-(4-Phenylpiperazinylethoxy]-3,4-dihydrocarbostyril and its 3,4-dehydro compound 5-[3-(4-Phenylpiperazinyl)propoxy]-3,4-dihydrocarbostyril and its 3,4-dihydro compound 7-[3-(4-Phenylpiperazinyl)propoxy]-3,4-dihydrocarbostyril and its 3,4-dehydro compound 6-[7-(4-Phenylpiperazinyl)heptyloxy]-3,4-dihydrocarbostyril and its 3,4-dehydro compound 5-[4-(4-Phenylpiperazinylpropoxy-3,4-dihydrocarbostyril and its 3,4-dehydro compound 7-[4-(4-Phenylpiperazinyl)butoxy]-3,4-dihydrocarbostryil and its 3,4-dehydro compound 6-[5-(4-Phenylpiperazinyl)pentyloxy]-3,4-dihydrocarbostyril and its 3,4-dehydro compound 8-[5-(4-Phenylpiperazinyl)pentyloxy]-3,4-dihydrocarbostyril and its 3,4-dehydro compound 7-[6-(4-Phenylpiperazinyl)hexyloxy]-3,4-dihydrocarbostyril and its 3,4-dehydro compound 1-Methyl-5-[2-(4-Phenylpiperazinyl)ethoxy]-3,4-dihydrocarbostyril and its 3,4-dehydro compound 1-Methyl-6-[3-(4-Phenylpiperazinyl)propoxy]-3,4-dihydrocarbostyril and its 3,4-dehydro compound 1-Methyl-7-[3-(4-phenylpiperazinyl)propoxy]-3,4-dihydrocarbostyril and its 3,4-dehydro compound 1-Hexyl-6-[3-phenylpiperazinyl)propoxy]-3,4-dihydrocarbostyril and its 3,4-dehydro compound 1-Allyl-5-[3-(4-phenylpiperazinyl)propoxy]-3,4-dihydrocarbostyril and its 3,4-dehydro compound 1-Allyl-6-[3-(4-phenylpiperazinyl)propoxy]-3,4-dihydrocarbostyril and its 3,4-dehydro compound 1-(1-Methylallyl)-7-[3-(4-phenylpiperazinyl)propoxy]-3,4-dihydrocarbostyril and its 3,4-dehydro compound 1-(2-Propynyl)--7-[3-(4-phenylpiperazinyl)-propoxy]-3,4-dihydrocarbostyril and its 3,4-dehydro compound 1-Benzyl-5-[2-(4-phenylpiperazinyl)ethoxy]-3,4-dihydrocarbostyril and its 3,4-dehydro compound 1-(2-Phenylethyl)-6-[3-(4-phenylpiperazinyl)propoxy]-3,4-dihydrocarbostyril and its 3,4-dehydro compound 1-(4-Phenylbutyl)-5-[3-(4-phenylpiperazinyl)-propoxy]-3,4-dihydrocarbostyril and its 3,4-dehydro compound 1-Benzyl-7-[3-(4-phenylpiperazinyl)propoxy]-3,4-dihydrocarbostyril and its 3,4-dehydro compound 5-{3-[4-(2-Methoxyphenyl)piperazinyl]propoxy}-3,4-dihydrocarbostyril and its 3,4-dehydro compound 5-{3-[4-(3-Methylphenyl)piperazinyl]propoxy}-3,4-dihydrocarbostyril and its 3,4-dehydro compound 6-{3-[4-(4-Methylphenyl)piperazinyl]propoxy}-3,4-dihydrocarbostyril and its 3,4-dehydro compound 7-{2-[4-(4-Propylphenyl)piperazinyl]ethoxy}-3,4-dihydrocarbostyril and its 3,4-dehydro compound 5-{3-[4-(4-Chlorophenyl)piperazinyl]propoxy}-3,4-dihydrocarbostyril and its 3,4-dehydro compound 6-{3-[4-(4-Bromophenyl)piperazinyl]propoxy}-3,4-dihydrocarbostyril and its 3,4-dehydro compound 7-{2-[4-(2-Chlorophenyl)piperazinyl]ethoxy}-3,4-dihydrocarbostyril and its 3,4-dehydro compound 1-Methyl-5-{3-[4-(4-chlorophenyl)piperazinyl]propoxy}-3,4-dihydrocarbostyril and its 3,4-dehydro compound 1-Benzyl-6-{2-[4-(2-bromophenyl)piperazinyl]ethoxy}-3,4-dihydrocarbostyril and its 3,4-dehydro compound 1-Allyl-7-{4-[4-(4-bromophenyl)piperazinyl]butoxy}-3,4-dihydrocarbostyril and its 3,4-dehydro compound 1-Methyl-6-{3-[4-(4-methylphenyl)piperazinyl]propoxy}-3,4-dihydrocarbostyril and its 3,4-dehydro compound 1-Benzyl-5-{3-[4-(2-methylphenyl)piperazinyl]propoxy}-3,4-dihydrocarbostyril and its 3,4-dehydro compound 1-Methyl-7-{3-[4-(4-methoxyphenyl)piperazinyl]propoxy}-3,4-dihydrocarbostyril and its 3,4-dehydro compound 1-Benzyl-5-{3-[4-(4-methoxyphenyl)piperazinyl]propoxy}-3,4-dihydrocarbostyril and its 3,4-dehydro compound 8-Bromo-5-[3-(4-phenylpiperazinyl)propoxy]-3,4-dihydrocarbostyril and its 3,4-dehydro compound 1-Methyl-5-bromo-6-[2-(4-phenylpiperazinyl)ethoxy]-3,4-dihydrocarbostyril and its 3,4-dehydro compound 6-Fluoro-7-[3-(4-phenylpiperazinyl)propoxy]-3,4-dihydrocarbostyril and its 3,4-dehydro compound 6-Chloro-5-[2-(4-phenylpiperazinyl)ethoxy]-3,4-dihydrocarbostyril and its 3,4-dehydro compound 6-Chloro-5-{4-[4-(4-phenyl)piperazinyl]-butoxy}3,4-dihydrocarbostyril and its 3,4-dehydro compound 1-Allyl-6-chloro-7-{2-[4-(4-methoxyphenyl)-piperazinyl]ethoxy}-3,4-dihydrocarbostyril and its 3,4-dehydro compound 6,8-Dichloro-5-[2-(4-phenylpiperazinyl)ethoxy]-3,4-dihydrocarbostyril and its 3,4-dehydro compound 6-Chloro-8-bromo-7-[3-(4-phenylpiperazinyl)propoxy]-3,4-dihydrocarbostyril and its 3,4-dehydro compound 1-Methyl-5,6-dibromo-8-[2-(4-phenylpiperazinyl)ethoxy]-3,4-dihydrocarbostyril and its 3,4-dehydro compound 8-Chloro-5-{3-[4-(4-chlorophenyl)piperazinyl]propoxy}-3,4-dihydrocarbostyril and its 3,4-dehydro compound 1-Methyl-6-chloro-7-{2-[4-(4-chlorophenyl)-piperazinyl]ethoxy}-3,4-dihydrocarbostyril and its 3,4-dehydro compound 1-Benzyl-6,8-dichloro-5-{2-[4-(2-bromophenyl)-piperazinyl]ethoxy}-3,4-dihydrocarbostyril and its 3,4-dehydro compound 7-{3-[4-(2-Methoxyphenyl)piperazinyl]propoxy}-3,4-dihydrocarbostyril and its 3,4-dehydro compound 7-{3-[4-(3-Methoxyphenyl)piperazinyl]propoxy}-3,4-dihydrocarbostyril and its 3,4-dehydro compound 7-{3-[4-(4-Methoxyphenyl)piperazinyl]propoxy}-3,4-dihydrocarbostyril and its 3,4-dehydro compound 7-{3-[4-(2-Ethoxyphenyl)piperazinyl]propoxy}-3,4-dihydrocarbostyril and its 3,4-dehydro compound 1-Methyl-7-{3-[4-(2-methoxyphenyl)piperazinyl]propoxy}-3,4-dihydrocarbostyril and its 3,4-dehydro compound 1-Allyl-7-{3-[4-(2-methoxyphenyl)piperazinyl]propoxy}-3,4-dihydrocarbostyril and its 3,4-dehydro compound 1-Benzyl-7-{3-[4-(2-methoxyphenyl)piperazinyl]propoxy}-3,4-dihydrocarbostyril and its 3,4-dehydro compound 1-(2-Propynyl)-7-{3-[4-(2-methoxyphenyl)piperazinyl]propoxy}-3,4-dihydrocarbostyril and its 3,4-dehydro compound 7-{3-[4-(3,4-Dimethoxyphenyl)piperazinyl)propoxy}-3,4-dihydrocarbostyril and its 3,4-dehydro compound 7-{3-[4-(3,4,5-Trimethoxyphenyl)piperazinyl]propoxy}-3,4-dihydrocarbostyril and its 3,4-dehydro compound 5-{3-[4-(3,4-Dimethoxyphenyl)piperazinyl]propoxy}-3,4-dihydrocarbostyril and its 3,4-dehydro compound 1-Methyl-7-{3-[4-(3,4-dimethoxyphenyl)piperazinyl]propoxy}-3,4-dihydrocarbostyril and its 3,4-dehydro compound 1-Benzyl-7-{3-[4-(3,4-dichlorophenyl)piperazinyl]propoxy}-3,4-dihydrocarbostyril and its 3,4-dehydro compound 7-{3-[4-(3,4-Dimethylphenyl)piperazinyl]propoxy}-3,4-dihydrocarbostyril and its 3,4-dehydro compound 5-[2-Methyl-3-(4-phenylpiperazinyl)propoxy]-3,4-dihydrocarbostyril and its 3,4-dehydro compound 7-[2-Methyl-3-(4-phenylpiperazinyl)propoxy]-3,4-dihydrocarbostyril and its 3,4-dehydro compound 4-Methyl-6-[3-(4-phenylpiperazinyl)propoxy]-3,4-dihydrocarbostyril and its 3,4-dehydro compound 7-[4-Methyl-5-(4-phenylpiperazinyl)pentyloxy]-3,4-dihydrocarbostyril and its 3,4-dehydro compound 7-[2-Ethyl-3-(4-phenylpiperazinyl)propoxy]-3,4-dihydrocarbostyril and its 3,4-dehydro compound 1-Methyl-7-[2-methyl-3-(4-phenylpiperazinyl)-propoxy]-3,4-dihydrocarbostyril and its 3,4-dehydro compound 1-Benzyl-7-[2-methyl-3-(4-phenylpiperazinyl)propoxy]-3,4-dihydrocarbostyril and its 3,4-dehydro compound 1-Allyl-7-[2-(methyl-3-(4-phenylpiperazinyl)propoxy]-3,4-dihydrocarbostyril and its 3,4-dehydro compound 1-(2-Propynyl)-7-[2-methyl-3-(4-phenylpiperazinyl)-propoxy-3,4-dihydrocarbostyril and its 3,4-dehydro compound 6-Chloro-5-[2-methyl-3-(4-phenylpiperazinyl)propoxy]-3,4-dihydrocarbostyril and its 3,4-dehydro compound 6-Chloro-8-bromo-7-[2-methyl-3-(4-phenylpiperazinyl)-propoxy]-3,4-dihydrocarbostyril and its 3,4-dehydro compound 7-{2-Methyl-3-[4-(2-methoxyphenyl)piperazinyl]propoxy}-3,4-dihydrocarbostyril and its 3,4-dehydro compound 1-Benzyl-5-{2-methyl-4-[4-(4-methylphenyl)-piperazinyl]butoxy}-3,4-dihydrocarbostyril and its 3,4-dehydro compound 7-{2-Methyl-3-[4-(3,4-dimethoxyphenyl)piperazinyl]-propoxy}-3,4-dihydrocarbostyril and its 3,4-dehydro compound 7-[2-Methyl-3-(3-methyl-4-phenylpiperazinyl)propoxy]-3,4-dihydrocarbostyril and its 3,4-dehydro compound 5-[2-Acetyloxy-3-(4-phenylpiperazinyl)-propoxy]-3,4-dihydrocarbostyril and its 3,4-dehydro compound 1-Methyl-6-[2-propionyloxy-3-(4-phenyl-piperazinyl)-propoxy]-3,4-dihydrocarbostyril and its 3,4-dehydro compound 7-{2-Acetyloxy-3-[4-(2-methoxyphenyl)piperazinyl]-propoxy}-3,4-dihydrocarbostyril and its 3,4-dehydro compound 7-{3-Acetyloxy-5-[4-(4-methylphenyl)piperazinyl]pentyloxy}-3,4-dihydrocarbostyril and its 3,4-dehydro compound 1-Benzyl-{2-acetyloxy-3-[4-(4-chlorophenyl)-piperazinyl]propoxy}-3,4-dihydrocarbostyril and its 3,4-dehydro compound 1-Allyl-8-[2-acetyloxy-3-(4-phenylpiperazinyl)propoxy]-3,4- dihydrocarbostyril and its 3,4-dehydro compound 6-Chloro-5-[2-acetyloxy-3-(4-phenylpiperazinyl)-propoxy]-3,4-dihydrocarbostyril and its 3,4-dehydro compound 1-Ethyl-7-[2-acetyloxy-3-(4-phenylpiperazinyl)propoxy]-3,4-dihydrocarbostyril and its 3,4-dehydro compound 1-(2-Propynyl)-7-[2-acetyloxy-3-(4-phenylpiperazinyl)-propoxy]-3,4-dihydrocarbostyril and its 3,4-dehydro compound 7-{2-Isobutyloxy-3-[4-(2-methoxyphenyl)piperazinyl]-propoxy}-3,4-dihydrocarbostyril and its 3,4-dehydro compound 4-[2-Acetyloxy-3-(4-phenylpiperazinyl)-propoxy]-3,4-dihydrocarbostyril and its 3,4-dehydro compound 4-Methyl-7-[2-acetyloxy-3-(4-phenylpiperazinyl)-propoxy]-3,4-dihydrocarbostyril and its 3,4-dehydro compound 4-Phenyl-7-[2-acetyloxy-3-(4-phenylpiperazinyl)-propoxy]-3,4-dihydrocarbostyril and its 3,4-dehydro compound 5-[2-()3,4,5-Trimethoxybenzoyloxy)-3-(4-phenylpiperazinyl)propoxy]-3,4-dihydrocarbostyril and its 3,4-dehydro compound 1-Benzyl-6-[2-(3,4,5-trimethoxybenzoyloxy-3-(4-phenylpiperazinyl)propoxy]-3,4-dihydrocarbostyril and its 3,4-dehydro compound 7-[2-(3,4,5-Trimethoxybenzoyloxy)-3-(4-phenyl-piperazinyl)propoxy]-3,4-dihydrocarbostyril and its 3,4-dehydro compound 1-Methyl-7-[2-(3,4,5-trimethoxybenzyloxy)-3-(4-phenylpiperazinyl)propoxy]-3,4-dihydrocarbostyril and its 3,4-dehydro compound 7-{2-(3,4,5-Trimethoxybenzoyloxy)-3-[4-(2-methoxyphenyl)piperazinyl]propoxy}-3,4-dihydrocarbostyril and its 3,4-dehydro compound 1-Benzyl-7-[2-(3,4,5-trimethoxybenzoyloxy)-3-(4-phenylpiperazinyl)propoxy]-3,4-dihydrocarbostyril and its 3,4-dehydro compound 4-Methyl-7-[2-(3,4,5-trimethoxybenzoyloxy)-3-(4-phenylpiperazinyl)propoxy]-3,4-dihydrocarbostyril and its 3,4-dehydro compound 4-Phenyl-8-[2-(3,4,5-trimethoxybenzoyloxy)-3-(4-phenylpiperazinyl)propoxy]-3,4-dihydrocarbostyril and its 3,4-dehydro compound 1-Allyl-6-chloro-7-{2-(3,4,5-trimethoxybenzoyloxy)-3-[4-(3,4-dimethoxyphenyl)piperazinyl]-propoxy}-3,4-dihydrocarbostyril and its 3,4-dehydro compound 7-[2-Hydroxy-3-(3-methyl-4-phenylpiperazinyl)-propoxy]-3,4-dihydrocarbostyril and its 3,4-dehydro compound 7-[3-(3-Methyl-4-phenhylpiperazinyl)propoxy]-3,4-dihydrocarbostyril and its 3,4-dehydro compound 7-{3-[3-(Methyl-4-(4-chlorophenyl)piperazinyl]propoxy}-3,4-dihydrocarbostyril and its 3,4-dehydro compound 7-[3-(1-Methyl-4-phenylpiperazinyl)propoxy]-3,4-dihydrocarbostyril and its 3,4-dehydro compound 7-{3-[3-Methyl-4-(2-methoxyphenyl)piperazinyl]propoxy}-3,4-dihydrocarbostyril and its 3,4-dehydro compound 8-[3-(3-Ethyl-4-phenylpiperazinyl)propoxy]-3,4-dihydrocarbostyril and its 3,4-dehydro compound 4-[3-(3-Methyl-4-phenylpiperazinyl)propoxy]-3,4-dihydrocarbostyril and its 3,4-dehydro compound 1-Methyl-[3-(3-methyl-4-phenylpiperazinyl)-propoxy]-3,4-dihydrocarbostyril and its 3,4-dehydro compound 1-Benzyl-[3-(1-methyl-4-phenylpiperazinyl)-propoxy]-3,4-dihydrocarbostyril and its 3,4-dehydro compound 4-Methyl-7-[3-(4-phenylpiperazinyl)propoxy]-3,4-dihydrocarbostyril and its 3,4-dehydro compound 4-Phenyl-7-{3-[4-(2-methoxyphenyl)piperazinyl]-propoxy}-3,4-dihydrocarbostyril and its 3,4-dehydro compound 4-[3-(4-Phenylpiperazinyl)propoxy]-3,4-dihydrocarbostyril and its 3,4-dehydro compound 4-Ethyl-7-{3-[4-(2-methoxyphenyl)piperazinyl]-propoxy}-3,4-dihydrocarbostyril and its 3,4-dehydro compound 1,4-Dimethyl-7-[3-(4-phenylpiperazinyl)propoxy]-3,4-dihydrocarbostyril and its 3,4-dehydro compound 1-Benzyl-4-phenyl-7-{3-[4-(2-chlorophenyl)-piperazinyl]propoxy}-3,4-dihydrocarbostyril and its 3,4-dehydro compound 5-[2-Hydroxy-3-(4-cyclohexylpiperazinyl)-propoxy]-3,4-dihydrocarbostyril and its 3,4-dehydro compound 6-[2-Acetyloxy-3-(4-cycloheptylpiperazinyl)propoxy]-3,4-dihydrocarbostyril and its 3,4-dehydro compound 7-[3-(4-Cyclohexylpiperazinyl)propoxy]-3,4-dihydrocarbostyril and its 3,4-dehydro compound 4-[3-(4-Cyclohexylpiperazinyl)propoxy]-3,4-dihydrocarbostyril and its 3,4-dehydro compound 1-Methyl-7-[3-(4-cyclohexylpiperazinyl)propoxy]-3,4-dihydrocarbostyril and its 3,4-dehydro compound 1-Benzyl-7-[2-methyl-3-(4-cyclohexylpiperazinyl)-propoxy]-3,4-dihydrocarbostyril and its 3,4-dehydro compound 5-[3-(4-Cyclohexylpiperazinyl)propoxy]-3,4-dihydrocarbostyril and its 3,4-dehydro compound 4-Methyl-7-[3-(4-cyclohexylpiperazinyl)propoxy]-3,4-dihydrocarbostyril and its 3,4-dehydro compound 4-Phenyl-6-[2-methyl-3-(4-cyclohexylpiperazinyl)-propoxy]-3,4-dihydrocarbostyril and its 3,4-dehydro compound 1-(2-Propinyl)-7-[4-(4-cyclohexylpiperazinyl)butoxy]-3,4-dihydrocarbostyril and its 3,4-dehydro compound 6,8-Dichloro-5-[3-(4-cyclohexylpiperazinyl)-propoxy]-3,4-dihydrocarbostyril and its 3,4-dehydro compound 5-[2-Acetyloxy-3-(4-benzylpiperazinyl)propoxy]-3,4-dihydrocarbostyril and its 3,4-dehydro compound 6-[2-Hydroxy-3-(4-benzylpiperazinyl)propoxy]-3,4-dihydrocarbostyril and its 3,4-dehydro compound 7-[3-(4-Benzylpiperazinyl)propoxy]-3,4-dihydrocarbostyril and its 3,4-dehydro compound
4-[3-(4-Benzylpiperazinyl)propoxy]-3,4-dihydrocarbostyril and its 3,4-dehydro compound
6-[3-(4-Benzylpiperazinyl)propoxy]-3,4-dihydrocarbostyril and its 3,4-dehydro compound
1-Methyl-7-[2-methyl-3-(4-benzylpiperazinyl)propoxy]-3,4-dihydrocarbostyril and its 3,4-dehydro compound
1-Benzyl-7-[3-(4-benzylpiperazinyl)propoxy]-3,4-dihydrocarbostyril and its 3,4-dehydro compound
4-Methyl-7-[3-(4-benzylpiperazinyl)propoxy]-3,4-dihydrocarbostyril and its 3,4-dehydro compound
4-Phenyl-7-[3-(4-benzylpiperazinyl)propoxy]-3,4-dihydrocarbostyril and its 3,4-dehydro compound
1-Allyl-6-[4-benzylpiperazinyl)butoxy]-3,4-dihydrocarbostyril and its 3,4-dehydro compound
1-(2-Propynyl)-8-[2-(4-benzylpiperazinyl)-ethoxy]-3,4-dihydrocarbostyril and its 3,4-dehydro compound
6,8-Dichloro-5-[3-(4-benzylpiperazinyl)-propoxy]-3,4-dihydrocarbostyril and its 3,4-dehydro compound
7-[2-Acetyloxy-3-(4-benzylpiperazinyl)-propoxy]-3,4-dihydrocarbostyril and its 3,4-dehydro compound
7-{3-[4-(1-Phenylethyl)piperazinyl]propoxy}-3,4-dihydrocarbostyril and its 3,4-dehydro compound
7-{3-[4-(4-Phenylbutyl)piperazinyl]propoxy}-3,4-dihydrocarbostyril and its 3,4-dehydro compound
5-{2-Hydroxy-3-[4-(2-acetyloxy)piperazinyl]-propoxy}-3,4-dihydrocarbostyril and its 3,4-dehydro compound
7-{3-[4-(2-Acetyloxyethyl)piperazinyl]-propoxy}-3,4-dihydrocarbostyril and its 3,4-dehydro compound
8-{2-Methyl-3-[4-(2-acetyloxyethyl)piperazinyl]-propoxy}-3,4-dihydrocarbostyril and its 3,4-dehydro compound
4-{3-[4-(2-Acetyloxyethyl)piperazinyl]propoxy}-3,4-dihydrocarbostyril and its 3,4-dehydro compound
7-{3-[4-(4-Butyloxybutyl)piperazinyl]propoxy}-3,4-dihydrocarbostyril and its 3,4-dehydro compound
1-Methyl-7-{3-[4-(2-acetyloxyethyl)piperazinyl]-propoxy}-3,4-dihydrocarbostyril and its 3,4-dehydro compound
4-Phenyl-7-{3-[4-(2-acetyloxyethyl)piperazinyl]propoxy}-3,4-dihydrocarbostyril and its 3,4-dehydro compound
7-{2-Hydroxy-3-[4-(2-acetyloxyethyl)piperazinyl]-propoxy}-3,4-dihydrocarbostyril and its 3,4-dehydro compound
5-{2-Acetyloxy-3-[4-(2-hydroxyethyl)piperazinyl]-propoxy}-3,4-dihydrocarbostyril and its 3,4-dehydro compound
7-{3-[4-(2-Hydroxyethyl)piperazinyl]propoxy}-3,4-dihydrocarbostyril and its 3,4-dehydro compound
7-{3-[4-(4-Hydroxybutyl)piperazinyl]propoxy}-3,4-dihydrocarbostyril and its 3,4-dehydro compound
7-{3-[4-(1-Hydroxyethyl)piperazinyl]propoxy}-3,4-dihydrocarbostyril and its 3,4-dehydro compound
4-{2-[4-(2-Hydroxyethyl)piperazinyl]propoxy}-3,4-dihydrocarbostyril and its 3,4-dehydro compound
4-Methyl-7-{3-[4-(2-hydroxyethylpiperazinyl]propoxy}-3,4-dihydrocarbostyril and its 3,4-dehydro compound
7-{2-Hydroxy-3-[4-(2-hydroxyethyl)piperazinyl]-propoxy}-3,4-dihydrocarbostyril and its 3,4-dehydro compound
5-[3-(4-Benzoylpiperazinyl)propoxy]-3,4-dihydrocarbostyril and its 3,4-dehydro compound
7-[2-Acetyloxy-3-(4-benzoylpiperazinyl)propoxy]-3,4-dihydrocarbostyril and its 3,4-dehydro compound
7-[3-(4-Benzoylpiperazinyl)propoxy]-3,4-dihydrocarbostyril and its 3,4-dehydro compound
8-[3-(4-Benzoylpiperazinyl)propoxy]-3,4-dihydrocarbostyril and its 3,4-dehydro compound
1-Methyl-7-[3-(4-benzoylpiperazinyl)propoxy]-3,4-dihydrocarbostyril and its 3,4-dehydro compound
4-Phenyl-7-[3-(4-benzoylpiperazinyl)propoxy]-3,4-dihydrocarbostyril and its 3,4-dehydro compound
1-(2-Propynyl)-5-[2-(4-benzoylpiperazinyl)ethoxy]-3,4-dihydrocarbostyril and its 3,4-dehydro compound
6-Chloro-5-[4-(4-benzoylpiperazinyl)butoxy]-3,4-dihydrocarbostyril and its 3,4and its 3,4-dehydro compound
5-[3-(4-Acetylpiperazinyl)propoxy]-3,4-dihydrocarbostyril and its 3,4-dehydro compound
7-[3-(4-Acetylpiperazinyl)propoxy]-3,4-dihydrocarbostyril and its 3,4-dehydro compound
8-[2-Acetyloxy-3-(4-acetylpiperazinyl)propoxy]-3,4-dihydrocarbostyril and its 3,4-dehydro compound
1-Benzyl-7-[3-(4-acetylpiperazinyl)propoxy]-3,4-dihydrocarbostyril and its 3,4-dehydro compound
4-Methyl-7-[3-(4-acetylpiperazinyl)propoxy]-3,4-dihydrocarbostyril and its 3,4-dehydro compound
4-[3-(4-Acetylpiperazinyl)propoxy]-3,4-dihydrocarbostyril and its 3,4-dehydro compound
7-[3-(4-Butylpiperazinyl)propoxy]-3,4-dihydrocarbostyril and its 3,4-dehydro compound
1-Methyl-[4-(4-propionylpiperazinyl)butoxy]-3,4-dihydrocarbostyril and its 3,4-dehydro compound
8-Bromo-5-[3-(4-acetyl piperazinyl)propoxy]-3,4-dihydrocarbostyril and its 3,4-dehydro compound
7-[3-(4-Phenyl-hexahydro-1,4-diazepin-1-yl)propoxy]-3,4-dihydrocarbostyril and its 3,4-dehydro compound
6-[3-(4-Phenyl-hexahydro-1,4-diazepin-1-yl)propoxy]-3,4-dihydrocarbostyril and its 3,4-dehydro compound
5-[3-(4-Phenyl-hexahydro-1,4-diazepin-1-yl)propoxy]-3,4-dihydrocarbostyril and its 3,4-dehydro compound
4-[4-(4-Phenyl-hexahydro-1,4-diazepin-1-yl)butoxy]-3,4-dihydrocarbostyril and its 3,4-dehydro compound
7-{3-[4-(2-Methoxyphenyl)-hexahydro-1,4-diazepin-1-yl)propoxy}-3,4-dihydrocarbostyril and its 3,4-dehydro compound
6-{2-[4-(4-Chlorophenyl)-hexahydro-1,4-diazepin-1-yl]ethoxy}-3,4-dihydrocarbostyril and its 3,4-dehydro compound
7-[3-(4-Benzyl-hexahydro-1,4-diazepin-1-yl)propoxy]-3,4-dihydrocarbostyril and its 3,4-dehydro compound
7-[2-Hydroxy-3-(4-phenyl)-hexahydro-1,4-diazepin-1-yl)propoxy]-3,4-dihydrocarbostyril and its 3,4-dehydro compound
5-[2-Methyl-3-(4-phenyl-hexahydro-1,4-diazepin-1-yl)propoxy-3,4-dihydrocarbostyril and its 3,4-dehydro compound
1-Methyl-7-[3-(4-phenyl-hexahydro-1,4-diazepin-1-yl)propoxy-3,4-dihydrocarbostyril and its 3,4-dehydro compound
1-Benzyl-7-[3-(4-phenyl-hexahydro-1,4-diazepin-1-yl)propoxy]-3,4-dihydrocarbostyril and its 3,4-dehydro compound
4-Phenyl-7-[3-(4-phenyl-hexahydro-1,4-diazepin-1-yl)propoxy-3,4-dihydrocarbostyril and its 3,4-dehydro compound
8-Chloro-5-[3-(4-phenyl-hexahydro-1,4-diazepin-1-yl)propoxy-3,4-dihydrocarbostyril and its 3,4-dehydro compound
7-{2-Hydroxy-3-[4-(4-chlorophenyl)piperazinyl]-propoxy}-3,4-dihydrocarbostyril and its 3,4-dehydro compound 6-Chloro-7-{2-hydroxy-3-[4-(2-methoxyphenyl)-piperazinyl]propoxy}-3,4-dihydrocarbostyriland its 3,4-dehydro compound 4-Methyl-7-[2-hydroxy-3-(4-phenylpiperazinyl)propoxy]-3,4-dihydrocarbostyril and its 3,4-dehydro compound 6-{3-[4-(2-Methyoxyphenyl)piperazinyl]propoxy}-3,4-dihydrocarbostyril and its 3,4-dehydro compound 1-Methyl-5-[3-(4-phenylpiperazinyl)propoxy]-3,4-dihydrocarbostyril and its 3,4-dehydro compound 5-{2-[4-(4-Methylphenyl)piperazinyl]ethoxy}-3,4-dihydrocarbostyril and its 3,4-dehydro compound 8-{3-[4-(2-Methoxyphenyl)piperazinyl]propoxy}-3,4-dihydrocarbostyril and its 3,4-dehydro compound 7-{3-[4-(4-Methylphenyl)piperazinyl]propoxy}-3,4-dihydrocarbostyril and its 3,4-dehydro compound 5-{3-[4-(2-Ethoxyphenyl)piperazinyl]propoxy}-3,4-dihydrocarbostyril and its 3,4-dehydro compound 6-Chloro-7-[3-(4-phenylpiperazinyl)propoxy]-3,4-dihydrocarbostyril and its 3,4-dehydro compound 6-Bromo-7-[3-(4-phenylpiperazinyl)propoxy]-3,4-dihydrocarobstyril and its 3,4-dehydro compound 7-{3-[4-(2-Chlorophenyl)piperazinyl]propoxy}-3,4-dihydrocarbostyril and its 3,4-dehydro compound 7-{3-[4-(3-Chlorophenyl)piperazinyl]propoxy}-3,4-dihydrocarbostyril and its 3,4-dehydro compound 7-{3-[4-(4-Chlorophenyl)piperazinyl]-propoxy}-3,4-dihydrocarbostyril and its 3,4-dehydro compound 1-Allyl-7-[3-(4-phenylpiperazinyl)propoxy]-3,4-dihydrocarbostyril and its 3,4-dehydro compound 1-Hexyl-7-[3-(4-phenylpiperazinyl)propoxy]-3,4-dihydrocarbostyril and its 3,4-dehydro compound 1-Benzyl-5-[3-(4-phenylpiperazinyl)propoxy]-3,4-dihydrocarbostyril and its 3,4-dehydro compound 7-{3-[4-(3-Fluorophenyl)piperazinyl]propoxy}-3,4-dihydrocarbostyril and its 3,4-dehydro compound 5-{3-[4-Fluorophenyl)piperazinyl]propoxy}-3,4-dihydrocarbostyril and its 3,4-dehydro compound 7-{3-[4-(2-Fluorophenyl)piperazinyl]propoxy}-3,4-dihydrocarbostyril and its 3,4-dehydro compound 5-{3-[4-(3-Fluorophenyl)piperazinyl]propoxy}-3,4-dihydrocarbostyril and its 3,4-dehydro compound 5-{3-[4-(3,4,5-Trimethoxyphenyl)piperazinyl]propoxy}-3,4-dihydrocarbostyril and its 3,4-dehydro compound The compounds of the present invention can be prepared by various processes such as for example expressed as the following reaction process formula-1 and reaction process formula-2:

Reaction process formula-1

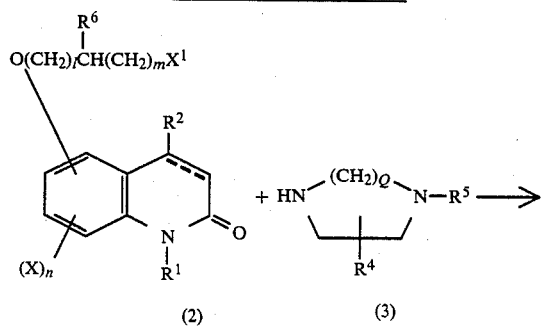

-continued
Reaction process formula-1

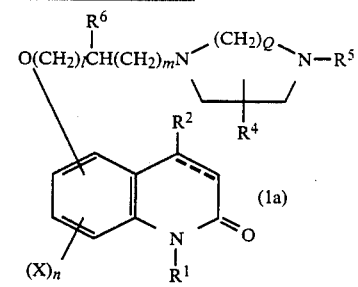

wherein $R^1$, $R^2$, $R^4$, $R^5$, X, l, m, n, Q, the carbon-carbon bond at the 3- and 4-positions in the carbostyril skeleton and the substituted position of the side chain of

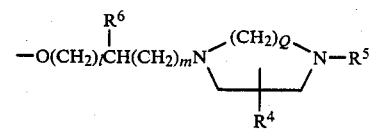

are all the same as defined above, $R^6$ is a hydrogen atom, a hydroxy group or an alkyl group having 1 to 4 carbon atoms, the substituted portion of the side chain of

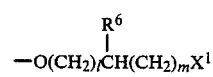

is any one of the 4-, 5-, 6-, 7- or 8- positions of the carbostyril skeleton, $X^1$ is a halogen atom or a group such as methyloxy group or tosyloxy group which can undergo a substitution reaction similar to a halogen atom.

As expressed by the reaction process formula-1, the compound represented by the general formula (1a) [wherein $R^3$ is defined other than an alkanoyloxy group having 1 to 4 carbon atoms or 3,4,5-trimethoxybenzoyloxy group as defined in the general formula (1)] is prepared by reacting a halogenoalkoxycarbostyril derivative represented by the general formula (2) with an amine derivative represented by the general formula (3) which can easily be prepared by known methods or by method similar to known methods.

The reaction between a compound represented by the general formula (2) and a compound represented by the general formula (3) can be completed in the absence of or in the presence of an inert solvent at a temperature ranging from room temperature to 200° C., preferably at a temperature ranging from 60°–120° C. for several hours to 24 hours. As to the inert solvents, an ether such as dioxane, tetrahydrofuran, ethylene glycol, dimethyl ether, etc.; an aromatic hydrocarbon such as benzene, toluene, xylene, etc.; a lower alcohol such as methanol, ethanol, isopropanol, etc.; and an aprotic polar solvent such as dimethylformamide, dimethylsulfoxide, etc. can be used. The reaction can advantageously be effected by using a basic compound as the dehydrohalogenating agent. The basic compound used in said reaction may be selected from a wide variety of known basic compounds including potassium carbonate, sodium carbonate, sodium hydroxide, sodium hydrogencarbonate, sodium amide, sodium hydride, a tertiary amine such as triethylamine, tripropylamine, pyridine or quinoline. The said reaction can also be effected by using an alkali metal iodide, for example, potassium iodide, or sodium iodide as the reaction accelerator. The ratio of amount of a compound represented by the general formula (2) to a compound represented by the general formula (3) in the above reaction is not subject to any specific restriction and may be suitably selected from a wide range, but usually, it is desirable that the latter is used in an amount ranging from equimolar to an excess quantity, preferably an equimolar to 5 times the molar quantity of the former, more preferably in an amount from equimolar to 1.2 times the molar quantity of the former.

A compound represented by the general formula (1c), [wherein $R^3$ as defined in the general formula (1) is an alkanolyoxy group having 1 to 4 carbon atoms or a 3,4,5-trimethoxybenzyloxy group] is prepared by a process as expressed in the following reaction process formula-2.

Reaction process formula-2

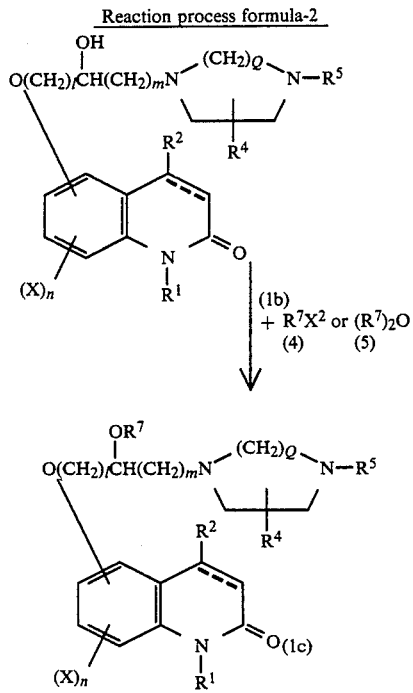

wherein $R^1$, $R^2$, $R^4$, $R^5$, X, l, m, n, Q, the carbon-carbon bond at the 3- and 4-positions in the carbostyril skeleton and the substituted portion of the side chain of

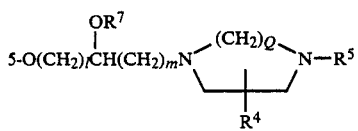

are all the same as defined above, $X^2$ is a halogen atom, and $R^7$ is an alkanoyloxy group having 1 to 4 carbon atoms a or 3,4,5-trimethoxybenzoyl group.

Thus a compound represented by the general formula (1c) of the present invention can be obtained by reacting a hydroxyalkoxycarbostyril derivative represented by the general formula (1b) with an acid halide or an acid anhydride represented by the general formula (4) or (5).

The reaction of a compound represented by the general formula (1b) with a compound represented by the general formula (4) or (5) can be carried out in the absence or presence of a suitable solvent and in the absence or presence of a suitable basic compound. The reaction can preferably be carried out in the presence of the basic compound.

The solvent used in the above reaction can representatively include an aromatic hydrocarbon such as benzene, toluene or xylene, a halogenated hydrocarbon such as chloroform or methylene chloride, acetone, pyridine, dimethylsulfoxide, dimethylformamide, or the like. The basic compound used in the above reaction can representatively include a tertiary amine such as triethylamine or pyridine, sodium hydroxide, potassium hydroxide or sodium hydride or the like.

The amount of a compound represented by the general formula (4) or (5) to a compound represented by the general formula (1b) is preferably at least an equimolar quantity of the latter, ranging from an equimolar to 5 times the molar quantity of the latter. The above reaction can be carried out at a temperature from room temperature to 150° C., preferably ranging from room temperature to 100° C., for several hours to 15 hours.

The starting material used in the present invention, that is a compound represented by the general formula (2), includes known compounds (U.S. Pat. No. 4,072,683) or novel compounds and can easily be prepared by the following reaction process formula-3:

Reaction process of formula-3

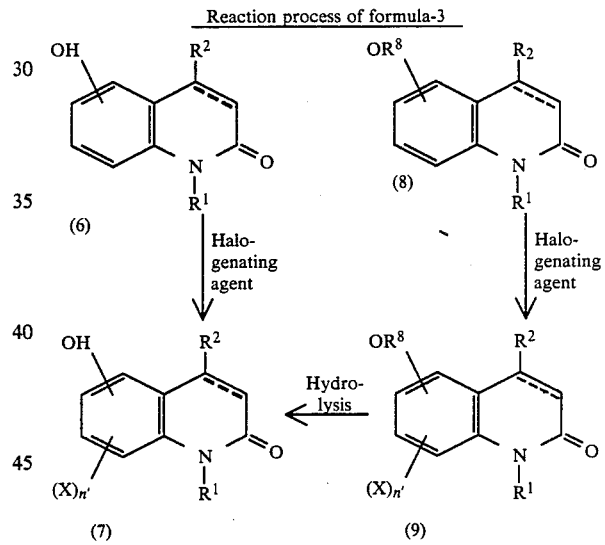

wherein $R^1$, $R^2$, X and the carbon-carbon bond at the 3- and 4-positions in the carbostyril skeleton are all the same as defined above, the substituted position of the hydroxy group is any one of the 4-, 5-, 6-, 7- or 8-positions of the carbostyril skeleton, n' is an integer of 1 or 2, and $R^8$ is an alkyl group having 1 to 4 carbon atoms or an alkanoyl group having 1 to 4 carbon atoms.

In the reaction process formula-3, a compound represented by the general formula (7) can be obtained by reacting a hydroxycarbostyril represented by the general formula (6) with a halogenating agent, or hydrolyzng a compound represented by the general formula (9), which is prepared by reacting an alkoxy- or alkanoyloxycarbostyril represented by the general formula (8) with a halogenating agent. The halogenation reaction mentioned above can be accomplished by using a known halogenating agent. Examples of such halogenating agents are fluorine, chlorine, bromine, iodine, xenon difluoride, sulfuryl chloride, sodium hypochlorite, hypochlorous acid, hypobromous acid, bleaching powder, iodine chloride and the like. The amount of the halogenating agent may be suitably selected from a wide range in accordance with the number of the halogen atoms to be introduced into the compound of (6) or (8). In the case of introducing one halogen atom, said halogenating agent is usually used in an equimolar or excess amount, preferably 1 to 1.5 times the molar quantity of the starting compound. In the case of introducing two halogen atoms, said halogenating agent is used in an amount ranging from 2 times the moles to a large excess, preferably 2 to 3 times the moles, of the respective starting compound. Such halogenation reaction is usually conducted in a suitable solvent such as, for example, water, methanol, ethanol, chloroform, carbon tetrachloride, acetic acid or a mixture thereof. The reaction temperature is not subject to any particular definition and can be suitably selected from a wide range, but usually the reaction is carried out at a temperature of around $-20°$ to $100°$ C., preferably $0°$ C. to room temperature. The reaction is completed within the period of about 30 minutes to 20 hours.

The hydrolysis reaction of a compound represented by the general formula (9) varies in accordance with the type of $R^8$ in the formula (9), for example, when $R^8$ is an alkanoyl group having 1 to 4 carbon atoms, the hydrolysis reaction can be carried out under the usual hydrolysis reaction conditions of an ester. Concretely, the hydrolysis can be carried out in the presence of a basic compound, such as sodium hydroxide, potassium hydroxide, barium hydroxide, sodium carbonate, and potassium hydrogen carbonate; a mineral acid such as sulfuric acid or hydrochloric acid; an organic acid such as acetic acid, and an aromatic sulfonic acid, in a solvent such as water, methanol, ethanol, acetone, dioxane, tetrahydrofuran or benzene. The reaction temperature usually ranges from room temperature to $150°$ C., preferably $50°$ to $100°$ C. The reaction is completed within 1 to 12 hours. Alternatively, when $R^8$ is an alkyl group having 1 to 4 carbon atoms, the hydrolysis reaction can be carried out under the hydrolysis conditions of ether. Concretely, the reaction can be carried out by using aluminum chloride, boron trifluoride, boron tribromide, hydrobromic acid or trimethylsilylchloride as a catalyst and in a solvent such as water, methanol, ethanol, benzene, methyl chloride or chloroform, at a temperature ranging from $0°$ to $200°$ C., preferably at room temperature to $120°$ C., for several to 12 hours. In both hydrolysis reactions, the amount of the catalyst used is not subject to any particular definition and is usually used in an excess amount compared to the compound (9) to be hydrolyzed.

Reaction process formula-4

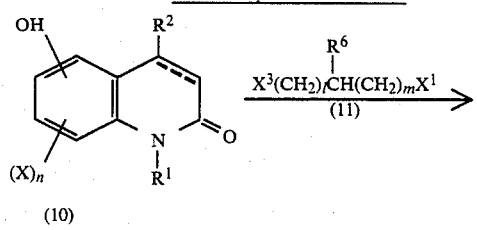

(10) 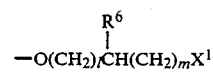 (11)

-continued
Reaction process formula-4

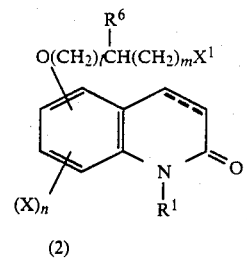

(2)

wherein $R^1$, $R^2$, $R^6$, X, $X^1$, l, m, n, the carbon-carbon bond at the 3- and 4-positions in the carbostyril skeleton, and the substituted position of the side chain of $$-O(CH_2)_l \overset{R^6}{\underset{|}{C}H}(CH_2)_m X^1$$

are all the same as defined above, $X^3$ is a halogen atom, the substituted position of the hydroxy group is any one of the 4-, 5-, 6-, 7- or 8-positions of the carbostyril skeleton.

In the reaction process formula-4, the reaction of a compound represented by the general formula (10) with a compound represented by the general formula (11) can preferably be carried out by using a basic compound as a dehydrohalogenating agent, in a suitable solvent, at a temperature ranging from room temperature to $200°$ C., preferably at $50°$ to $150°$ C., for several hours to 15 hours. Examples of suitable solvents are a lower alcohol such as methanol, ethanol, or isopropanol; a ketone such as acetone or methyl ethyl ketone; an ether such as dioxane, diethylene glycol or dimethyl ether; an aromatic hydrocarbon such as toluene or xylene; dimethylformamide, dimethylsulfoxide and hexamethylphosphoryl triamide. Examples of the basic compound while can be used as the dehydrohalogenating agents are sodium hydroxide, potassium hydroxide, sodium carbonate, potassium carbonate, sodium methoxide, sodium ethoxide, potassium ethoxide, sodium hydride, potassium metal, sodium amide; and a tertiary amine such as pyridine, quinoline, triethylamine or tripropylamine. In the above reaction, an alkali metal iodide such as potassium iodide, or sodium iodide can be used as a reaction accelerator. The amount of a compound represented by the general formula (10) to a compound represented by the general formula (11) used in the above reaction is not specifically restricted, but it is desirable that the latter is used in equimolar quantity or more, usually 1 to 1.5 times, preferably 1 to 1.2 times the molar quantity of the former. A compound represented by the general formula (2) which is used as the starting material in the present invention can thus be obtained.

In the reaction process formulas-3 and -4, among compounds represented by the general formulas (6), (8) and (10), which are the starting materials used in the reactions, those having substituted groups wherein $R^1$ is an alkyl group having 1 to 6 carbon atoms, an alkenyl group having 2 to 4 carbon atoms, an alkynyl group having 2 to 4 carbon atoms, or a phenylalkyl group of which the alkyl group has 1 to 4 carbon atoms include novel compounds. Said compounds can easily be prepared by using a known hydroxycarbostyril, in which R[1] is hydrogen atom, as the starting material and reacting it with an alkylhalide, an alkenyl halide, an alkynyl halide or a phenylalkyl halide in the presence of a basic compound such as an alkali metal, for example sodium metal or potassium metal; an alkali metal amide such as sodium amide or potassium amide, or sodium hydride, in a suitable solvent such as benzene, tetrahydrofuran, dioxane, dimethyl sulfoxide, dimethylformamide, hexamethylphosphoryl triamide, at a temperature of 0° to 70° C., preferably at 0° to room temperature, for 30 minutes to 12 hours, then hydrolyzing the thus formed compound under a condition similar to that of hydrolysis of a compound represented by the general formula (9) wherein the alkyl group has 1 to 4 carbon atoms, as shown in reaction process formula-3. In the above reaction, the amount of the basic compound, i.e., alkyl halide, alkenyl halide, alkynyl halide or phenylalkyl halide to the starting material can be suitably selected from a wide range, but is usually used in an amount of 2 to 10 times the moles, preferably 2 to 4 times the moles, of the starting material.

The desired compound represented by the general formula (1) can thus be prepared.

Among the desired compounds represented by the general formula (1), a compound represented by the general formula (1d), in which l and m are respectively 1 and R[3] is hydroxy group, can be prepared by the following reaction process formula-5.

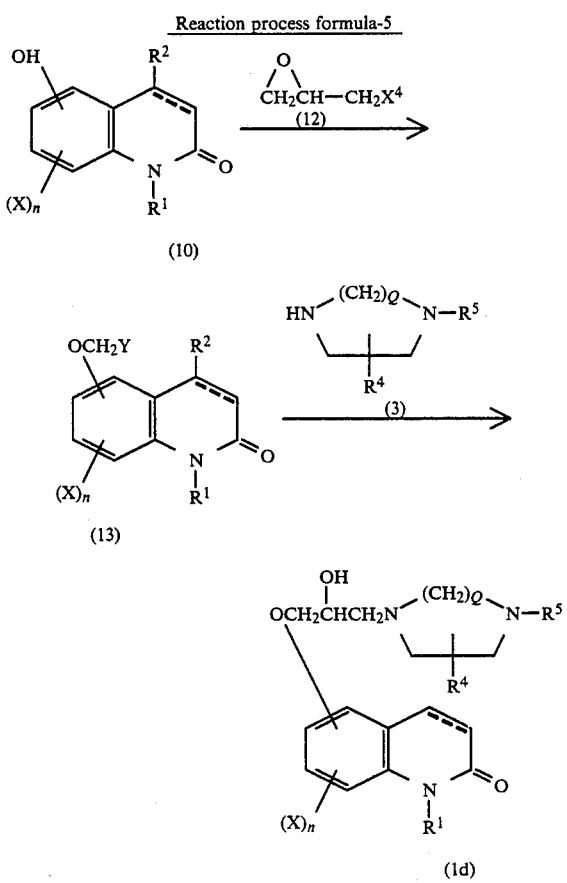

wherein R[1], R[2], R[4], R[5], X, n Q, the carbon-carbon bond at the 3- and 4-position in the carbostyril skeleton and the substituted position of the hydroxy group are all the same as defined above, X[4] is a halogen atom, Y is

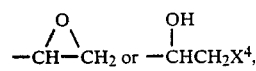

and the substituted positions of the side chains of

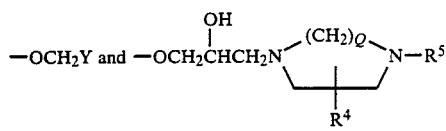

are any one of the 4-, 5-, 6-, 7- or 8-positions in the carbostyril skeleton.

In the reaction process formula-5, the reaction of a hydroxycarbostyril derivative represented by the general formula (10) with an epihalogenohydrin represented by the general formula (12) can be carried out in the presence of a suitable basic compound, for example, an inorganic basic compound, such as sodium hydroxide, potassium hydroxide, sodium carbonate, potassium carbonate, sodium methoxide, sodium ethoxide, sodium hydride, sodium metal, potassium metal, and sodium amide, or an organic basic compound such as piperidine, pyridine, and triethylamine, in the absence or in the presence of a solvent, for example, a lower alcohol such as methanol, ethanol, isopropanol; a ketone such as acetone or methyl ethyl ketone; an ether such as ether, dioxane, diethylene glycol dimethyl ether; an aromatic hydrocarbon such as benzene, toluene xylene; or water. In this reaction, the amount of a compound represented by the general formula (12) used can suitably from a wide range, but usually is used in an equimolar quantity or more, preferably 5 to 10 times the molar quantity of the compound represented by the general formula (10). The reaction can proceed at a temperature between 0° and 150° C., preferably from 50° to 100° C. In the above reaction, an epihalogenohydrin represented by the general formula (12) reacts with a hydroxy group of the compound represented by the general formula (10) to give compounds having a (2,3-epoxy)propoxy group or a 3-halogeno-2-hydroxypropoxy group. Generally, the reaction product can be obtained as a mixture of these compounds.

The thus-obtained reaction product can be reacted with an amine represented by the formula (3) as it is, without any separation or purification procedure. Further, the reaction product can be reacted with an amine represented by the formula (3) after the product is purified by applying a usual separation procedure such as recrystallization or column chromatography, to obtain a purified compound having a 2,3-epoxypropoxy group or a 3-halogeno-2-hydroxypropoxy group respectively.

The reaction of a compound represented by the general formula (13) with a compound represented by the general formula (3) can be carried out in the absence or in the presence of an inert solvent usually used, at a temperature ranging from room temperature to 200° C., preferably 60° to 120° C., and the reaction is completed within a period of several hours to 24 hours. In the above reaction, the examples of the inert solvent include ethers such as dioxane, tetrahydrofuran, ethylene glycol and dimethylether; aromatic hydrocarbons such as benzene, toluene and xylene; lower alcohols such as methanol, ethanol, isopropanol; polar solvents such as dimethylformamide and dimethylsulfoxide.

Further, in the above reaction, a usual basic compound can be added. The examples of such basic compounds include inorganic basic compounds, such as potassium carbonate, sodium carbonate, sodium hydroxide, sodium hydrogencarbonate and sodium amide; and tertiary amines, such as triethylamine, tripropylamine, pyridine and quinoline. The amount of the respective compounds to be reacted can suitably be selected from a wide range, but usually is is desirabkle that the compound represented by the general formula (3) is used in an equimolar quantity or an excess amount, preferably, an equimolar quantity to 5 times the molar quantity, more preferably, 1 to 1.2 times the molar quantity of the compound represented by the general formula (13).

Among the desired compound represented by the general formula (1), a compound represented by the general formula (1f) in which $R^1$ is an alkyl group having 1 to 6 carbon atoms, an alkenyl group having 2 to 4 carbon atoms or, a phenylalkyl group in which the alkylene group has 1 to 4 carbon atoms can be prepared by reacting a compound wherein $R^1$ is a hydrogen atom with a halogen compound represented by the general formula (14) as explained in reaction process formula-6 as follows:

Reaction process formula-6

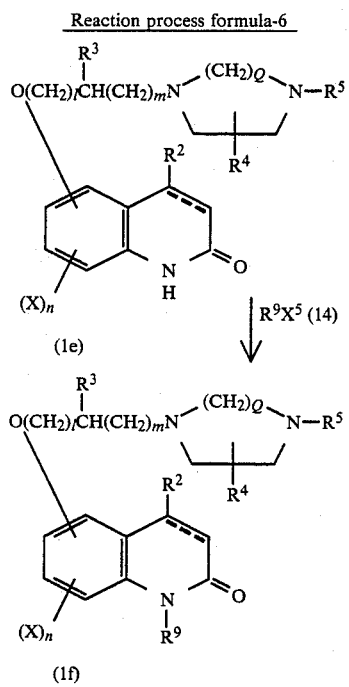

wherein $R^2$, $R^3$, $R^4$, $R^5$, X, l, m, n, Q, the carbon-carbon bond at the 3- and 4-positions in the carbostyril skeleton and the substituted position of the side chain of

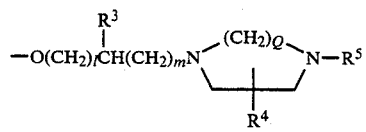

are all the same as defined above, $R^9$ is an alkyl group having 1 to 6 carbon atoms, an alkenyl group having 2 to 4 carbon atoms, an alkynyl group having 2 to 4 carbon atoms; or a phenylalkyl group wherein the alkylene group has 1 to 4 carbon atoms, and X is a halogen atom.

In the reaction of a compound represented by the general formula (1e) with a compound represented by the general formula (14), the amount of the latter is from an equimolar quantity to 3 times the molar quantity of the former, preferably an equimolar quantity of the former. The same reaction conditions for reacting a compound [wherein $R^1$, as defined in the general formulas (6), (8) or (10), is a hydrogen atom], with an alkyl halide, an alkenyl halide, an alkynyl halide or a phenylalkylhalide can also be applied.

The desired compound represented by the general formula (1) of the present invention can also be prepared by the reaction process formula-7. Thus a compound represented by the general formula (1) can be prepared by reacting a compound represented by the general formula (10) with a compound represented by the general formula (15) in accordance with a known method or an analogous method.

Reaction process formula-7

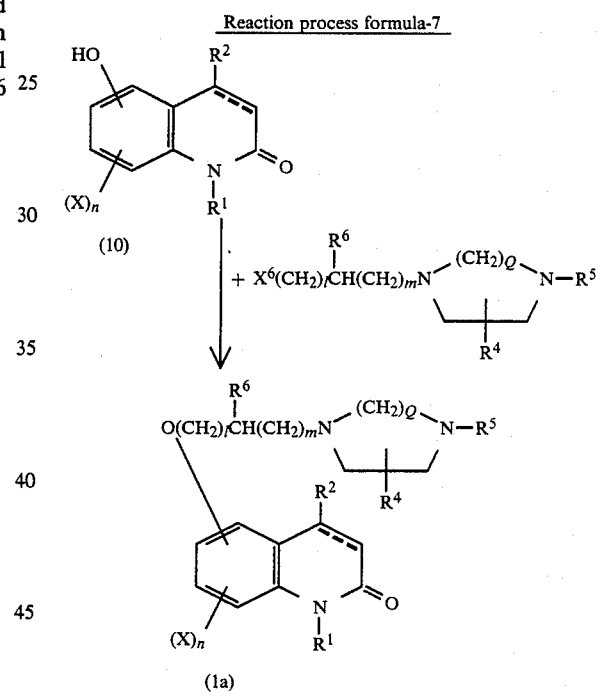

wherein $R^1$, $R^2$, $R^6$, $R^4$, $R^5$, X, l, m, n, Q, the carbon-carbon bond at the 3- and 4-positions in the carbostyril skeleton, the substituted position of hydroxy group and the substituted position of the side chain of

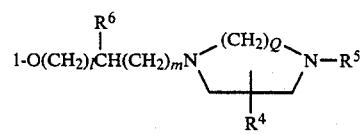

are all the same as defined above, $X^6$ is a halogen atom or a group which may act in a substitution reaction similarly to the halogen atom, such as mesityloxy or tosyloxy group. When l is 1, then $X^6$ and $R^3$ may form an epoxy ring through the oxygen atom.

In the reaction process formula-7, a compound of the general formula (1) of the present invention can be prepared by reacting a compound of the general formula (10) with a compound of the general formula (15) which can easily be prepared by known processes or by a process analogous to known processes. In carrying out the reaction of a compound of the general formula (10) with a compound of the general formula (15), the reaction conditions in the reaction of a compound of the general formula (10) and a compound of the general formula (11) as shown in the reaction process formula-4 can be applied thereto. Furthermore, in carrying out the reaction of a compound of the general formula (15) in which $X^6$ and $R^3$ form an epoxy group through the oxygen atom, with a compound of the general formula (10), the reaction conditions in the reaction of a compound of the general formula (10) with a compound of the general formula (12) as shown in the reaction process formula-5 can also be applied thereto. In these instances, a compound of the general formula (15) is used at least in an equimolar amount relative to a compound of the general formula (10), and preferably in an amount ranging from equimolar to 3 times the molar quantity of the latter.

a halogen atom respectively; $R^{10}$ is a $C_{1-4}$-alkyl group having one substituted group, such as hydroxy group, phenyl group or a $C_{1-4}$-alkanoyloxy group, or a $C_{3-8}$-cycloalkyl group; $R^{11}$ is a $C_{1-4}$ alkanoyl group or a benzoyl group; $R^{12}$ is a halogen atom, a $C_{1-4}$ alkyl group or a $C_{1-4}$ alkoxy group; q is 0 or an integer of 1 or 2.

In the reaction process formula-8, the starting material of the general formula (16) can easily be obtained by reacting a compound [corresponding to the general formula (3) in which $R^5$ is hydrogen atom] with a compound of the general formula (2) as shown in the reaction process formula-1. Furthermore, a compound of the general formula (16) can also be prepared by catalytically reducing to debenzylate a compound corresponding to the general formula (1) in which $R^5$ is benzyl group.

The debenzylation reaction can be carried out under conditions similar to those used in the usual catalytic reduction. Thus the reaction can be carried out in an inert solvent. The examples of such solvent include water, a lower alcohol such as methanol, ethanol or Reaction process formula-8

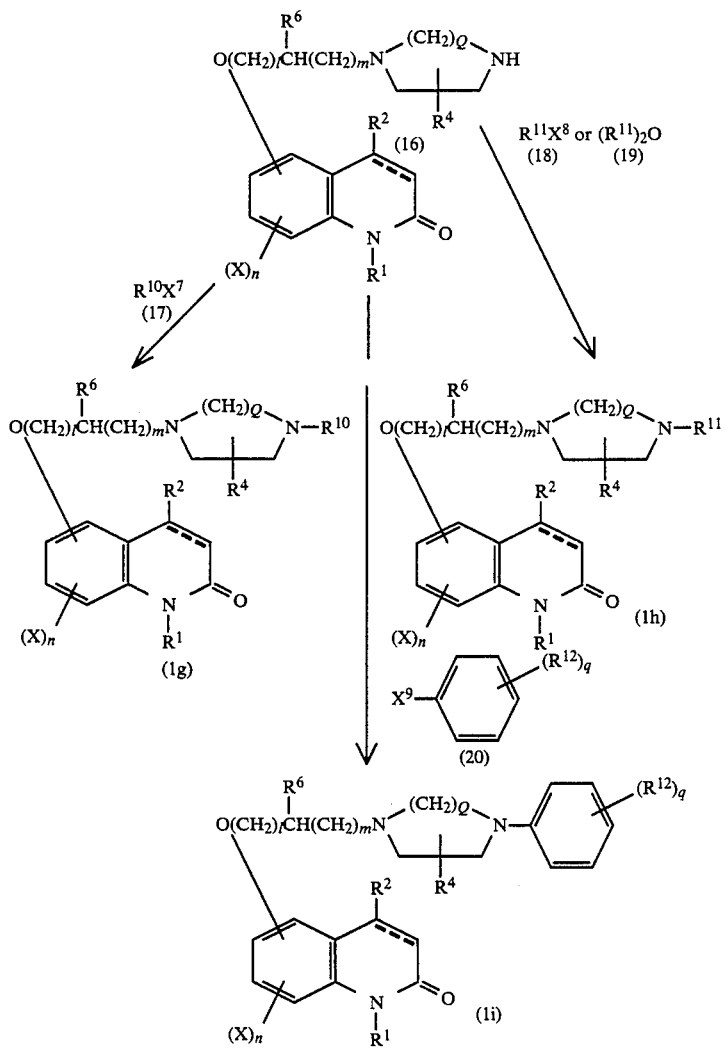

wherein $R^1$, $R^2$, $R^3$, $R^4$, $R^6$, X, l, m, n, Q, the carbon-carbon bond at the 3- and 4-positions in the carbostyril skeleton and the substituted position of the side chain are all the same as defined above; $X^7$, $X^8$ and $X^9$ are each isopropanol, ethyl acetate, acetic acid, toluene, xylene or the like. The examples of catalyst used in the reaction include palladium charcoal, palladium black, platinum, Raney nickel or the like. The debenzylation reaction is carried out under a pressure of 1 to 30 atms., preferably, 1 to 3 atms. at a temperature ranging from room temperature to 100° C., preferably from room temperature to 60° C., for 30 minutes to 6 hours. In the reaction of a compound of the general formula (16) with a known compound of general formula (17), the same reaction conditions in reacting a compound of the general formula (2) with a compound of the general formula (3) can be applied. Furthermore, in the reaction of a compound of the general formula (16) with a known compound of the general formula (18), the same reaction conditions in the reaction of a compound of the general formula (1b) with a compound of the general formula (4) or (5) as shown in the reaction process formula-2 can be applied.

The reaction of a compound of the general formula (16) with a compound of the general formula (20) is carried out in the absence or presence of a basic condensing agent, in a suitable inert solvent. Examples of such an inert solvent include an aromatic hydrocarbon such as benzene, toluene or xylene or the like; a lower alcohol such as methanol, ethanol, propanol, butanol or the like; pyridine, acetone, dimethylsulfoxide, dimethylformamide or hexamethylphosphoryl triamide or the like. The examples of a basic condensing agent include sodium carbonate, potassium carbonate, sodium hydrogen carbonate, potassium hydrogencarbonate, sodium hydroxide, potassium hydroxide, sodium hydride, potassium hydride, triethylamine or the like.

The amount of a compound of the general formula (20) used is at least an equimolar amount relative to a compound of the general formula (16), preferably equimolar to 3 times the molar quantity of the latter. The reaction can be conducted at a temperature ranging from room temperature to 180° C., preferably at 100° to 150° C., for 3 to 30 hours.

Reaction process formula-9

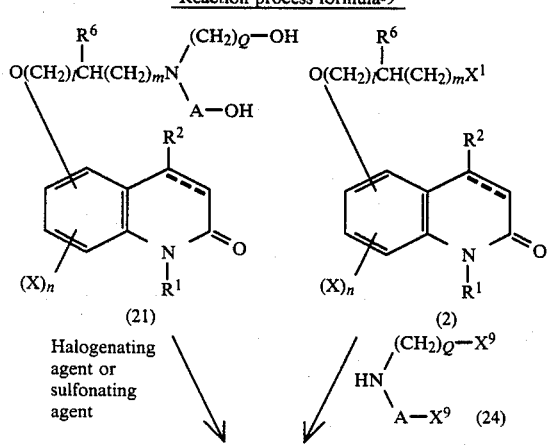

-continued
Reaction process formula-9

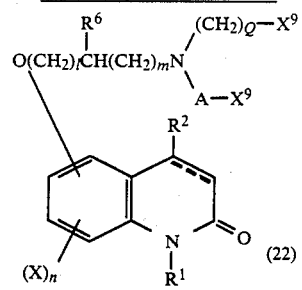

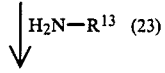

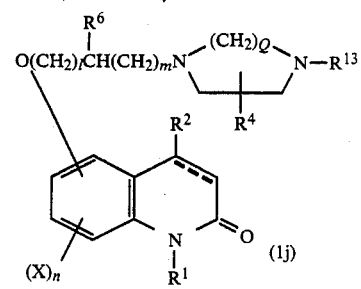

wherein $R^1$, $R^2$, $R^4$, $R^6$, X, l, m, n, Q, the carbon-carbon bond at the 3- and 4-positions in the carbostyril skeleton and the substituted position of the side chain are all the same as defined above, A is an ethylene group which may have one $C_{1-4}$ alkyl group as a substituted group; $X^9$ is a halogen atom or a group such as mesityl or tosyl group which can undergo a substitution reaction similar to that of a halogen atom; $R^{13}$ is a $C_{3-8}$-cycloalkyl group, a phenyl group which may have 1 to 3 substituted groups selected from the group consisting of a halogen atom, a $C_{1-4}$-alkyl group and a $C_{1-4}$ alkoxy group, or a $C_{1-4}$-alkyl group having one $C_{1-4}$ alkanoyloxy group.

As shown in the reaction process formula-9, a compound of the general formula (22) is prepared by reacting a compound of the general formula (21) with a halogenating agent or a sulfonated esterification agent, and by reacting a compound of the general formula (2) with a compound of the general formula (24). A compound of the general formula (21) is prepared by reacting a compound of the general formula (2) with a compound represented by the general formula

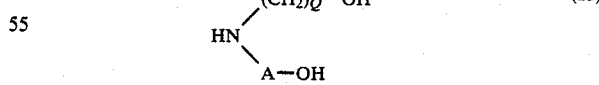

[wherein Q and A are the same as defined above]. More particularly, the reaction of a compound of the general formula (2) with a compound of the general formula (24) or (25), which is prepared by a known or analogous process, can be carried out under the same reaction conditions as the reaction of a compound of the general formula (2) with a compound of the general formula (3).

The reaction of a compound of the general formula (21) with a halogenating agent is carried out in a suitable inert solvent. Examples of such solvents include an ether such as dioxane or tetrahydrofuran; a halogenated hydrocarbon such as chloroform or methylene chloride. Examples of such halogenating agents include N,N-diethyl-1,2,2-trichlorovinylamide, phosphorus pentachloride, phosphorus pentabromide, phosphorus oxychloride or the like.

The amount of a halogenating agent used is at least 2 times the molar quantity of a compound of the general formula (21) and usually is an excess amount. The reaction is carried out at a temperature ranging from room temperature to 100° C., preferably, at 40° to 70° C., for 1 to 6 hours.

The reaction of a compound of the general formula (21) with a sulfonated esterification agent is carried out in the presence of a basic condensing agent in a suitable inert solvent. The examples of such inert solvents include aromatic hydrocarbons, such as benzene, toluene or the like, an ether such as dioxane, tetrahydrofuran or the like, pyridine, dimethylsulfoxide, dimethylformamide, or hexamethylphosphoryl triamide. Examples of such sulfonated esterifying agents include an alkane sulfonyl halide such as mesityl chloride, mesityl bromide, tosyl chloride or the like, or alkyl sulfonyl halide.

Examples of such condensing agents include a tertiary amine such as triethylamine, pyridine or N,N-dimethylaniline, sodium hydrogen carbonate, potassium hydrogen carbonate, sodium carbonate, or potassium carbonate.

The amount of sulfonated esterifying agent used is at least 2 times the molar quantity of a compound of the general formula (21), preferably 2 to 4 times the molar quantity. The reaction is carried out at $-30°$ to $100°$ C., preferably at $0°$ to $50°$ C., for 1 to 15 hours.

The reaction of a compound of the general formula (22) with a compound of the general formula (23) is carried out in the presence or absence of a basic condensing agent in a suitable inert solvent. Examples of such inert solvents include a lower alcohol, for example, methanol, ethanol, isopropanol, butanol or the like, an aromatic hydrocarbon, for example, benzene, toluene xylene or the like, acetic acid, ethyl acetate, dimethylsulfoxide, dimethylformamide, hexamethylphosphoryl triamide or the like. Examples of the basic condensing agent include sodium carbonate, potassium carbonate, sodium hydrogencarbonate, sodium hydroxide, potassium hydroxide, sodium methylate, sodium ethylate, pyridine, triethylamine or the like.

The amount of a compound of the general formula (23) used is at least an equimolar quantity relative to a compound of the general formula (22), preferably an equimolar to 5 times the molar quantity of the latter.

The reaction is carried out at 40° to 120° C., preferably at 70° to 100° C., for 1 to 15 hours.

Reaction process formula-10

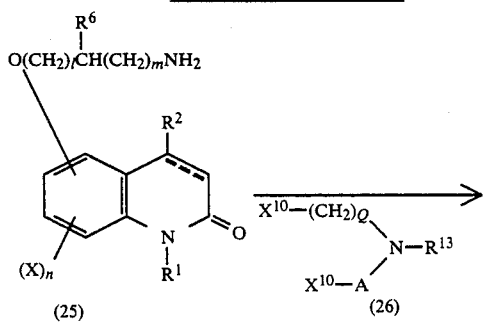

(25)

(26)

Reaction process formula-10

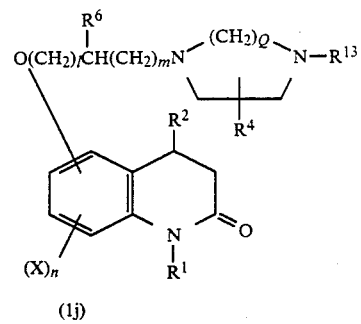

(1j)

wherein $R^1$, $R^2$, $R^4$, $R^6$, X, l, m, n, Q, A, the carbon-carbon bond at the 3- and 4-positions in the carbostyril skeleton and the unsubstituted position of the side chain are all the same as defined above, $X^{10}$ is a halogen atom or a group such as mesityloxy or tosyloxy which can undergo a substitution reaction similar to that of the halogen atom.

The compounds of the general formula (25) and (26) can be prepared by known processes or analogous processes.

In the reaction of a compound of the general formula (25) with a compound of the general formula (26), the reaction conditions can be those of the reaction of a compound of the general formula (22) with a compound of the general formula (23) as shown in the reaction process formula-9.

If necessary, compounds of the general formulas (1a), (1g), (1h), (1i) and (1j) which are prepared by the procedures shown in the reaction process formulas-7 to 10 can be converted into the corresponding ester forms by alkanoylating or 3,4,5-trimethoxybenzoylating a compound corresponding thereto respectively in which $R^6$ is hydroxy group by a procedure as mentioned in the reaction process formula-2.

Furthermore, among carbostyril compounds of the general formula (1) of the present invention, a compound wherein the carbon-carbon bond at the 3- and 4-positions in the carbostyril skeleton is a single bond can be converted into a compound of which the carbon-carbon bond at 3- and 4-positions is a double bond by dehydrating the former.

Alternatively, among carbostyril compounds of the general formula (1) of the present invention, a compound wherein the carbon-carbon bond at the 3- and 4-positions in the carbostyril skeleton is a double bond can be converted into a compound wherein the carbon-carbon bond at the 3- and 4-position is a single bond and also without having halogen atoms, alkenyl groups and alkynyl groups, by catalytically reducing the former.

Compounds of the general formula (1) in the present invention can easily be converted into their acid-addition salts by reacting with pharmaceutically acceptable acids. Examples of such acids include inorganic acids, such as hydrochloric acid, sulfuric acid, phosphoric acid, hydrobromic acid and the like; and organic acids such as oxalic acid, maleic acid, fumaric acid, malic acid, tartaric acid, citric acid, benzoic acid and the like. The desired compounds as prepared by the procedures in the above-mentioned various reaction process formulas can easily be isolated and purified by the usual separation means such as solvent extraction, dilution, recrystallization, column chromatography and preparative thin-layer chromatography.

Compounds of the present invention also include their optical isomers.

As for antihistaminic agents and central nervous controlling agents, compounds of the general formula (I) can be used in the form of pharmaceutical compositions together with the usual pharmaceutically acceptable carriers. Examples of the carriers which are used depending on the desired form of pharmaceutical composition include diluents or excipients such as fillers, diluents, binders, wetting agents, disintegrators, surface-active agents, and lubricants.

No particular restriction applies to administration unit forms, and the compounds can be used in any desired unit form as antihistaminic agents and central nervous controlling agents, Typical unit forms include tablets, pills, powders, liquors, suspensions, emulsions, granules, capsules, suppositories, injections (solutions and suspensions) and ointments. The compounds can be combined with carriers which are widely used in this field to form tablets. Examples of carriers include excipients such as lactose, sucrose, sodium chloride, solutions of glucose, urea, starch, calcium carbonate, kaolin, crystalline cellulose, and silicic acid; binding agents, such as water, ethanol, propanol, simple syrup, glucose, starch solution, gelatin solution, carboxymethyl cellulose, shellac, methyl cellulose, calcium phosphate and polyvinylpyrrolidone; disintegrators such as dried starch, sodium alginate, agar-agar powder, laminalia powder, sodium hydrogencarbonate, calcium carbonate, Tweens, sodium laurylsulfate, monoglyceride of stearic acid, starch, and lactose; disintegration inhibitors such as sucrose, stearin, coconut butter, hydrogenated oil; absorption accelerators such as quarternary ammonium base, and sodium laurylsulfate; wetting agents such as glycerin or starch; adsorbing agents, such as starch, lactose, kaoline, bentonite, and colloidal silicic acid; and lubricants such as purified talc, steric acid salt, boric acid powder, Macrogol, and solid polyethylene glycol.

Carriers which are known and widely used in this field can also be used, for example, excipients, such as glucose, lactose, starch, coconut butter, hydrogenated vegetable oils, kaolin and talc; binder, such as powdered Gummi Arabicum, powdered Tragacanth, gelatin and ethanol; and disintegrators such as laminaria and agar-agar. If tablets are desired, they can be further coated with the usual coating materials to make sugar coated tablets, gelatin film coated tablets, tablets coated with enteric coatings, tablets coated with films, double layered tablets and multi-layered tablets.

Suppositories are desired carriers which are known and widely used in this field and can also be used, such as, for example, polyethylene glycols, coconut butter, higher alcohols, esters of higher alcohols, gelatin and semi-synthesized glycerides.

If injection preparations are desired, solutions and suspensions can be sterilized and are preferably isotonic to blood. In making injection preparations, carriers which are commonly used in this field can also be used, such as water, ethyl alcohol, propylene glycol, ethoxylated isostearyl alcohol, polyoxylated isostearyl alcohol, polyoxyethylene sorbitol, and sorbitane esters. In these instances, adequate amounts of sodium chloride, glucose or glycerin can be added to the desired preparations to make them isotonic. Furthermore, the usual dissolving agents, buffers, analgesic agents, and preservatives can be added. Moreover, coloring materials, preservatives, perfumes, seasoning agents, sweetening agents and other medicines can also be added.

For the purpose of making preparations in the form of pastes and creams, diluents which are known and widely used in this field can also be used, such as, white vaseline, paraffin, glycerin, cellulose derivatives, polyethylene glycols, silicones and bentonite.

The amount of compounds of the general formula (I) or their acid addition salts to be contained in the antihistaminic agents and central nervous controlling agents is not especially restricted and can suitably be selected from a wide range, but usually 1 to 70% by weight of the whole composition is preferable.

The above-mentioned antihistaminic agents and central nervous controlling agents can be used in various forms depending on the purpose without any restriction. For example, tablets, pills, solutions, suspensions, emulsions, granules and capsules are administered orally; and injection preparations are administered intravenously singly or are mixed with injection transfusions such as glucose solutions and amino acid solutions; if necessary, the injection preparations are administered singly intramuscularly, intracutaneously, subcutaneously or intraperitoneally. Suppositories are administered into the rectum and ointments are administered by coating.

The dosage of the present antihistaminic agents and central nervous controlling agents are suitably selected according to the usage, purpose and conditions of symptoms and usually a pharmaceutical composition containing 40 µg-2 mg/kg.day of the compound of the general formula (I) or its acid addition salt may be administered 3-4 times a day.

| Example of preparation of tablet-1 | |
|---|---|
| 7-[3-(4-Phenylpiperazinyl)propoxy]-3,4-dihydrocarbostyril.dihydrochloride | 5 mg |
| Corn starch | 132 mg |
| Magnesium stearate | 18 mg |
| Lactose | 45 mg |
| Total | 200 mg |
| Example of preparation of tablet-2 | |
| 7-[3-(4-Phenylpiperazinyl)propoxy]-3,4-dihydrocarbostyril.dihydrochloride | 10 mg |
| Corn starch | 130 mg |
| Magnesium stearate | 18 mg |
| Lactose | 42 mg |
| Total | 200 mg |

By using the usual procedures, tablets having the above formulations are prepared.

The results of pharmacological tests on the compounds of the present invention are shown below.

(I) Antihistamine activity test

As to the test method for determining antihistamine activity of a compound in vitro, a method of using an enucleated ileum of a guinea pig is generally accepted.

A male guinea pig having 300 to 500 g body weight is killed by blood letting. An ileum having a length of 15 cm and enucleated from the ileocecal region is dipped into Tyrode's solution (which is prepared from 0.8 g of NaCl, 0.2 g of KCl, 0.2 g of $CaCl_2$, 1.0 g of glucose, 1.0 g of $NaHCO_3$, 0.065 g of $NaHPO_4.2H_2O$ and 0.2135 g of $MgCl_2.6H_2O$ to make 1000 ml in total volume by adding water). Then the tissue of ileum is cut to a length of 2.5 to 3.0 cm and suspended in an organ bath filled with 30 ml of Tyrode's solution. The organ bath is kept at a temperature of 36° C. and a mixed gas consisting of 5% of $CO_2$ and 95% of $O_2$ is blown into the bath. 10 Minutes after the blowing, $10^{-6}M$ of histamine is added to the bath to examine the sensitivity of the tissue and a reaction curve (control) with respect to the dosage of histamine is obtained. After the dosage of histamine-reaction curve (control) becomes constant, $10^{-6}$ g/ml of a compound to be tested is added to the bath and further histamine is added 5 minutes later to obtain a dosage-reaction curve. Retraction of the ileum is recorded on a pen-recorder through an isotonic transducer [TD-112S manufactured by Nihon Koden]. Antihistamine activity of the test compound is determined as $pA_2$ value by the "Van Rossam" method [J. M. Van Rossam: Arch. Inst. Pharmacodyn., 143, 299 (1963)] wherein the maximum retraction of ileum caused by histamine shown in the control curve is 100%. The results are shown in Table 1.

Tested Compounds
[Compounds of the present invention (Nos. 1–39)]

| Compound No. | Name of the compounds |
|---|---|
| 1 | 5-[2-Hydroxy-3-(4-phenylpiperazinyl)propoxy]-3,4-dihydrocarbostyril monohydrochloride |
| 2 | 7-[2-Hydroxy-3-(4-phenylpiperazinyl)propoxy]-3,4-dihydrocarbostyril monohydrochloride |
| 3 | 8-Chloro-5-{2-hydroxy-3-[4-(4-chlorophenyl)piperazinyl]propoxy}-3,4-dihydrocarbostyril monohydrochloride |
| 4 | 6,8-Dichloro-5-[2-hydroxy-3-(4-phenylpiperazinyl)propoxy]-3,4-dihydrocarbostyril monohydrochloride |
| 5 | 5-[3-(4-Phenylpiperazinyl)propoxy]-3,4-dihydrocarbostyril dihydrochloride |
| 6 | 7-[3-(4-Phenylpiperazinyl)propoxy]-3,4-dihydrocarbostyril dihydrochloride |
| 7 | 1-Methyl-5-[2-hydroxy-3-(4-phenylpiperazinyl)propoxy-3,4-dihydrocarbostyril monohydrochloride |
| 8 | 1-Benzyl-5-[2-hydroxy-3-(4-phenylpiperazinyl)propoxy]-3,4-dihydrocarbostyril monohydrochloride |
| 9 | 1-Methyl-5-[3-(4-phenylpiperazinyl)propoxy]-3,4-dihydrocarbostyril monohydrochloride |
| 10 | 5-4-[4-(4-Methylphenyl)piperazinyl]butoxy-3,4-dihydrocarbostyril |
| 11 | 1-Allyl-5-{2-hydroxy-3-[4-(4-methylphenyl)piperazinyl]propoxy}-3,4-dihydrocarbostyril |
| 12 | 1-Benzyl-7-[3-(4-phenylpiperazinyl)propoxy]-3,4-dihydrocarbostyril |
| 13 | 4-Methyl-7-[3-(4-phenylpiperazinyl)propoxy]-carbostyril |
| 14 | 7-[3-(4-Benzylpiperazinyl)propoxy]-3,4-dihydrocarbostyril |
| 15 | 7-{3-[4-(4-Methylphenyl)piperazinyl]propoxy}-3,4-dihydrocarbostyril |
| 16 | 7-{3-[4-(4-Chlorophenyl)piperazinyl]propoxy}-3,4-dihydrocarbostyril |
| 17 | 7-{3-[4-(2-Methoxyphenyl)piperazinyl]propoxy}-3,4-dihydrocarbostyril |
| 18 | 7-{3-[3-Methyl-4-(4-chlorophenyl)piperazinyl]propoxy}-3,4-dihydrocarbostyril dihydrochloride |
| 19 | 8-[3-(4-Phenylpiperazinyl)propoxy]-3,4-dihydrocarbostyril |
| 20 | 5-[2-Acetyloxy-3-(4-phenylpiperazinyl)propoxy]-3,4-dihydrocarbostyril |
| 21 | 5-[2-(3,4,5-Trimethoxybenzoyloxy)-3-(4-phenylpiperazinyl)propoxy]-3,4-dihydrocarbostyril |
| 22 | 7-3-[4-(2-Methoxyphenyl)piperazinyl]-propoxy-carbostyril dihydrochloride |
| 23 | 1-(2-Propyl)-7-[3-(4-phenylpiperazinyl)propoxy]-3,4-dihydrocarbostyril dihydrochloride |
| 24 | 7-{3-[4-(3-Fluorophenyl)piperazinyl]propoxy}-3,4-dihydrocarbostyril |
| 25 | 7-[2-Methyl-3-(4-phenylpiperazinyl)propoxy]-3,4-dihydrocarbostyril |
| 26 | 4-[3-(4-Phenylpiperazinyl)propoxy]carbostyril |
| 27 | 4-Phenyl-7-[3-(4-phenylpiperazinyl)propoxy]-carbostyril |
| 28 | 6-Chloro-8-bromo-7-[3-(4-phenylpiperazinyl)-propoxy]-3,4-dihydrocarbostyril dihydrochloride |
| 29 | 7-{3-[4-(3,4,5-Trimethoxyphenyl)piperazinyl]-propoxy}-3,4-dihydrocarbostyril dihydrochloride |
| 30 | 5-[3-(4-Cyclohexylpiperazinyl)propoxy]-3,4-dihydrocarbostyril |
| 31 | 5-[3-(4-Phenylhomopiperazinyl)propoxy]-3,4-dihydrocarbostyril |
| 32 | 7-{3-[4-(2-Acetyloxyethyl)piperazinyl]propoxy}-3,4-dihydrocarbostyril |
| 33 | 7-{3-[4-(2-Hydroxyethyl)piperazinyl]propoxy}-3,4-dihydrocarbostyril |
| 34 | 7-[3-(4-Acetylpiperazinyl)propoxy]-3,4-dihydrocarbostyril |
| 35 | 7-[3-(4-Benzoylpiperazinyl)propoxy]-3,4-dihydrocarbostyril |
| 36 | 6-[3-(4-Phenylpiperazinyl)propoxy]carbostyril |
| 37 | 7-[3-(4-Phenylpiperazinyl)propoxy]carbostyril |
| 38 | 1-Hexyl-7-[3-(4-phenylpiperazinyl)propoxy)]-3,4-dihydrocarbostyril dihydrochloride |
| 39 | 7-{3-[4-(3-Chlorophenyl)piperazinyl]propoxy}-3,4-dihydrocarbostyril |

TABLE 1

| Tested Compound No. | $pA_2$ |
|---|---|
| 1 | 8.08 |
| 2 | 7.75 |
| 3 | 8.31 |
| 4 | 8.95 |
| 5 | 8.87 |
| 6 | 9.34 |
| 7 | 9.88 |
| 8 | 10.80 |
| 9 | 10.58 |
| 10 | 8.90 |
| 11 | 9.21 |
| 12 | 8.21 |
| 13 | 9.39 |
| 14 | 9.10 |
| 15 | 9.48 |
| 16 | 9.63 |
| 17 | 9.06 |
| 18 | 8.66 |
| 19 | 7.99 |
| 20 | 8.91 |
| 21 | 9.04 |
| 22 | 7.93 |
| 23 | 9.23 |
| 24 | 9.59 |
| 25 | 9.21 |
| 26 | 8.66 |
| 27 | 9.01 |
| 28 | 9.64 |
| 29 | 8.57 |
| 30 | 7.35 |
| 31 | 9.58 |
| 32 | 7.52 |
| 33 | 7.02 |
| 34 | 7.24 |
| 35 | 8.58 |
| 36 | 7.99 |
| 37 | 9.53 |
| 38 | 8.93 |
| 39 | 9.74 |

(II) Anesthesia and sleep increasing activity (A) Halothane anesthesia increasing activity Male mice of ddy-strain having about 20 g body weight are used. One test group consists of 10 mice. An aqueous Gummi Arabicum suspension of test compound (80 mg of a compound to be tested and 1 g of Gummi Arabicum/100 ml of physiological NaCl solution) is administered orally to each mouse at the dosage of 8 mg of test compound/kg body. One hour after the administration, each mouse is placed in a gas respiration chamber (13×13×24 cm) and oxygen gas containing 4% of Halothane [2-bromo-2-chloro-1,1,1-trifluoroethane] is blown into the chamber at the velocity of 2 l/min for 3 minutes. A mouse anaesthetized is taken out from the chamber and the time between the introduction of anesthesia to waking is measured by righting reflex as the index. To mice of the control group, 1% Gummi Arabicum aqueous physiological solution is orally administered at the dosage of 0.1 ml/10 g body. [Reference: M. J. Turnbull and J. W. Watkins: Br. J. Pharmac., 58, 27–35 (1976)]

The results are shown in Table 2.

TABLE 2

| (Dosage: 8 mg/kg) | |
|---|---|
| Tested Compound No. | Time (minutes) |
| 1 | 9.3 ± 4.9 |
| 2 | 11.7 ± 5.6 |
| 3 | 7.9 ± 3.4 |
| 4 | 7.4 ± 2.7 |
| 5 | 16.9 ± 7.9 |
| 6 | 16.8 ± 6.2 |
| 7 | 8.9 ± 2.4 |
| 8 | 7.5 ± 3.3 |
| 9 | 9.5 ± 3.2 |
| 10 | 7.9 ± 3.7 |
| 11 | 6.8 ± 2.2 |
| 12 | 7.5 ± 3.5 |
| 13 | 8.1 ± 2.7 |
| 14 | 7.5 ± 4.3 |
| 15 | 12.7 ± 3.5 |
| 16 | 11.4 ± 5.6 |
| 17 | 13.6 ± 5.2 |
| 18 | 8.4 ± 2.5 |
| 19 | 9.3 ± 3.5 |
| 20 | 9.8 ± 3.7 |
| 21 | 8.1 ± 3.9 |
| 22 | 10.4 ± 4.1 |
| 23 | 7.6 ± 4.2 |
| 24 | 11.6 ± 6.7 |
| 25 | 7.8 ± 3.3 |
| 26 | 8.5 ± 3.7 |
| 27 | 7.8 ± 3.2 |
| 28 | 10.2 ± 5.8 |
| 29 | 9.3 ± 4.4 |
| 30 | 7.9 ± 3.7 |
| 31 | 8.2 ± 3.9 |
| 32 | 7.9 ± 3.1 |
| 33 | 7.4 ± 2.6 |
| 34 | 7.8 ± 3.4 |
| 35 | 8.2 ± 3.7 |
| 36 | 15.3 ± 3.1 |
| 37 | 13.1 ± 6.0 |
| 39 | 5.0 ± 2.9 |

(B) Halothane anesthesia increasing activity

The same procedures as mentioned in (II)-(A) are employed, except that the amount of test compound to be orally administered is changed in 4 steps at the dosage of 0.5 mg/kg, 1 mg/kg, 2 mg/kg and 4 mg/kg respectively to measure the relationship between the dosage and degree of strength of anesthesia increasing activity.

The results are shown in Table 3.

TABLE 3

| | Anesthesia increasing activity (minutes) | | | | |
|---|---|---|---|---|---|
| Compound tested | 0 mg/kg | 0.5 mg/kg | 1 mg/kg | 2 mg/kg | 4 mg/kg |
| [Reference compound] | | | | | |
| Haloperidol | 5.6 ± 3.1 | 5.3 ± 2.9 | 5.1 ± 2.5 | 9.3 ± 3.1 | 10.2 ± 3.7 |
| Pentobarbital | 5.1 ± 3.5 | 5.3 ± 2.6 | 4.9 ± 3.5 | 6.3 ± 2.3 | 8.1 ± 3.1 |
| [Compound of the present invention] | | | | | |
| Compound No. 5 | 4.9 ± 2.5 | 5.2 ± 2.1 | 8.5 ± 3.5 | 9.6 ± 4.1 | 12.7 ± 3.9 |
| Compound No. 6 | 5.5 ± 2.1 | 8.2 ± 2.6 | 10.3 ± 3.3 | 12.1 ± 4.2 | 16.6 ± 5.1 |
| Compound No. 7 | 4.8 ± 3.1 | 5.3 ± 2.5 | 7.4 ± 3.1 | 9.5 ± 3.8 | 13.7 ± 4.7 |
| Compound No. 29 | 5.1 ± 2.6 | 5.6 ± 2.8 | 6.6 ± 3.1 | 8.3 ± 3.7 | 13.6 ± 4.6 |

(C) Hexabarbital sleep increasing activity

Male mice of ddy-strain having 20 to 25 g body weight are starved for 24 hours. One test group consists of 10 mice. An aqueous Gummi Arabicum suspension of test compound (0.05 g of test compound and 1 g of Gummi Arabicum/100 ml of physiological NaCl solution) is administered orally at the dosage mentioned in the Table 4. One hour after the administration 0.7% of Hexabarbital. Na-salt is intraperitoneally administered at the dosage of 70 mg/kg body weight. The time between the introduction of sleep to waking is measured by righting reflex as the index. [Reference: A. M. Hjort, De E. J. Beer and D. W. Fassett; J. Pharmac. Exptl. Ther., 63, 421 (1963)]

TABLE 4

| Compound tested | Dosage (mg/kg) | Sleep time (min.) [Mean ± SD] |
|---|---|---|
| Compound of the present invention | | |
| Physiological saline solution | — | 36.52 ± 10.15 |
| Compound 6 | 0.5 | 43.76 ± 6.09 |
| Compound 6 | 1.0 | 51.24 ± 11.75 |
| Compound 6 | 2.0 | 54.11 ± 7.80 |
| Compound 6 | 4.0 | 65.13 ± 11.59 |
| Compound 6 | 8.0 | 85.83 ± 12.24 |
| Physiological saline solution | — | 32.14 ± 6.25 |
| Compound No. 17 | 0.125 | 39.51 ± 8.45 |
| Compound No. 17 | 0.25 | 45.57 ± 10.05 |
| Compound No. 17 | 0.5 | 51.77 ± 6.60 |
| Compound No. 17 | 1.0 | 56.92 ± 6.13 |
| Reference known compound | | |
| Physiological saline solution | — | 35.07 ± 4.98 |
| Haloperidol | 4 | 43.01 ± 19.22 |
| Haloperidol | 8 | 46.83 ± 13.94 |
| Haloperidol | 16 | 66.81 ± 14.32 |

(III) Activity for inhibiting fighting behavior of mouse isolated singly for a long period of time Individual male mice of ddy-strain having 15 to 20 g of body weight are breeded separately in respective cages for 1 month. One test group consists of 10 pairs of mice. In each pair, one mouse is taken into the home cage of the other and the two fight together for over 30 seconds continuously. $ED_{50}$ values are calculated by administering the respective test compounds to each test group of mice. Activity for inhibiting fighting behavior of the test compound is determined as positive when the administered mice continue the fighting for no longer than 5 seconds in a minute. When the mice continue the fighting over 5 seconds they are forced to separate for the purpose of reducing injury. [Reference:

C. Y. Yen, R. L. Stanger and N. Millman: Arch. Int. Pharmacodyn., 123, 179 (1959)]

The results are shown in Table 5.

TABLE 5

| Compound tested | ED$_{50}$ (mg/kg) |
| --- | --- |
| The present compound | |
| Compound No. 5 | 1.28 (0.63–2.72) |
| Compound No. 6 | 0.70 (0.51–1.12) |
| Compound No. 9 | 1.52 (0.78–3.53) |
| Compound No. 37 | 0.78 (0.22–1.38) |
| Compound No. 39 | 0.96 (0.52–2.31) |
| Compound No. 17 | 0.92 (0.38–1.59) |
| Reference compound: | |
| Diazepam | 7.29 (4.04–18.6) |

(IV) Analgetic activity

Male mice of ddy-strain having 15–23 g of body weight are used. One test group consists of 10 mice. The compound to be tested is administered orally by procedures similar to the method mentioned in (II). Fifty minutes after the administration, 0.1 ml of 0.6% acetic acid aqueous solution/10 g body weight is injected intraperitoneally. The mice administered orally the reference compound (Haloperidol), the injection is made 110 minutes after the administration. The number of writhings shown after 10 minutes is counted for 10 minutes and the ED$_{50}$ value of respective compounds is calculated in comparison with the number of writhings shown by a control group. [Reference: R. Koster, M. Anderson and E. I. Debeer: Fed. Proc., 18, 412, (1959)]

The results are shown in Table 6

TABLE 6

| Compound tested | ED$_{50}$ (mg/kg) |
| --- | --- |
| The present compound | |
| Compound No. 6 | 2.31 (1.53–3.46) |
| Compound No. 37 | 1.52 (0.71–3.15) |
| Compound No. 31 | 1.92 (1.28–4.31) |
| Reference known compound | |
| Haloperidol | 2.31 (1.26–5.31) |

(V) Acute toxicity test (LD$_{50}$)

Mice of ddy-strain having 20–22 g of body weight are used. One test group consists of 10 mice.

Oral administration:

The compound to be tested is suspended in 1% Gummi

Arabicum physiological NaCl aqueous solution.

Intravenous administration:

The compound to be tested is dissolved in 50% propyleneglycol aqueous solution.

The results are shown in Table 7.

TABLE 7

| | (LD$_{50}$) | | | |
| --- | --- | --- | --- | --- |
| | Male mice | | Female mice | |
| Compound tested | Oral (mg/kg) | Intravenous (mg/kg) | Oral (mg/kg) | Intravenous (mg/kg) |
| The present compound: | | | | |
| Compound No. 6 | 920 | 240 | 890 | 250 |
| Compound No. 7 | 1600 | 424 | 1650 | 432 |
| Compound No. 39 | 1206 | 310 | 1100 | 293 |
| Compound No. 17 | 898 | 218 | 860 | 216 |
| Compound No. 31 | 870 | 256 | 923 | 248 |
| Known compound: | | | | |

TABLE 7-continued

| | (LD$_{50}$) | | | |
| --- | --- | --- | --- | --- |
| | Male mice | | Female mice | |
| Compound tested | Oral (mg/kg) | Intravenous (mg/kg) | Oral (mg/kg) | Intravenous (mg/kg) |
| Diazepam | — | 59 | — | 58 |

LD$_{50}$ value (oral administration) of the present compounds other than compound Nos. 6, 7, 17, 31 and 39 are determined as over 800 mg/kg by using male mice of ddy-strain.

The following reference examples show how to prepare compounds which are used as the starting material in the preparation of the desired compounds of the present invention.

REFERENCE EXAMPLE 1

20.5 grams of 5-acetyloxy-3,4-dihydrocarbostyril are dissolved in 200 ml of acetic acid. This solution is stirred under cooling with water and 60 ml of acetic acid solution containing 16 g of bromine are added dropwise over 30 minutes and the reaction is carried out for 2 hours at the same temperature. The reaction mixture is poured into 300 ml of water and allowed to stand for 3 hours and the crystals thus precipitated are separated by filtration, and recrystallized from methanol to obtain 21 g of 8-bromo5-acetyloxy-3,4-dihydrocarbostyril in the form of colorless needle-like crystals with a melting point of 237°–239° C.

The thus-obtained 21 g of 8-bromo-5-acetyloxy-3,4-dihydrocarbostyril are dispersed in 150 ml of 8N-hydrochloric acid. The dispersion is heated under reflux conditions for 3 hours and then cooled. The insoluble matter thus formed is separated by filtration, washed with water and dried, and recrystallized from methanol-water to obtain 14 g of 8-bromo-5-hydroxy-3,4-dihydrocarbostyril in the form of colorless needle-like crystals with a melting point of 212°–213° C.

REFERENCE EXAMPLE 2

16.4 grams of 5-hydroxy-3,4-dihydrocarbostyril are dissolved in 300 ml of acetic acid. This solution is stirred at room temperature, and 50 ml of acetic acid solution containing 7 g of chlorine are added dropwise and the reaction is continued for 3 hours with stirring. The reaction mixture is poured into 500 ml of water and allowed to stand for 1 hour and the precipitate thus formed is separated by filtration, washed with water and then dried. Recrystallization from ethanol-water obtains 13.5 g of 6-chloro-5-hydroxy-3,4-dihydrocarbostyril in the form of colorless needle-like crystals with a melting point of 209°–210° C.

REFERENCE EXAMPLE 3

16.4 grams of 5-hydroxy-3,4-dihydrocarbostyril are dissolved in 300 ml of acetic acid. This solution is stirred at room temperature, and 80 ml of acetic acid solution containing 16.4 g of chlorine are added dropwise and the reaction is continued for 3 hours with stirring. Similar to the procedure mentioned in REFERENCE EXAMPLE 2, The crude crystals are recrystallized from methanol to obtain 16 g of 6,8-dichloro-5-hydroxy-3,4-dihydrocarbostyril in the form of colorless needle-like crystals with a melting point of 259°–260° C.

REFERENCE EXAMPLE 4

35.4 grams of 7-methoxy-3,4-dihydrocarbostyril are dissolved in 300 ml of acetic acid. This solution is stirred under ice-cooling conditions, and 100 ml of acetic acid solution containing 27 g of sulfuryl chloride are added dropwise and allowed to stand overnight. The reaction mixture is poured into 1 liter of ice-water and the precipitate thus formed is separated by filtration, washed with water and dried. Recrystal-lization from methanol obtains 30 g of 6-chloro-7-methoxy-3,4-dihydrocarbostryil in the form of colorless needle-like crystals with a melting point of 212° C.

The thus-obtained 30 g of 6-chloro-7-methoxy-3,4-dihydrocarbostyril are dispersed in 300 ml of 47%-hydrobromic acid aqueous solution and heated for 4 hours under refluxing condition. After cooling of the reaction mixture, the insoluble matter is separated by filtration, washed with water and dried. Recrystallization from methanol-chloroform obtains 25 g of 6-chloro-7-hydroxy-3,4-dihydrocarbostyril in the form of colorless needle-like crystals with a melting point of 264°–266° C.

REFERENCE EXAMPLE 5

35 grams of 8-methoxy-3,4-dihydrocarbostyril are dissolved in 200 ml of acetic acid. This solution is stirred under cooling and 100 ml of acetic acid solution containing 16 g of chlorine are added and allowed to stand over night. The reaction mixture is poured into 1 liter of water and the precipitate thus formed is separated by filtration, washed with water and dried. Recrystallization from chloroform obtains 42 g of 5,6-dichloro-8-methoxy-3,4-dihydrocarbostyril in the form of pale red needle-like crystals with a melting point of 201°–202° C.

The thus-obtained 42 g of 5,6-dichloro-8-methoxy-3,4-dihydrocarbostyril are dispersed in 500 ml of 47%-hydrobromic acid aqueous solution and heated for 4 hours under refluxing condition. After cooling the reaction mixture, the insoluble matter is separated by filtration, washed with water and dried. The crude crystals thus obtained are recrystallized from methanol to obtain 29 g or 5,6-dichloro-8-hydroxy-3,4-dihydrocarbostyril in the form of colorless needle-like crystals with a melting point of 233°–235° C.

REFERENCE EXAMPLE 6

Similar to a procedure as mentioned in REFERENCE EXAMPLE 5, there is obtained 8-bromo-5-hydroxycarbostyril in the form of colorless needle-like crystals (recrystallization solvent is methanol) with a melting point of 266°–267° C. (decomposition)

REFERENCE EXAMPLE 7

22.7 grams of 8-bromo-5-methoxy-3,4-dihydrocarbostyril and 25 g of cuprous chloride are mixed with 100 ml of dimethyl sulfoxide and heated at 135°–140° C. for 4 hours under stirring conditions. After the reaction is completed, the reaction mixture is mixed with 200 g of ice and 50 ml of concentrated hydrochloric acid and stirred at a room temperature for 1 hour. The crystals thus precipitated are separated by filtration, washed first with diluted hydrochloric acid and then with water and dried. The crude crystals thus obtained are recrystallized from ligroin-benzene to obtain 13 g of 8-chloro-5-methoxy-3,4-dihydrocarbostyril in the form of pale organic needle-like crystals with a melting point of 165° C.

The thus-obtained 13 g of 8-chloro-5-methoxy-3,4-dihydrocarbostyril and 35 g of aluminum chloride are dispersed in 30 ml of benzene and heated for 2 hours under refluxing conditions. The reaction mixture is poured into ice-water and the precipitate thus formed is separated by filtration, washed with water and dried. Recrystallization from isopropanol obtains 8 g of 8-chloro-5-hydroxy-3,4-dihydrocarbostyril in the form of colorless need-like crystals with a melting point of 206°–207° C.

REFERENCE EXAMPLE 8

20.0 grams of 8-chloro-5-hydroxy-3,4-dihydrocarbostyril and 18 g of potassium carbonate are suspended in 160 ml of isopropyl alcohol, then 40 ml of epichlorohydrin are added and the reaction is carried out at 70°–80° C. for 6 hours. The reaction mixture is concentrated under reduced pressure and the thus-obtained residue is stirred with 100 ml of 2N-sodium hydroxide under cooling conditions. The insoluble matter is separated by filtration, washed with water and dried. The crude crystals are recrystallized from isopropanol to obtain 18.5 g of 8-chloro-5-(2,3-epoxypropoxy)-3,4-dihydrocarbostyril in the form of colorless needle-like crystals with a melting point of 161°–165° C.

REFERENCE EXAMPLE 9

20.0 grams of 6-chloro-7-hydroxy-3,4-dihydrocarbostyril and 3.7 g of sodium hydroxide are mixed with 100 ml of methanol and stirred for 3 hours, then 150 ml of epichlorohydrin is added thereto and heated for 5 hours under refluxing conditions. After the reaction is completed, the reaction mixture is concentrated under reduced pressure to dryness. The residue thus obtained is mixed with 100 ml of 2N-sodium hydroxide and stirred well. The insoluble matter is separated by filtration, washed with water and dried. The crude crystals thus obtained are recrystallized from methanol-ethanol to obtain 19.7 g of 6-chloro-7-(2,3-epoxypropoxy)-3,4-dihydrocarbostyril in the form of colorless crystals with a melting point of 190°–192° C.

REFERENCE EXAMPLE 10-13

Similar to procedures mentioned in REFERENCE EXAMPLES 8-9, there are obtained the following compounds.

| REFERENCE EXAMPLE No. | Compound | Crystal form (Recrystallization solvent) | Melting point (°C.) |
| --- | --- | --- | --- |
| 10 | 6-Chloro-5-(2,3-epoxypropoxy)-3,4-dihydrocarbostyril | Colorless crystals (Isopropanol) | 218–221 |
| 11 | 6,8-Dichloro-5-(2,3-epoxypropoxy)-3,4-dihydrocarbostyril | Colorless crystals (Methanol) | 177–178 |
| 12 | 8-Bromo-5-(2,3-epoxypropoxy)-3,4-dihydrocarbostyril | Colorless needle-like crystals (Methanol) | 220–222 |
| 13 | 5,6-Dichloro-8-(2,3-epoxypropoxy)-3,4-dihydrocarbostyril | Colorless crystals (Methanol) | 183–184 |

REFERENCE EXAMPLE 14

24.3 grams 8-bromo-5-hydroxy-3,4-dihydrocarbostyril and 9 g of potassium hydroxide are mixed with 150 ml of isopropanol and stirred at 70°-80° C. for 30 minutes. Then 25 g of 1,3-bromochloropropane are added thereto and heated for 6 hours under refluxing conditions. After the reaction is completed, the reaction mixture is poured into 200 ml of 2N-sodium hydroxide aqueous solution, then the insoluble matter thus formed is separated by filtration, washed with water and dried. The crude crystals thus obtained are recrystal-lized with ethanol to obtain 21.5 g of 8-bromo-5-(3-chloropropoxy)-3,4-dihydrocarbostyril in the form of colorless needle-like crystals with a melting point of 184°-185° C.

REFERENCE EXAMPLE 15

5 grams of 6-chloro-8-bromo-7-hydroxy-3,4-dihydrocarbostyril and 3 g of sodium hydroxide are mixed with 120 ml of isopropanol and stirred at 50°-60° C. for 1 hour. Then 10 ml of 3-bromo-1-chloropropane are added thereto and stirred at 70°-80° C. for 6 hours. The reaction mixture is concentrated under reduced pressure to dryness and the residue thus obtained is extracted with chloroform. The chloroform layer is washed with water and dried. Then chloroform is removed by distillation and the residue thus formed is recrystallized from ethanol to obtain 6.2 g of 6-chloro-8-bromo-7-(3-chloropropoxy)-3,4-dihydrocarbostyril in the form of colorless needle-like crystals with a melting point of 87°-88° C.

REFERENCE EXAMPLES 16-19

Similar to a procedure as mentioned in REFERENCE EXAMPLE 15, there are obtained the following compounds.

| REFERENCE EXAMPLE NO. | Compound | Crystal form (Recrystallization solvent) | Melting point (°C.) |
|---|---|---|---|
| 16 | 4-Methyl-6-(3-chloropropoxy)carbostyril | Colorless needle-like crystals (Ethanol) | 183 |
| 17 | 4-Methyl-7-(3-chloropropoxy)carbostyril | Colorless needle-like crystals (Ethanol) | 169-170 |
| 18 | 5-(2-Methyl-3-chloropropoxy)-3,4-dihydroxycarbostyril | Colorless needle-like crystals (Ethanol) | 139-140 |
| 19 | 7-(2-Methyl-3-chloropropoxy)-3,4-dihydrocarbostyril | Colorless needle-like crystals (Ethanol-water) | 75-76 |

REFERENCE EXAMPLE 20

18.3 grams of 3,4,5-trimethoxyaniline and 31.2 g of bis($\beta$-bromoethyl)amine monohydrobromide are mixed with 170 ml of methanol and refluxed by heating under a nitrogen gas stream for 10 hours. After cooling the reaction mixture, 5.3 g of anhydrous sodium carbonate are added to the mixture and refluxed by heating for additional 10 hours. Under reduced pressure, about 70 ml of methanol are removed off by distillation, and the mixture is allowed to staand to cool at room temperature. The crystals thus precipitated are collected by filtration and washed with a small amount of ethanol. Recrystallization from ethanol obtains 38 g of 4-(3,4,5-trimethoxyphenyl)piperazine monohydrobromide in the form of colorless plate-like crystals with a melting point of 227°-228° C.

Then this compound is dissolved in 20% sodium hydroxide aqueous solution and extracted with chloroform. The chloroform layer is washed with a saturated sodium chloride aqueous solution three times, then dried, and chloroform is removed by distillation. A free form of 4-(3,4,5-trimethoxyphenyl)piperazine is obtained as a single substance in the form of colorless viscose oily material. The chemical structure of this compound is identified by methods of NMR and IR (infrared absorption spectrum).

EXAMPLE 1

4.4 grams of 5-(2,3-epoxypropoxy)-3,4-dihydrocarbostyril and 3.4 g of 4-phenylpiperazine are dispersed in 60 ml of methanol and reacted at 50°-60° C. for 3 hours. After the reaction is completed, the reaction mixture is concentrated under a reduced pressure. To the residue thus obtained are added 5 ml of concentrated hydrochloric acid and 30 ml of ethanol to dissolve the residue uniformly and further 200 ml of acetone are added. The crystals precipitated are collected by filtration and dried. Recrystallization from water to obtain 6.5 g of 5-[2-hydroxy-3-(4-phenylpiperazinyl)propoxy]-3,4-dihydro carbostyril monohydrochloride in the form of colorless needle-like crystals with a melting point of 239°-241° C.

EXAMPLE 2

4.4 grams of 6-(2,3-epoxypropoxy)-3,4-dihydrocarbostyril and 3.4 g of 4-phenylpiperazine are dispersed in 80 ml of isopropanol and reacted at 50°-60° C. for 3 hours under stirring conditions, then 5 ml of concentrated hydrochloric acid are added thereto and concentrated under reduced pressure to dryness. The thus obtained residue is recrystallized from hot water to obtain 6.1 g of 6-[2-hydroxy-3-(4-phenylpiperazinyl)propoxy]-3,4-dihydrocarbostyril monohydrochloride.½ hydrate in the form of colorless needle-like crystals with a melting point of 223°-224° C.

EXAMPLE 3

2.9 grams of 1-(3-methylbutyl)-5-(2,3-epoxypropoxy)-3,4-dihydrocarbostyril and 1.7 g of 4-phenylpiperazine are mixed with 50 ml of methanol and reacted at 50°-60° C. for 3 hours. The reaction mixture is concentrated under reduced pressure and the residue thus obtained is dissolved in 50 ml of acetone. Into this solution, 20 ml of an acetone solution containing 1.1 g of oxalic acid are added, then the precipitate thus formed is collected by filtration, washed with acetone and dried. Recrystallization from ethanol-ether to obtain 2.1 g of 1-(3-methylbutyl)-5-[2-hydroxy-3-(4-phenylpiperazinyl)propoxy]-3,4-dihydrocarbostyril monooxalate in the form of colorless crystals. This product is confirmed as a single compound by a silica-gel thin layer chromatography-(developing solvent; chloroform:methanol=9:1).

Elemental analysis: $C_{29}H_{39}O_7N_3$: Calculated (%): C 64.30, H 7.26, N 7.76. Found (%): C 64.52, H 7.10, N 7.48.

IR (infrared absorption spectrum):

NMR*: δ = 6.8–7.3 ppm (aromatic proton, 8H)
= 0.92 ppm (methylproton, 6H)

(*Note: The NMR measurements are carried out with d⁶-DMSO)

The compound thus obtained is neutralized by a usual method and the crude crystals are recrystallized from ethanol to obtain 1-(3-methylbutyl)-5-[2-hydroxy-3-(4-phenylpiperazinyl)propoxy]-3,4-dihyrocarbostyril in the form of colorless prism-like crystals with a melting point of 156°–157° C.

EXAMPLE 4

3.4 grams of 1-(3-phenylpropyl)-5-(2,3-epoxypropoxy)-3,4-dihydrocarbostyril and 2.0 g of 4-(4-methylphenyl)piperazine are mixed with 50 ml of methanol and reacted by the procedure similar to that mentioned in EXAMPLE 3 above. The crude crystals thus obtained are recrystallized from methanol-ether to obtain 4.2 g of 1-(3-phenylpropyl)-5-{2-hydroxy-3-[4-(4-methylphenyl)piper azinyl]propoxy}-3,4-dihydrocarbostyril monooxalate in the form of colorless crystals.

Elemental analysis: $C_{34}H_{41}O_7N_3$: Calculated (%): C 67.64; H 6.85, N 6.96. Found (%): C 67.85, H 6.52, N 6.81.

IR (Infrared absorption spectrum): 3480 cm$^{-1}$ (OH), 1675 cm$^{-1}$ (C=O).

NMR**: δ = 6.6–7.4 ppm (aromatic proton, 12H)
= 2.30 ppm (methylproton, 3H)

(**The NMR measurements are carried out with d⁶-DMSO)

EXAMPLES 5–23

By procedures similar to those mentioned in EXAMPLES 1–4, there are obtained compounds as follows:

| EXAMPLE No. | Compound | Crystal form (Recrystallization solvent) | Melting point (°C.) |
|---|---|---|---|
| 5 | 8-[2-Hydroxy-3-(4-phenylpiperazinyl)propoxy]-3,4-dihydrocarbostyril | Colorless crystals (Methanol-ether) | 263 |
| 6 | 6-{2-Hydroxy-3-[4-(4-chlorophenyl)piperazinyl]propoxy}-3,4-dihydrocarbostyril monohydrochloride.½ hydrate | Colorless needle-like crystals (Ethanol) | 212–214 |
| 7 | 7-{2-Hydroxy-3-[4-(4-chlorophenyl)piperazinyl]propoxy}-3,4-dihydrocarbostyril monohydrochloride.monohydrate | Colorless needle-like crystals (Isopropanol) | 66–70 |
| 8 | 8-Bromo-5-[2-hydroxy-3-(4-phenylpiperazinyl)propoxy]-3,4-dihydrocarbostyril | Colorless crystals (Methanol) | 174–176 |
| 9 | 8-Chloro-5-[2-hydroxy-3-(4-phenylpiperazinyl)propoxy]-3,4-dihydrocarbostyril monohydrochloride 3/2 hydrate | Colorless crystals (Methanol-ether) | 226–228 |
| 10 | 8-Chloro-5-{2-hydroxy-3-[3-(4-chlorophenyl)piperazinyl]propoxy}-3,4-dihydrocarbostyril monohydrochloride | Colorless needle-like crystals (Methanol-ether) | 228–230 |
| 11 | 6-Chloro-5-[2-hydroxy-3-(4-phenylpiperazinyl)propoxy]-3,4-dihydrocarbostyril dihydrochloride. monohydrate | Colorless needle-like crystals (Methanol-ether) | 218–225 |
| 12 | 6,8-Dichloro-5-[2-hydroxy-3-(4-phenylpiperazinyl)-propoxy]-3,4-dihydrocarbostyril monohydrochloride | Colorless crystal (Water) | 251–253 |
| 13 | 8-Chloro-5-{2-hydroxy-3-[4-(2-chlorophenyl)piperazinyl]propoxy}-3,4-dihydrocarbostyril | Colorless crystals (Ethanol) | 156–158 |
| 14 | 8-Bromo-5-{2-hydroxy-3-[4-(2-methoxyphenyl)piperazinyl]propoxy}-3,4-dihydrocarbostyril-dihydrochloride | Colorless crystals (Methanol-ether) | 226–228 |
| 15 | 6-Chloro-7-[2-hydroxy-3-(4-phenylpiperazinyl)propoxy]-3,4-dihydrocarbostyril | Colorless needle-like crystals (Methanol-water) | 171–173 |
| 16 | 6-Chloro-7-{2-hydroxy-3-[4-(2-methoxyphenyl)piperazinyl]propoxy}-3,4-dihydrocarbostyril | Colorless crystals (Ethanol) | 183–184 |
| 17 | 1-Methyl-5-[2-hydroxy-3-(4-phenylpiperazinyl)propoxy]-3,4-dihydrocarbostyril | Colorless needle-like crystals (n-Hexane-benzene) | 143–145 |
| 18 | 1-Ethyl-5-[2-hydroxy-3-(4-phenylpiperazinyl)propoxy]-3,4-dihydrocarbostyril. mono-oxalate | Colorless crystals (Ethanol-ether) | 201–203 (decomp.) |
| 19 | 1-Allyl-5-{2-hydroxy-3-[4-(4-methylphenyl)piperazinyl]propoxy}-3,4-dihydrocarbostyril | Colorless needle-like crystals (Ligroin-benzene) | 123–124 |
| 20 | 1-Benzyl-5-[2-hydroxy-3-(4-phenylpiperazinyl)propoxy]-3,4-dihydrocarbostyril | Colorless needle-like crystals (Petroleum benzine-ether) | 148–150 |
| 21 | 6-[2-Hydroxy-3-(4-phenylpiperazinyl)propoxy]carbostyril. ½ hydrate | Colorless crystals (Methanol) | 218–219 |
| 22 | 8-Bromo-5-[2-hydroxy-3-(4-phenylpiperazinyl)propoxy]carbostyril | Colorless plate-like crystals (Methanol) | 179–182 |
| 23 | 6,8-Dichloro-5-{2-hydroxy-3-[4-(4-chlorophenyl)piperazinyl]propoxy}-3,4-dihydrocarbostyril. monohydrochloride. ½ hydrate | Colorless powder-like crystals (Methanol) | 158–161 |

EXAMPLE 24

2.4 grams of 4-methyl-7-(2,3-epoxypropoxy)-carbostyril and 1.8 g of 4-phenylpiperazine are mixed with 30 ml of ethanol and heated for 3 hours under refluxing conditions. After cooling the reaction mixture, the crystals thus precipitated are collected by filtration and washed with ether. The crude crystals thus obtained are dissolved in 50 ml of methanol and 3 ml of concentrated hydrochloric acid, then the mixture is concentrated under reduced pressure to dryness. The residue thus obtained is recrystallized from ethanol-ether to obtain 2.7 g (yield: 63%) of 4-methyl-7-[2-hydroxy-3-(4-phenylpiperazinyl)propoxy]carbostyril monohydrochloride in the form of colorless crystals with a melting point of 190°–191° C.

EXAMPLE 25

Similar to the procedure as mentioned in EXAMPLE 24, 4-methyl-6-[2-hydroxy-3-(4-phenylpiperazinyl)-propoxy]carbostyril ½ hydrate in the form of colorless crystals (recrystal-lized from ethanol) with a melting point of 212°–213° C. is obtained.

EXAMPLE 26

4.8 grams of 5-(3-chloropropoxy)-3,4-dihydrocarbostyril and 4 g of phenylpiperazine are mixed with 40 ml of toluene and heated for 24 hours under refluxing conditions. Then the reaction mixture is concentrated under reduced pressure to dryness. The residue thus obtained is dissolved in 80 ml of chloroform and the chloroform layer is washed twice with 5.0% of sodium hydrogencarbonate aqueous solution, further washed twice with water, dried with anhydrous sodium sulfate and chloroform is removed by distillation. To the residue thus obtained is added hexane and the insoluble material is collected by filtration, then the insoluble material is dissolved in 30 ml of 5% HCl-methanol solution and concentrated under reduced pressure to dryness. Then the residue thus obtained is recrystallized from methanol-ether to obtain 3.2 of 5-[3-(4-phenyl-piperazinyl)propoxy]-3,4-dihydrocarbostyril monohydrochloride in the form of colorless crystals with a melting point of 262° C. (decomposition).

EXAMPLE 27

4.5 grams of 6-(2-chloroethoxy)-3,4-dihydrocarbostyril and 3.3 g of sodium iodide are mixed with 50 ml of acetone and heated for 5 hours under refluxing condition. Then 40 ml of dimethylformamide are added to the reaction mixture and acetone is removed by distillation at 40°–45° C. under reduced pressure. Further, 3.8 g of phenylhydrazine are added to the reaction mixture and the reaction is carried at 60°–70° C. for 7 hours under stirring conditions. The reaction mixture is concentrated under reduced pressure to dryness and the residue thus obtained is dissolved in 80 ml of chloroform. The chloroform layer is washed twice with 5%-sodium hydrogencarbonate aqueous solution and washed twice with water. After drying the chloroform layer, chloroform is removed by distillation. The residue thus obtained is purified by a silica gel chromatography column (silica gel: Wakol gel C-200, a trademark, manufactured by and sold from Wako Chemical Co., Ltd.; elution solvent chloroform methanol=20:1), then the desired compound is converted into the hydrochloride by using ethanol saturated with hydrogen chloride and ethanol is removed by distillation under reduced pressure. The thus obtained residue is recrystallized from methanol-ether to obtain 3.8 g of 6-[2-(4-phenylpiperazinyl)ethoxy]-3,4-dihydrocarbostyril monohydrochloride.monohydrate in the form of colorless crystals with a melting point of 196°–198° C.

EXAMPLES 28–72

Similar to the procedure as mentioned in EXAMPLES 26–27, there are obtained compounds as follows:

| EXAMPLE No. | Compound | Crystal form (Recrystallization solvent) | Melting point (°C.) |
|---|---|---|---|
| 28 | 5-[2-(4-Phenylpiperazinyl)ethoxy]-3,4-dihydrocarbostyril dihydrochloride | Colorless flake-like crystals (Methanol-ether) | 270 (decomp.) |
| 29 | 6-{3-[4-(2-Methoxyphenyl)piperazinyl]-propoxy}carbostyril dihydrochloride | Colorless crystals (Methanol) | 241–242 (decomp.) |
| 30 | 7-[2-(4-Phenylpiperazinyl)ethoxy]-3,4-dihydrocarbostyril | Colorless needle-like crystals (Ethanol) | 171–175 |
| 31 | 7-[3-(4-Phenylpiperazinyl)propoxy]-3,4-dihydrocarbostyril dihydrochloride.¾ hydrate | Colorless needle-like crystals (Methanol-ether) | 213–215 |
| 32 | 8-[2-(4-Phenylpiperazinyl)ethoxy]-3,4-dihydrocarbostyril dihydrochloride.¼ hydrate | Colorless crystals (Methanol-ether) | 255 (decomp.) |
| 33 | 1-Methyl-5-[3-(4-phenylpiperazinyl)-propoxy]-3,4-dihydrocarbostyril dihydrochloride.½ hydrate | Colorless crystals (Ethanol-ether) | 226–228 |
| 34 | 8-Bromo-5-{3-[4-(4-methylphenyl)-piperazinyl]propoxy}-3,4-dihydrocarbostyril | Pale yellowish needle-like crystals (Ligroin-benzene) | 181–182 |
| 35 | 5-{4-[4-(4-Methylchenyl)piperazinyl]-butoxy}-3,4-dihydrocarbostyril | Colorless plate-like crystals (Methanol) | 170–172 |
| 36 | 5-{5-[4-(2-Methoxyphenyl)piperazinyl]-pentyloxy}-3,4-dihydrocarbostyril | Colorless needle-like crystals (Ethanol) | 154–156 |
| 37 | 5-{2-[4-(4-Methylphenyl)piperazinyl]-ethoxy}-3,4-dihydrocarbostyril | Colorless plate-like crystals (Ethanol) | 179–182 |
| 38 | 6-[3-(4-Phenylpiperazinyl)propoxy]-carbostyril | Colorless flake-like crystals (Methanol) | 226–227 |
| 39 | 8-{3-[4-(2-Methoxyphenyl)piperazinyl]-propoxy}-carbostyril. dihydrochloride | Colorless needle-like crystals (Methanol-ether) | 242–245 (decomp.) |
| 40 | 7-[3-(4-Phenylpiperazinyl)-propoxy]carbostyril | Yellowish needle-like crystals (Methanol) | 237–238 |
| 41 | 8-Bromo-5-[3-(4-phenylpiperazinyl)-propoxy]carbostyril. dihydrochloride. monohydrate | Colorless needle-like crystals (Methanol) | 206 |
| 42 | 7-{3-[4-(4-Methylphenyl)piperazinyl]-propoxy}-3,4-dihydrocarbostyril | Yellowish needle-like crystals (Ethanol) | 149–150 |
| 43 | 5-{3-[4-(2-Ethoxyphenyl)piperazinyl]-propoxy}-3,4-dihydrocarbostyril | Colorless needle-like crystals (Ethanol) | 155–156 |
| 44 | 7-{3-[4-(2-Ethoxy- | Colorless | 140–142 |

-continued

| EXAMPLE No. | Compound | Crystal form (Recrystallization solvent) | Melting point (°C.) |
|---|---|---|---|
| | phenyl)piperazinyl]propoxy}-3,4-dihydrocarbostyril | needle-like crystals (Ethanol) | |
| 45 | 6-Chloro-7-[3-(4-phenylpiperazinyl)propoxy]-3,4-dihydrocarbostyril.dihydrochloride.monohydrate | Colorless needle-like crystals (Methanol-ether) | 280 (decomp.) |
| 46 | 6-Bromo-7-[3-(4-phenylpiperazinyl)propoxy]-3,4-dihydrocarbostyril.dihydrochloride | Colorless needle-like crystals (Methanol-ether) | 255–258 |
| 47 | 7-{3-[4-(2-Chlorophenyl)piperazinyl]propoxy}-3,4-dihydrocarbostyril | Pale yellowish prism-like crystals (Ethanol) | 146–147 |
| 48 | 7-{3-[4-(3-Chlorophenyl)piperazinyl]propoxy}-3,4-dihydrocarbostyril | Colorless needle-like crystals (Ethanol) | 156–158 |
| 49 | 7-{3-[4-(4-Chlorophenyl)piperazinyl]propoxy}-3,4-dihydrocarbostyril | Pale yellowish prism-like crystals (Ethanol) | 200–202 |
| 50 | 7-{3-[4-(2-Methoxyphenyl)piperazinyl]propoxy}-3,4-dihydrocarbostyril | Colorless powdery crystals (Ethanol) | 134–137 |
| 51 | 7-{3-[4-(4-Methoxyphenyl)piperazinyl]propoxy}-3,4-dihydrocarbostyril | Colorless needle-like crystals (Ethanol) | 146–149 |
| 52 | 6-[3-(4-Phenylpiperazinyl)propoxy]-3,4-dihydrocarbostyril | Colorless plate-like crystals (Ethanol) | 184–185 |
| 53 | 8-[3-(4-Phenylpiperazinyl)propoxy]-3,4-dihydrocarbostyril | Colorless plate-like crystals (Ethanol) | 112–114 |
| 54 | 7-[4-(4-Phenylpiperazinyl)butoxy]-3,4-dihydrocarbostyril | Colorless needle-like crystals (iso-Propanol) | 123–124 |
| 55 | 5-{3-[4-(2-Methoxyphenyl)piperazinyl]propoxy}-3,4-dihydrocarbostyril | Colorless prism-like crystals (Methanol) | 194–196 |
| 56 | 7-{3-[4-(2-Methoxyphenyl)piperazinyl]propoxy)carbostyril | Colorless powdery crystals (Ethanol) | 229–232 |
| 57 | 1-Benzyl-7-[3-(4-phenylpiperazinyl)propoxy]-3,4-dihydrocarbostyril | Pale yellowish needle-like crystals (Ethanol) | 125–127 |
| 58 | 1-Allyl-7-[3-(4-phenylpiperazinyl)propoxy]-3,4-dihydrocarbostyril.dihydrochloride | Colorless crystals (Ethanol) | 189–192 |
| 59 | 1-Propargyl-7-[3-(4-phenylpiperazinyl)propoxy]-3,4-dihydrocarbostyril.dihydrochloride | Pale brownish needle-like crystals (Methanol) | 215–216 |
| 60 | 1-Hexyl-7-[3-(4-phenylpiperazinyl)propoxy]-3,4-dihydrocarbostyril.dihydrochloride | Colorless crystals (Ethanol-acetone-ether) | 176–181 |
| 61 | 1-(3-Phenylpropyl)-7-[3-(4-phenylpiperazinyl)propoxy]-3,4-dihydrocarbostyril.monohydrochloride | Colorless flake-like crystals (Ethanol) | 201–202 |
| 62 | 1-Benzyl-5-[3-(4-phenylpiperazinyl)propoxy]-3,4-dihydrocarbostyril | Pale yellowish needle-like crystals (Ligroin) | 113 |
| 63 | 1-Ethyl-7-[3-(4-phenylpiperazinyl)propoxy]-3,4-dihydrocarbostyril.dihydrochloride | Colorless crystals (Ethanol) | 222–224 |
| 64 | 1-Methyl-7-[3-(4-phenylpiperazinyl)propoxy]-3,4-dihydrocarbostyril.dihydrochloride | Colorless crystals (Ethanol) | 204–207 |
| 65 | 4-Methyl-7-[3-(4-phenylpiperazinyl)propoxy]-3,4-dihydrocarbostyril dihydrochloride.dihydrate | Colorless crystals (Methanol-ether) | 260–265 |
| 66 | 5-[3-(4-Acetylpiperazinyl)propoxy]-3,4-dihydrocarbostyril | Colorless needle-like crystals (Ethanol) | 143–145 |
| 67 | 5-[3-(4-Benzoylpiperazinyl)propoxy]-3,4-dihydrocarbostyril.hydrochloride | Colorless plate-like crystals (Methanol-ether) | 240 (decomp.) |
| 68 | 5-{3-[4-(2-Acetyloxyethyl)piperazinyl]propoxy}-3,4-dihydrocarbostyril | Colorless needle-like crystals (Isopropanol) | 131–132 |
| 69 | 5-{3-[4-(2-Hydroxyethyl)piperazinyl]propoxy}-3,4-dihydrocarbostyril | Colorless flake-like crystals (Water) | 158–159 |
| 70 | 4-Phenyl-7-[3-(4-phenylpiperazinyl)propoxy]carbostyril | Colorless needle-like crystals (Methanol) | 198–199 |
| 71 | 4-Phenyl-7-[3-(4-phenylpiperazinyl)propoxy]-3,4-dihydrocarbostyril | Colorless needle-like crystals (Ether-hexane) | 138–140 |
| 72 | 4-Phenyl-7-{3-[4-(2-methoxyphenyl)piperazinyl]propoxy)carbostyril | Colorless needle-like crystals (Isopropanol-water) | 161–162 |

EXAMPLE 73

4.8 grams of 7-(3-chloropropoxy)-34-dihydrocarbostyril and 3.5 g of sodium iodide are mixed with 50 ml of acetone and heated for 3 hours under refluxing conditions. Then 40 ml of dimethylformamide are added thereto and acetone is removed by distillation at 40°–45° C. under reduced pressure. Further 4.0 g of 4-(3-fluorophenyl)-piperazine and 3.0 g of triethylamine are added thereto and the reaction is carried out at 70°–80° C. for 27 hours under stirring conditions. The reaction mixture is concentrated under reduced pressure to dryness. To the residue thus obtained is added 60 ml of an aqueous solution of 5% sodium hydrogencarbonate and extracted with chloroform. The chloroform layer is extracted twice with water and dried; then chloroform is removed by distillation. To the residue thus obtained is added ether and the insoluble material is collected by filtration and dried. Recrystallization from methanol obtains 6.2 g of 7-{3-[4-(3-fluorophenyl)-piperazinyl]propoxy}-3,4-dihydrocarbostyril in the form of pale yellowish, needle-like crystals with a melting point of 174°–176° C.

EXAMPLE 74

12.4 grams of 7-(3-chloropropoxy-3,4-dihydrocarbostyril, 1 g of pyridine and 2.6 g of 4-(3,4,5-trimethoxyphenyl)piperazine are mixed in 20 ml of dimethylsulfoxide, then stirred at 80°–90° C. for 5 hours. The reaction mixture is poured into 80 ml of 2% aqueous solution of sodium hydrogencarbonate and the organic layer is extracted with chloroform. The chloroform layer is washed with water, dried and chloroform is removed by distillation. The residue thus obtained is dissolved in 30 ml of ethanol and dried hydrogen chloride gas is blown into the ethanol solution. The crystals thus precipitated are collected by filtration and recrystallized from methanol-ethanol to obtain 3.2 g (yield: 61%) of 7-{3-[4-(3,4,5-trimethoxyphenyl)-piperazinyl]propoxy}-3,4-dihydrocarbostyril dihydrochloride in the form of colorless needle-like crystals with a melting point of 225°–227° C.

EXAMPLE 75–80

Similar to the procedure as mentioned in EXAMPLE 74, there are obtained compounds as follows:

| EXAM-PLE No. | Compound | Crystal form (Recrystallization solvent) | Melting point (°C.) |
|---|---|---|---|
| 75 | 5-{3-[4-(2-Fluorophenyl)piperazinyl]-propoxy}-3,4-dihydrocarbostyril | Colorless needle-like crystals (Methanol) | 175–178 |
| 76 | 7-{3-[4-(2-Fluorophenyl)piperazinyl]-propoxy}-3,4-dihydrocarbostyril | Colorless needle-like crystals (Methanol) | 154–156 |
| 77 | 5-{3-[4-(3-Fluorophenyl)piperazinyl]-propoxy}-3,4-dihydrocarbostyril | Colorless needle-like crystals (Methanol) | 178–180 |
| 78 | 5-{3-[4-(3,4,5-Trimethoxyphenyl)-piperazinyl]propoxy}-3,4-dihydrocarbostyril dihydrochloride | Colorless crystals (Methanol-ether) | 205–208 (decomp.) |
| 79 | 5-{3-[4-(3,4-Dimethoxyphenyl)-piperazinyl]propoxy}-3,4-dihydrocarbostyril | Pale yellowish needle-like crystals (Ethanol) | 190–192 |
| 80 | 7-{3-[4-(3,4-Dimethoxyphenyl)-piperazinyl]propoxy}-3,4-dihydrocarbostyril | Pale brownish needle-like crystals | 146–147 |

EXAMPLE 81

2.5 grams of 7-(3-Chloro-2-methylpropoxy)-3,4-dihydrocarbostyril and 1.8 g of sodium iodide are mixed with 30 ml of acetone and stirred at room temperature overnight. Then 20 ml of dimethylformamide are added thereto and acetone is removed by distillation under a reduced pressure. Further 1.5 g of triethylamine and 1.8 g of phenylpiperazine are added thereto and the reaction is carried out at 70°–80° C. for 6 hours under stirring conditions. The reaction mixture is then poured into 70 ml of 2% aqueous solution of sodium hydrogencarbonate and the organic layer is extracted with chloroform. The chloroform layer is washed with water and dried. Then chloroform is removed by distillation and the residue thus obtained is washed with petroleum ether. Recrystallization from methanol-water obtains 2.8 g (yield: 74%) of 7-[2-methyl-3-(4-phenylpiperazinyl)propoxy]-3,4-dihydrocarbostyril in the form of colorless flake-like crystals with a melting point of 146°–147° C.

EXAMPLE 82

Similar to the method as described in EXAMPLE 81, there is obtained 5-[2-methyl-3-(4-phenylpiperazinyl)-propoxy]-3,4-dihydrocarbostyril in the form of colorless needle-like crystals (recrystallization solvent: ethanol) with a melting point of 167°–169° C.

EXAMPLE 83

2.7 grams of 4-methyl-7-(3-chloropropoxy)-carbostyril and 1.8 g of sodium iodide are mixed with 50 ml of acetone and heated for 3 hours under refluxing conditions. Then 50 ml of dimethylformamide is added thereto and acetone is removed by distillation under reduced pressure. next, 1.5 g of triethylamine and 1.8 g of 4-phenylpiperazine are added thereto and stirred for 3 hours at 80°–90° C. and dimethylformamide is removed by distillation under reduced pressure. To the residue thus obtained is added 5% sodium hydrogencarbonate aqueous solution to effect crystallization of the product and the precipitates formed are collected by filtration, washed with water, washed with isopropanol, further washed with ether and dried. The crude crystals thus obtained are dispersed in 80 ml of methanol, and dissolved by adding 5 ml of concentrated hydrochloric acid, then concentrated under a reduced pressure to dryness. The thus obtained residue is recrystallized from methanol-ether to obtain 3.6 g (yield: 80%) of 4-methyl-7-[3-(4-phenylpiperazinyl)propoxy]carbostyril dihydrochloride in the form of colorless crystals with a melting point of 253°–254° C. (decomp.).

EXAMPLE 84

Similar to the procedure as mentioned in EXAMPLE 83, there is obtained 4-methyl-6-[3-(4-phenylpiperazinyl)propoxy]carbostyril.dihydro.chloride trihydrate in the form of pale brownish crystals (from ethanol) with a melting point of 285°–290° C. (decomp.).

EXAMPLE 85

2.4 grams of 5-(3-chloroproxy)-3,4-dihydrocarbostyril and 1.7 g of sodium iodide are mixed with 30 ml of acetone and heated for 3 hours under refluxing conditions. Then 30 ml of dimethylformamide are added to the reaction mixture and acetone is removed by distillation under a reduced pressure. Next, 1.5 g of triethylamine, and 1.8 g of 4-phenylhomopiperazine are added thereto and heated at 60°–70° C. for 5 hours with stirring. The reaction mixture is poured into 80 ml of 3% sodium hydrogencarbonate aqueous solution and the organic layer is extracted with chloroform. The chloroform layer is washed with water, dried and chloroform is removed by distillation. The thus obtained residue is recrystallized from ligroin-benzene to obtain 3.2 g (yield: 83%) of 5-[3-(4-phenylhomopiperazinyl)propoxy]-3,4-dihydrocarbostyril in the form of colorless flake-like crystals with a melting point of 122°–125° C.

EXAMPLES 86–88

Similar to the procedure mentioned in EXAMPLE 85, there are obtained the following compounds:

| EXAMPLE No. | Compound | Crystal form (Recrystallization solvent) | Melting point (°C.) |
|---|---|---|---|
| 86 | 7-[3-(4-Phenylhomopiperazinyl)propoxy]-3,4-dihydrocarbostyril | Pale yellowish flake-like crystals (Petroleum benzine) | 72–74 |
| 87 | 5-[3-(4-Cyclohexylpiperazinyl)propoxy]-3,4-dihydrocarbostyril | Colorless needle-like crystals (Ethanol) | 173–176 |
| 88 | 7-[3-(4-Cyclohexylpiperazinyl)propoxy]-3,4-dihydrocarbostyril | Colorless needle-like crystals (Ligroin-benzene) | 115–125 |

EXAMPLE 89

24 grams of 5-(3-chloropropoxy)-3,4-dihydrocarbostyril and 17 g of sodium iodide are mixed with 300 ml of acetone and heated for 3 hours under refluxing conditions. Then, 300 ml of dimethylformamide, 12 g of triethylamine and 18 g of 4-benzylpiperazine are added thereto and the reaction is carried out at 60°–70° C. for 7 hours under stirring conditions. The reactions mixture is concentrated under a reduced pressure to obtain a viscous liquid, then 300 ml of 3% sodium hydrogencarbonate aqueous solution are added. The organic layer is extracted with chloroform and washed with water. After drying the chloroform layer, chloroform is removed by distillation. The residue thus obtained is washed with ether and recrystallized from methanol to obtain 32 g (yield: 84%) of 5-[3-(4-benzylpiperazinyl)-propoxy]-3,4-dihydrocarbostyril in the form of colorless needle-like crystals with a melting point of 157°–159° C.

EXAMPLES 90 AND 91

Similar to the procedure described in EXAMPLE 89, there are obtained the following compounds:

| EXAMPLE No. | Compound | Crystal form (Recrystallization solvent) | Melting point (°C.) |
|---|---|---|---|
| 90 | 6-[3-(4-Benzylpiperazynil)propoxy]-3,4-dihydrocarbostyril | Colorless needle-like crystals (iso-Propanol) | 114–116 |
| 91 | 7-[3-(4-Benzylpiperazinyl)propoxy]-3,4-dihydrocarbostyril | Colorless needle-like crystals (Ethyl acetate-ether) | 126–127 |

EXAMPLE 92

2.4 grams of 7-(3-chloropropoxy)-3,4-dihydrocarbostyril and 1.8 g of sodium iodide are mixed with 30 ml of acetone and stirred at 50°–60° C. for 3 hours, then 30 ml of dimethylformamide are added thereto. After removal of acetone by distillation under a reduced pressure, 1.5 g of triethylamine and 2.3 g of 4-(4-chlorophenyl)-3-methylpiperazine are mixed therewith and stirred at 70°–80° C. for 7 hours. The reaction mixture is concentrated under a reduced pressure and 50 ml of 3% sodium hydrogencarbonate aqueous solution are added to the thus obtained viscous residue matter and the organic layer is extracted with chloroform. The chloroform layer is washed with water, dried and chloroform is removed by distillation. To the residue thus obtained are added 50 ml of methanol and 5 ml of concentrated hydrochloric acid and the mixture is concentrated under a reduced pressure to dryness. The residue is recrystallized from ethanol to obtain 3.1 g (yield: 75%) of 7-{3-[3-methyl-4-(4-chlorophenyl)-piperazinyl]-propoxy}-3,4-dihydrocarbostyril.dihydrochloride in the form of colorless crystals with a melting point of 235°–242° C.

EXAMPLES 93 AND 94

Similar to the procedure mentioned in EXAMPLE 92, there are obtained the following compounds:

| EXAMPLE No. | Compound | Crystal form (Recrystallization solvent) | Melting point (°C.) |
|---|---|---|---|
| 93 | 8-Bromo-6-chloro-7-[3-(4-phenylpiperazinyl)propoxy]-3,4-dihydrocarbostyril-dihydrochloride [3.7 g (yield: 67%)] | Colorless needle-line crystals (Ethanol) | 229–232 (decomp.) |
| 94 | 4-[3-(4-Phenylpiperazinyl)propoxy]-carbostyril | Colorless flake-like crystals (Ethanol) | 206–208 |

EXAMPLE 95

5.1 grams of 7-(3-chloro-2-hydroxypropoxy)-3,4-dihydrocarbostyril and 8 g of 4-phenylpiperazine are mixed with 50 ml of dimethylformamide and reacted at 50°–60° C. for 5 hours under stirring conditions. The reaction mixture is concentrated under a reduced pressure to dryness and the residue thus obtained is dissolved in 80 ml of chloroform, then the chloroform layer is washed 3 times with 5% of sodium hydrogencarbonate aqueous solution and washed 3 times with water and dried with anhydrous sodium sulfate. Chloroform is removed by distillation under a reduced pressure and the residue thus obtained is purified by a silica gel chromatography [silica gel: Wako C-200, extracting solvent: chloroform:methanol=30:1 (v/v)]. Then the extracted product is converted into its hydrochloride by using ethanol containing hydrogen chloride and ethanol is removed by distillation under a reduced pressure. The thus obtained residue is recrystallized from ater to obtain 5.6 g of 7-[2-hydroxy-3-(4-phenylpiperazinyl)-propoxy]-3,4-dihydro carbostyril.monohydrochloride.½hydrate in the form of colorless crystals with a melting point of 122° C. (decomp.).

EXAMPLES 96–115

Similar to the procedure as described in Example 95, there are obtained the following compounds:

| EXAMPLE No. | Compound | Crystal form (Recrystallization solvent) | Melting point (°C.) |
|---|---|---|---|
| 96 | 5-[2-Hydroxy-3-(4-phenyl)propoxy]-3,4-dihydrocarbostyril.monohydrochloride | Colorless needle-like crystals (Water) | 239–241 |
| 97 | 6-[2-Hydroxy-3-(4-phenylpiperazinyl)-propoxy]-3,4-dihydrocarbostyril.monohydrochloride. | Colorless needle-like crystals (Water) | 223–224 |

-continued

| EXAMPLE No. | Compound | Crystal form (Recrystallization solvent) | Melting point (°C.) |
|---|---|---|---|
| 98 | 8-Chloro-5-[2-hydroxy-3-(4-phenylpiperazinyl)propoxy]-3,4-dihydrocarbostyril. monohydrochloride. 3/2 hydrate | Colorless needle-like crystals (Methanol-ether) | 226–228 |
| 99 | 8-Chloro-5-{2-hydroxy-3-[4-(4-chlorophenyl)piperazinyl]propoxy}-3,4-dihydrocarbostyril. monohydrochloride | Colorless needle-like crystals (Methanol-ether) | 228–230 |
| 100 | 6-Chloro-5-[2-hydroxy-3-(4-phenylpiperazinyl)propoxy]-3,4-dihydrocarbostyril. dihydrochloride. monohydrate | Colorless needle-like crystals (Methanol-ether) | 218–225 |
| 101 | 6,8-Dichloro-5-[2-hydroxy-3-(4-phenylpiperazinyl)propoxy]-3,4-dihydrocarbostyril. monohydrochloride | Colorless crystals (Water) | 251–253 |
| 102 | 8-[2-Hydroxy-3-(4-phenylpiperazinyl)propoxy]-3,4-dihydrocarbostyril.monohydrochloride | Colorless crystals (Methanol-ether) | 263 |
| 103 | 6-{2-Hydroxy-3-[4-(4-chlorophenyl)piperazinyl]propoxy}-3,4-dihydrocarbostyril.monohydrochloride.½ hydrate | Colorless needle-like crystals (Ethanol) | 212–214 |
| 104 | 7-{2-Hydroxy-3-[4-(4-Chlorophenyl)piperazinyl]propoxy}-3,4-dihydrocarbostyril. monohydrochloride | Colorless needle-like crystals (Isopropanol) | 66–70 |
| 105 | 8-Bromo-5-[2-hydroxy-3-(4-phenylpiperazinyl)propoxy]-3,4-dihydrocarbostyril | Colorless crystals (Methanol) | 174–176 |
| 106 | 8-Bromo-5-{2-hydroxy-3-[4-(2-methoxyphenyl)piperazinyl]propoxy}-3,4-dihydrocarbostyril.dihydrochloride | Colorless crystals (Methanol-ether) | 226–228 |
| 107 | 6-Chloro-7-[2-hydroxy-3-(4-phenylpiperazinyl)propoxy]-3,4-dihydrocarbostyril | Colorless needle-like crystals (Methanol-water) | 171–173 |
| 108 | 6-Chloro-7-{2-hydroxy-3-[4-(2-methoxyphenyl)piperazinyl]propoxy}-3,4-dihydrocarbostyril | Colorless crystals (Ethanol) | 183–184 |
| 109 | 1-Methyl-5-[2-hydroxy-3-(4-phenylpiperazinyl)propoxy]-3,4-dihydrocarbostyril | Colorless needle-like crystals (n-Hexane-benzene) | 143–145 |
| 110 | 1-Ethyl-5-[2-hydroxy-3-(4-phenylpiperazinyl)propoxy]-3,4-dihydrocarbostyril. monooxalate | Colorless crystals (Ethanol-ether) | 201–203 (decomp.) |
| 111 | 8-Chloro-5-{2-hydroxy-3-[4-(2-chlorophenyl)piperazinyl]propoxy}-3,4-dihydrocarbostyril | Colorless crystals (Ethanol) | 156–158 |
| 112 | 1-Allyl-5-{2-hydroxy-3-[4-(4-methylphenyl)piperazinyl]propoxy}-3,4-dihydrocarbostyril | Colorless needle-like crystals (Ligroin-benzene) | 123–124 |
| 113 | 1-Benzyl-5-[2-hydroxy-3-(4-phenylpiperazinyl)propoxy]-3,4-dihydrocarbostyril | Colorless needle-like crystals (Petroleum benzene-ether) | 148–150 |
| 114 | 6-[2-Hydroxy-3-(4-phenylpiperazinyl)propoxy]-3,4-dihydrocarbostyril. ½ hydrate | Colorless needle-like crystals (Methanol) | 218–219 |
| 115 | 8-Bromo-5-[2-hydroxy-3-(4-phenylpiperazinyl)propoxy]carbostyril | Colorless plate-like crystals (Methanol) | 179–182 |

EXAMPLE 116

0.55 gram of sodium hydride (about 50% in oil) are washed with petroleum ether, then 30 ml of dimethylformamide and 3.6 g 7-[3-(4-phenylpiperazinyl)propoxy]-3,4-dihydrocarbotyril are added thereto and stirred at room temperature for 1 hour. To the reaction mixture was added 1.2 g of ethyl bromide and stirring occurs at room temperature for 3 hours. The reaction mixture is poured into 150 ml of water and the organic layer is extracted with chloroform. The chloroform layer is washed with water twice, dried with anhydrous sodium sulfate and chloroform is removed by distillation. To the residue thus obtained a small amount of ethanol is added to precipitate crystals. The crystals are collected by filtration and dissolved in 70 ml of methanol and 3 ml of concentrated hydrochloric acid, then concentrated under reduced pressure to dryness. The residue is recrystallized from ethanol to obtain 4.1 g (yield: 88%) of 1-ethyl-7-[3-(4-phenylpiperazinyl)-propoxy]-3,4-dihydrocarbostyril dihydrochloride in the form of colorless crystals with a melting point of 222°–224° C.

EXAMPLE 117

0.3 Gram of sodium metal is dissolved in 80 ml of ethanol and to this solution is added 3.6 g of 5-[3-(4-phenylpiperazinyl)propoxy]-3,4-dihydrocarbostyril, then 1.5 g of benzoyl chloride are added and the solution is heated for 5 hours under refluxing conditions. The reaction mixture is concentrated under reduced pressure to dryness. To the residue thus obtained is added water and the insoluble matter is collected by filtration, washed with ater and dried. The crude crystals are recrystallized from ligroin to obtain 3.9 g (yield: 86%) of 1-benzoyl-5-[3-(4-phenylpiperazinyl)propoxy]-3,4-dihydro carbostyril in the form of pale yellowish needle-like crystals with a melting point of 113° C.

EXAMPLES 118–123

Similar to the procedure as mentioned in EXAMPLE 117, there are obtained the following compounds:

| EXAMPLE No. | Compound | Crystal form (Recrystallization solvent) | Melting point (°C.) |
|---|---|---|---|
| 118 | 1-Benzyl-7-[3-(4-phenylpiperazinyl)-propoxy]-3,4-dihydrocarbostyril | Pale yellowish needle-like crystals (Ethanol) | 125–127 |
| 119 | 1-Methyl-7-[3-(4-phenylpiperazinyl)-propoxy]-3,4-di- | Colorless crystals (Ethanol) | 204–207 |

| EXAMPLE No. | Compound | Crystal form (Recrystallization solvent) | Melting point (°C.) |
| --- | --- | --- | --- |
| 120 | hydrocarbostyril 1-Allyl-7-[3-(4-phenylpiperazinyl)-propoxy]-3,4-dihydrocarbostyril. dihydrochloride | Colorless crystals (Ethanol) | 189–192 |
| 121 | 1-Propargyl-7-[3-(4-phenylpiperazinyl)-propoxy]-3,4-dihydrocarbostyril. dihydrochloride | Pale yellowish needle-like crystals (Methanol) | 215–216 |
| 122 | 1-Hexyl-7-[3-(4-phenylpiperazinyl)-propoxy]-3,4-dihydrocarbostyril. dihydrochloride | Colorless crystals (Ethanol-acetone-ether) | 176–181 |
| 123 | 1-(3-Phenylpropyl)-7-[3-(4-phenyl-piperazinyl)propoxy]-3,4-dihydrocarbostyril. monohydrochloride | Colorless flake-like crystals (Ethanol) | 201–202 |

EXAMPLE 124

1.0 gram of 4-methyl-7-[3-(4-phenylpiperazinyl)-propoxy]carbostyril dihydrochloride and 0.3 g of palladium black are dispersed in 200 ml of ethanol under hydrogen at a pressure of 2 atmospheres at room temperature and catalytic reduction is carried out at 70°–80° C. for 8 hours. After cooling the reaction mixture, the palladium black is removed by filtration and the mother liquor is concentrated to dryness. The residue is recrystallized from a mixture of methanol-ether to obtain 0.6 g (yield: 60%) of 4-methyl-7-[3-(4-phenyl-piperazinyl)-propoxy]-3,4-dihydrocarbostyril.dihydrochloride.dihydrate in the form of colorless crystals with a melting point of 260°–265° C.

EXAMPLE 125

2 grams of 5-[2-hydroxy-3-(4-phenylpiperazinyl)-propoxy]-3,4-dihydrocarbostyril are mixed with 30 ml of acetone and further 12 ml of acetyl chloride are added, followed by heating for 10 hours under refluxing conditions. After cooling the reaction mixture, the product precipitated is collected by filtration and washed with acetone. The crude crystals thus obtained are dissolved in 80 ml of water and made basic with ammonia-water, then extracted with chloroform, dried and chloroform is removed by distillation. The residue is purified by silica gel chromatography to obtain 0.5 g of 5-[2-acetyloxy-3-(4-phenylpiperazinyl)propoxy]-3,4-dihydrocarbostyril in the form of colorless crystals with a melting point of 159°–161° C.

EXAMPLE 126

Similar to the procedure as mentioned in EXAMPLE 125, 7-[2-acetyloxy-3-(4-phenylpiperazinyl)propoxy]-3,4-dihydrocarbostyril in the form of colorless crystals with a melting point of 130°–132° C.

EXAMPLE 127

1.9 grams of 5-[2-hydroxy-3-(4-phenylpiperazinyl)-propoxy]-3,4-dihydrocarbostyril and 0.24 g of sodium hydride are dispersed in 40 ml of xylene and heated for 1 hour under refluxing conditions. Then the bath temperature is lowered to 130° C. and 1.40 g of 3,4,5-trimethoxybenzoyl chloride are added gradually and heated for 8 hours under refluxing condition. Xylene is removed from the reaction mixture by distillation, then the residue is poured into 80 ml of water and extracted with chloroform. The chloroform layer is washed with water, dried and chloroform is removed by distillation. The residue is recrystallized from ethanol to obtain 1.5 g of 5-[2-(3,4,5-trimethoxybenzoyloxyl)-3-(4-phenyl-piperazinyl)propoxy]-3,4-dihydrocarbostyril in the form of colorless crystals with a melting point of 125°–127° C.

EXAMPLE 128

20 grams of 5-(3-piperazinylpropoxy)-3,4-dihydrocarbostyril are mixed with 15 ml of acetic anhydride and 10 ml of acetic acid and heated for 5 hours under refluxing conditions. The reaction mixture is concentrated under reduced pressure to dryness. The residue is recrystallized from Ethanol to obtain 5-[3-(4-acetyl-piperazinyl)propoxy]-3,4-dihydrocarbostyril in the form of colorless needle-like crystals with a melting point of 143°–145° C.

EXAMPLE 129

2.0 grams of 5-(3-piperazinylpropoxy)-3,4-dihydrocarbostyril and 1.5 g of benzoyl chloride are mixed with 20 ml of pyridine and stirred at 50°–60° C. for 3 hours. The reaction mixture is concentrated under reduced pressure to dryness. The residue is converted into a hydrochloric acid-salt thereof, then recrystallized from methanol to obtain 5-[3-(4-benzoylpiperazinyl)-propoxy]-3,4-dihydrocarbostyril hydrochloride in the form of colorless plate-like crystals with a melting point of 240° C. (decomp.).

EXAMPLE 130

20 grams of 5-(3-piperazinylpropoxy)-3,4-dihydrocarbostyril and 3 ml of ethyl 2-bromoacetate and 1.5 ml of triethylamine are mixed with 20 ml of dimethyl formamide at 50°–60° C. for 8 hours under stirring conditions. The reaction mixture is concentrated under reduced pressure and to the viscous residue thus obtained are added 30 ml of 2% sodium hydrogen-carbonate aqueous solution followed by extraction with chloroform. The chloroform layer is washed with water, dried and chloroform is removed by distillation. The residue is purified by silica gel chromatography and recrystallized from isopropanol to obtain 5-{3-[4-(2-acetyloxyethyl)piperazinyl]-propoxy}-3,4-dihydrocarbostyril in the form of colorless needle-like crystals with a melting point of 131°–132° C.

EXAMPLE 131

2.0 grams of 5-{3-[4-(2-acetyloxyethyl)-piperazinyl]-propoxy}-3,4-dihydrocarbostyril are mixed with 30 ml of methanol and 5 ml of concentrated hydrochloric acid and heated for 2 hours under refluxing conditions. The reaction mixture is concentrated under reduced pressure to dryness. The residue is recrystallized from water to obtain 5-{3-[4-(2-hydroxyethyl)piperazinyl]propoxy}-3,4-dihydrocarbostyril in the form of colorless flake-like crystals with a melting point of 158°–159° C.

EXAMPLE 132

2.5 grams of 1-benzyl-5-hydroxy-3,4-dihydrocarbostyril and 0.48 g of 50% oily NaH are mixed with 30 ml of dimethyl formamide and stirred, then 4 g of 1-chloro-3-(4-phenylpiperazinyl)propane are added therein and warmed to 50°–60° C. for 2.5 hours. The reaction mixture is concentrated under a reduced pressure and the residue thus obtained is extracted with chloroform. After removing the chloroform by distillation, the thus obtained residue is recrystallized from ligroin to obtain 2.1 g of 1-benzyl-5-[3-(4-phenylpiperazinyl)-propoxy]-3,4-dihydrocarbostyril in the form of pale yellowish needle-like crystals with a melting point of 113° C.

EXAMPLE 133-162

Similar to procedures as mentioned in Example 132, there are obtained the following compounds:

| EXAMPLE No. | Compounds | Crystal form (Recrystallization solvent) | Melting point (°C.) |
|---|---|---|---|
| 133 | 5-[3-(4-Phenylpiperazinyl)propoxy]-3,4-dihydrocarbostyril. monohydrochloride | Colorless crystals (Methanol-ether) | 262 (decomp.) |
| 134 | 6-[2-(4-Phenylpiperazinyl)ethoxy]-3,4-dihydrocarbostyril. monohydrochloride. monohydrate | Colorless crystals (Methanol-ether) | 196–198 |
| 135 | 7-[3-(4-Phenylpiperazinyl)propoxy]-3,4-dihydrocarbostyril. dihydrochloride. ¾ hydrate | Colorless needle-like crystals (Methanol-ether) | 213–215 |
| 136 | 8-[3-(4-Phenylpiperazinyl)propoxy]-3,4-dihydrocarbostyril | Colorless plate-like crystals (Ethanol) | 112–114 |
| 137 | 7-[3-(4-Phenylpiperazinyl)propoxy]-carbostyril | Yellowish needle-like crystals (Methanol) | 237–238 |
| 138 | 7-{3-[4-(4-Methylphenyl)piperazinyl]propoxy}-3,4-dihydrocarbostyril | Yellowish needle-like crystals (Ethanol) | 149–150 |
| 139 | 6-Bromo-7-[3-(4-phenylpiperazinyl)propoxy]-3,4-dihydrocarbostyril. dihydrochloride | Colorless needle-like crystals (Methanol-ether) | 225–258 |
| 140 | 7-{3-[4-(3-Chlorophenyl)piperazinyl]propoxy}-3,4-dihydrocarbostyril | Colorless needle-like crystals (Ethanol) | 156–158 |
| 141 | 7-{3-[4-(2-Methoxyphenyl)piperazinyl]propoxy}-3,4-dihydrocarbostyril | Colorless powder-like crystals (Ethanol) | 134–137 |
| 142 | 7-[4-(4-Phenylpiperazinyl)butoxy]-3,4-dihydrocarbostyril | Colorless needle-like crystals (Isopropanol) | 123–124 |
| 143 | 1-Methyl-7-[3-(4-phenylpiperazinyl)propoxy]-3,4-dihydrocarbostyril. dihydrochloride | Colorless crystals (Ethanol) | 204–207 |
| 144 | 1-Benzyl-7-[3-(4-Phenylpiperazinyl)propoxy]-3,4-dihydrocarbostyril | Pale yellowish needle-like crystals (Ethanol) | 125–127 |
| 145 | 1-Allyl-7-[3-(4-phenylpiperazinyl)propoxy]-3,4-dihydrocarbostyril. dihydrochloride | Colorless crystals (Ethanol) | 189–192 |
| 146 | 1-Propargyl-7-[3-(4-phenylipiperazinyl)propoxy]-3,4-dihydrocarbostyril. dihydrochloride | Pale yellowish needle-like crystals (Methanol) | 215–216 |
| 147 | 4-Methyl-7-[3-(4-phenylpiperazinyl)propoxy]-3,4-dihydrocarbostyril. dihydrochloride. dihydrate | Colorless crystals (Methanol-ether) | 260–265 |
| 148 | 7-{3-[4-(3,4,5-Trimethoxyphenyl)piperazinyl]propoxy}-3,4-dihydrocarbostyril. dihydrochloride | Colorless needle-like crystals (Methanol-ethanol) | 225–227 (decomp.) |
| 149 | 7-{3-[4-(3,4-Dimethoxyphenyl)piperazinyl]propoxy}-3,4-dihydrocarbostyril | Brown needle-like crystals (Ethanol) | 146–147 |
| 150 | 7-[2-Methyl-3-(4-phenylpiperazinyl)propoxy]-3,4-dihydrocarbostyril | Colorless flake-like crystals (Methanol-water) | 146–147 |
| 151 | 8-Bromo-6-chloro-7-[3-(4-phenylpiperazinyl)propoxy]-3,4-dihydrocarbostyril. dihydrochloride | Colorless needle-like crystals (Ethanol) | 229–232 (decomp.) |
| 152 | 5-[3-(4-Phenylhomopiperazinyl)propoxy]-3,4-dihydrocarbostyril | Colorless flake-like crystals (Ligroin-benzene) | 122–125 |
| 153 | 4-Methyl-7-[3-(4-phenylpiperazinyl)propoxy]carbostyril | Colorless crystals (Methanol-ether) | 253–254 (decomp.) |
| 154 | 5-[3-(4-Cyclohexylpiperazinyl)propoxy]-3,4-dihydrocarbostyril | Colorless needle-like crystals (Ethanol) | 173–176 |
| 155 | 7-[3-(4-Benzylpiperazinyl)propoxy]-3,4-dihydrocarbostyril | Colorless needle-like crystals (Ethyl acetate-ether) | 126–127 |
| 156 | 5-[3-(4-Acetylpiperazinyl)propoxy]-3,4-dihydrocarbostyril | Colorless needle-like crystals (Ethanol) | 143–145 |
| 157 | 5-[3-(4-Benzoylpiperazinyl)propoxy]-3,4-dihydrocarbostyril. monohydrochloride | Colorless plate-like crystals (Methanol-ether) | 240 (decomp.) |
| 158 | 5-{3-[4-(2-Acetyloxyethyl)piperazinyl]propoxy}-3,4-dihydrocarbostyril | Colorless needle-like crystals (Isopropanol) | 131–132 |
| 159 | 5-{3-[4-(2-Hydroxyethyl)piperazinyl]propoxy}-3,4-dihydrocarbostyril | Colorless flake-like crystals (Water) | 158–159 |
| 160 | 7-[2-Acetyloxy-3-(4-phenylpiperazinyl)propoxy]-3,4-dihydrocarbostyril | Colorless crystals | 130–132 |
| 161 | 5-[2-(3,4,5-Trimethoxybenzoyloxy)-3-(4-phenylpiperazinyl)propoxy]-3,4-dihydrocarbostyril | Colorless crystals (Ethanol) | 125–127 |
| 162 | 7-{3-[3-Methyl-4-(4-chlorophenyl)piperazinyl]propoxy}-3,4-dihydrocarbostyril. dihydrochloride | Colorless crystals (Ethanol) | 235–242 |
| 163 | 4-Phenyl-7-[3-(4-phenylpiperazinyl)propoxy]carbostyril | Colorless needle-like crystals (Methanol) | 198–199 |

EXAMPLE 164

1.8 grams of 1-methyl-5-hydroxy-3,4-dihydrocarbostyril and 1 g of NaH (50% in oil) are mixed with 30 ml of dimethylformamide. Then 2.6 g of 1-chloro-2-hydroxy-3-(4-phenylpiperazinyl)propane are added thereto at room temperature and stirred at 70° to 80° C. for 3 hours. The reaction mixture is poured into water and the organic layer is extracted with chloroform. After removing chloroform by distillation, the thus obtained residue is dissolved in acetone and the pH of the solution is adjusted by adding an acetone solution of oxalic acid. The crystals precipitated are colleced by filtration and recrystallization from methanol-acetone to obtain 2.8 g of 1-methyl-5-[2-hydroxy-3-(4-phenylpiperazinyl)-propoxy]-3,4-dihydrocarbostyril oxalate in the form of colorless crystals with a melting point of 220°-221° C. (decomp.).

EXAMPLES 165-174

Similar to the procedure mentioned in Example 164, there are obtained the following compounds:

| EXAMPLE No. | Compound | Crystal form (Recrystallization solvent) | Melting point (°C.) |
|---|---|---|---|
| 165 | 6,8-Dichloro-5-[2-hydroxy-3-(4-phenyl-piperazinyl)propoxy]-3,4-dihydrocarbostyril. monohydrochloride | Colorless crystals (Water) | 251-253 |
| 166 | 6-Chloro-7-{2-hydroxy-3-[4-(2-methoxyphenyl)-piperazinyl]propoxy}-3,4-dihydrocarbostyril | Colorless crystals (Ethanol) | 183-184 |
| 167 | 1-Benzyl-5-[2-hydroxy-3-(4-phenyl-piperazinyl)propoxy]-3,4-dihydrocarbostyril | Colorless needle-like crystals (Petroleum benzine-ether) | 148-150 |
| 168 | 5-[2-Hydroxy-3-(4-phenylpiperazinyl)-propoxy]-3,4-dihydrocarbostyril. monohydrochloride | Colorless needle-like crystals (Water) | 239-241 |
| 169 | 6-[2-Hydroxy-3-(4-phenylpiperazinyl)-propoxy]-3,4-dihydro-carbostyril.monohydrochloride.½ hydrate | Colorless needle-like crystals (Water) | 223-224 |
| 170 | 7-{2-Hydroxy-3-[4-(4-chlorophenyl)-piperazinyl]propoxy}-3,4-dihydrocarbostyril. monohydrochloride. monohydrate | Colorless needle-like crystals (Isopropanol) | 66-70 |
| 171 | 8-[2-Hydroxy-3-(4-phenylpiperazinyl)-propoxy]-3,4-dihydrocarbostyril.monohydrochloride | Colorless crystals (Methanol-ether) | 263 |
| 172 | 1-Allyl-5-(2-hydroxy-3-[4-(4-methylphenyl)-piperazinyl]propoxy}-3,4-dihydrocarbostyril | Colorless needle-like crystals (Ligroin-benzene) | 123-124 |
| 173 | 6-[2-Hydroxy-3-(4-phenylpiperazinyl)-propoxy]carbostyril .½ hydrate | Colorless crystals (Methanol) | 218-219 |
| 174 | 4-Methyl-7-[2-hydroxy-3-(4-phenyl-piperazinyl)propoxy]-carbostyril. monohydrochloride | Colorless crystals (Ethanol-ether) | 190-191 |

EXAMPLE 175

19 grams of 1-ethyl-5-hydroxy-3,4-carbostyril and 2.2 g of 3-(4-phenypiperazinyl)-1,2-epoxypropane are heated in 30 ml of ethanol for 3 hours under refluxing conditions. The reaction mixture is concentrated under a reduced pressure and the residue is dissolved in 30 ml of acetone solution of oxalic acid. The precipitate thus formed is collected by filtration and recrystallized from ethanol to obtain 3.2 g of 1-ethyl-5-[2-hydroxy-3-(4-phenylpiperazinyl)propoxy]-3,4-dihydrocarbostyril in the form of colorless crystals with a melting point of 201°-203° C.

EXAMPLES 176-186

Similar to procedures mentioned in Example 175, there are obtained the following compounds:

| EXAMPLE No. | Compound | Crystal form (Recrystallization solvent) | Melting point (°C.) |
|---|---|---|---|
| 176 | 5-[2-Hydroxy-3-(4-phenylpiperazinyl)-propoxy]-3,4-dihydro-carbostyril. monohydrochloride | Colorless needle-like crystals (Water) | 239-241 |
| 177 | 6-[2-Hydroxy-3-(4-phenylpiperazinyl)-propoxy]-3,4-dihydro-carbostyril. monohydrochloride. ½ hydrate | Colorless needle-like crystals (Water) | 223-224 |
| 178 | 7-{2-Hydroxy-3-[4-(4-chlorophenyl)-piperazinyl]propoxy}-3,4-dihydrocarbostyril. monohydrochloride. monohydrate | Colorless needle-like crystals (Isopropanol) | 66-70 |
| 179 | 8-[2-Hydroxy-3-(4-phenylpiperazinyl)-propoxy]-3,4-dihydro-carbostyril. monohydrochloride | Colorless crystals (Methanol-ether) | 263 |
| 180 | 6,8-Dichloro-5-[2-hydroxy-3-(4-phenyl-piperazinyl)propoxy]-3,4-dihydrocarbostyril. monohydrochloride | Colorless crystals (Water) | 251-253 |
| 181 | 6-Chloro-7-{2-hydroxy-3-[4-(2-methoxy-phenyl)piperazinyl]-propoxy}-3,4-dihydro-carbostyril | Colorless crystals (Ethanol) | 183-184 |
| 182 | 1-Methyl-5-[2-hydroxy-3-(4-phenylpiperazinyl)propoxy]-3,4-dihydrocarbostyril | Colorless needle-like crystals (Hexane-benzene) | 143-145 |
| 183 | 1-Benzyl-5-[2-hydroxy-3-(4-phenylpiperazinyl)propoxy]-3,4-dihydro-carbostyril | Colorless needle-like crystals (Petroleum benzine-ether) | 148-150 |
| 184 | 1-Allyl-5-{2-hydroxy-3-[4-(4-methylphenyl)-piperazinyl]propoxy}-3,4-dihydrocarbostyril | Colorless needle-like crystals (Ligroin-benzene) | 123-124 |
| 185 | 6-[2-Hydroxy-3-[4-phenylpiperazinyl)-propoxy]carbostyril. ½ hydrate | Colorless crystals (Methanol) | 218-219 |
| 186 | 4-Methyl-7-[2-hydroxy-3-(4-phenylpiperazinyl)propoxy]-carbostyril.mono- | Colorless crystals (Ethanol-ether) | 190-191 |

EXAMPLE 187

(a) Preparation of 8-bromo-5-(2-hydroxy-3-piperazinylpropoxy)-3,4-dihydrocarbostyril 15 grams of piperazine are dissolved in 50 ml of methanol and to this solution are added 70 ml of methanol solution containing 4.4 g of 5-(2,3-epoxypropoxy)-3,4-dihydrocarbostyril dropwise over a period of 30 minutes under reflux conditions by heating. After the addition is finished, the reaction mixture is further heated for 2 hours under reflux conditions, then the reaction mixture is concentrated under a reduced pressure. The residue thus obtained is dissolved in chloroform and unreacted piperazine (which is used in an excessive amount) contained in the reaction mixture is removed by a method of a silica-gel column and effluent is recrystallized from ethanol to obtain 2.4 g of the above-mentioned compound in the form of colorless crystals with a melting point of 195°–196° C.

(b) Preparation of 8-bromo-5-{2-hydroxy-3-[4-(2-methoxyphenyl)-piperazinyl]propoxy}-3,4-dihydrocarbostyril 2.5 grams of 8-bromo-5-(2-hydroxy-3-piperazinylpropoxy)-3,4-dihydrocarbostyril, 2.0 g of o-bromoanisole and 2.0 g of triethylamine are mixed with 30 ml of dimethylformamide. The reaction mixture thus obtained is heated under a stream of argon gas at 120° to 130° C. for 5 hours. The reaction mixture is concentrated under a reduced pressure and to the residue thus obtained is added 30 ml of 5% NaHCO$_3$ aqueous solution, and the organic layer is extracted with chloroform. Chloroform is removed by distillation and to the residue thus obtained are added 3 ml of concentrated hydrochloric acid, then 20 ml of ethanol are added and stirred. The crystals thus precipitated are collected by filtration to obtain 2.1 g of 8-bromo-5-{2-hydroxy-3-[4-(2-methoxyphenyl)piperazinyl]-propoxy}-3,4-dihydrocarbostyril.dihydrochloride in the form of colorless crystals with a melting point of 226°–228° C.

EXAMPLES 188–198

Similar to procedures mentioned in Example 187, there are obtained the following compounds:

| EXAMPLE | Compound | Crystal form (Recrystallization solvent) | Melting point (°C.) |
|---|---|---|---|
| 188 | 5-[2-Hydroxy-3-(4-phenylpiperazinyl)-propoxy]-3,4-dihydrocarbostyril. monohydrochloride | Colorless needle-like crystals (Water) | 239–241 |
| 189 | 6-[2-Hydroxy-3-(4-phenylpiperazinyl)propoxy]-3,4-dihydrocarbostyril. monohydrochloride. ½ hydrate | Colorless needle-like crystals (Water) | 223–224 |
| 190 | 7-{2-Hydroxy-3-[4-(4-chlorophenyl)-piperazinyl]propoxy}-3,4-dihydrocarbostyril. monohydrochloride. monohydrate | Colorless needle-like crystals (Isopropanol) | 66–70 |
| 191 | 8-[2-Hydroxy-3-(4-phenylpiperazinyl)-propoxy]-3,4-dihydrocarbostyril. monohydrochloride | Colorless crystals (Methanol-ether) | 263 |
| 192 | 6,8-Dichloro-5-[2-hydroxy-3-(4-phenylpiperazinyl)-propoxy]-3,4-dihydrocarbostyril. monohydrochloride | Colorless crystals (Water) | 251–253 |
| 193 | 6-Chloro-7-{2-hydroxy-3-[4-(2-methoxyphenyl)-piperazinyl]-propoxy}-3,4-dihydrocarbostyril | Colorless crystals (Ethanol) | 183–184 |
| 194 | 1-Methyl-5-[2-hydroxy-3-(4-phenylpiperazinyl)propoxy]-3,4-dihydrocarbostyril | Colorless needle-like crystals (Hexane-benzene) | 143–145 |
| 195 | 1-Benzyl-5-[2-hydroxy-3-(4-phenylpiperazinyl)propoxy]-3,4-dihydrocarbostyril | Colorless needle-like crystals (Petroleum benzine-ether) | 148–150 |
| 196 | 1-Allyl-5-{2-hydroxy-3-[4-(4-methylphenyl)-piperazinyl]propoxy}-3,4-dihydrocarbostyril | Colorless needle-like crystals (Ligroin-benzene) | 123–124 |
| 197 | 6-[2-Hydroxy-3-(4-phenylpiperazinyl)propoxy]-carbostyril. ½ hydrate | Colorless crystals (Methanol) | 218–219 |
| 198 | 4-Methyl-7-[2-hydroxy-3-(4-phenylpiperazinyl)-propoxy]carbostyril. monohydrochloride | Colorless crystals (Ethanol-ether) | 190–191 |

EXAMPLE 199

(a)-1 3.0 grams of 5-(3-chloropropoxy)-3,4-dihydrocarbostyril and 10 g of piperazine are mixed with 20 ml of hexamethylphosphoryl triamide and heated at 80°–90° C. for 5 hours. The reaction mixture is distilled under a reduced pressure to remove hexamethylphosphoryl triamide and unreacted piperazine. To the residue thus obtained are added 30 ml of 5%-NaHCO$_3$ aqueous solution, followed by extraction with chloroform. The chloroform layer is washed with water and chloroform is removed by distillation. The residue thus obtained is purified by silica-gel chromatography to obtain 1.8 g of 5-(3-piperazinylpropoxy)-3,4-dihydrocarbostyril having a melting point of 192°–195° C.

(a)-2 5 grams of 5-[3-(4-benzylpiperazinyl)propoxy]-3,4-dihydrocarbostyril and 0.8 g of 5%-Pd charcoal are added into 150 ml of isopropanol and catalytically reduced at 60° C. for 5 hours under 3 atm. of hydrogen gas pressure. The catalyst is removed by filtration and the mother liquor thus obtained is concentrated under reduced pressure. The residue is recrystallized from ligroin-benzene to obtain 4.1 g of 5-(3-piperazinylpropoxy)-3,4-dihydrocarbostyril in the form of colorless prism-like crystals having a melting point of 195°–196° C.

(b) 2.9 grams of 5-(piperazinylpropoxy)-3,4-dihydrocarbostyril, 2.5 g of o-bromoethoxybenzene and 1.5 g of sodium carbonate are mixed with 80 ml of n-butanol and refluxed for 20 hours. After cooling, the reaction mixture is concentrated under reduced pressure and the residue is extracted with chloroform. Then chloroform is removed by distillation and the residue thus obtained is recrystallized from ethanol to obtain 2.2 g of 5-{3-[4-(2-ethoxyphenyl)piperazinyl]propoxy}-3,4-dihydrocarbostyril in the form of colorless needle-like crystals having a melting point of 155°–156° C.

EXAMPLES 200–222

Similar to the procedure mentioned in EXAMPLE 199, there are prepared the following compounds:

| EXAMPLE No. | Compound | Crystal form (Recrystallization solvent) | Melting point (°C.) |
|---|---|---|---|
| 200 | 7-[3-(4-Phenylpiperazinyl)propoxy]carbostyril | Yellowish needle-like crystals (Methanol) | 237–238 |
| 201 | 7-{3-[4-(4-Methylphenyl)piperazinyl]propoxy}-3,4-dihydrocarbostyril | Yellowish needle-like crystals (Ethanol) | 149–150 |
| 202 | 6-Bromo-7-[3-(4-phenylpiperazinyl)propoxy]-3,4-dihydrocarbostyril.dihydrochloride | Colorless needle-like crystals (Methanol-ether) | 225–258 |
| 203 | 7-{3-[4-(3-Chlorophenyl)piperazinyl]propoxy}-3,4-dihydrocarbostyril | Colorless needle-like crystals (Ethanol) | 156–158 |
| 204 | 7-{3-[4-(2-Methoxyphenyl)piperazinyl]propoxy}-3,4-dihydrocarbostyril | Colorless powdery crystals (Ethanol) | 134–137 |
| 205 | 7-[4-(4-Phenylpiperazinyl)butoxy]-3,4-dihydrocarbostyril | Colorless needle-like crystals (Isopropanol) | 123–124 |
| 206 | 1-Methyl-7-[3-(4-phenylpiperazinyl)propoxy]-3,4-dihydrocarbostyril.dihydrochloride | Colorless crystals (Ethanol) | 204–207 |
| 207 | 1-Benzyl-7-[3-(4-phenylpiperazinyl)propoxy]-3,4-dihydrocarbostyril | Pale-yellowish needle-like crystals (Ethanol) | 125–127 |
| 208 | 1-Allyl-7-[3-(4-phenylpiperazinyl)propoxy]-3,4-dihydrocarbostyril.dihydrochloride | Colorless crystals (Ethanol) | 189–192 |
| 209 | 1-Propargyl-7-[3-(4-phenylpiperazinyl)propoxy]-3,4-dihydrocarbostyril dihydrochloride | Pale-yellowish needle-like crystals (Methanol) | 215–216 |
| 210 | 4-Methyl-7-[3-(4-phenylpiperazinyl)propoxy]-3,4-dihydrocarbostyril.dihydrochloride.dihydrate | Colorless crystals (Methanol-ether) | 260–265 |
| 211 | 7-{3[4-(3,4,5-Trimethoxyphenyl)piperazinyl]propoxy}-3,4-dihydrocarbostyril.dihydrochloride | Colorless needle-like crystals (Methanol-ethanol) | 225–227 (decomp.) |
| 212 | 7-{3-[4-(3,4-Dimethoxyphenyl)piperazinyl]propoxy}-3,4-dihydrocarbostyril | Brown needle-like crystals (Ethanol) | 146–147 |
| 213 | 7-[3-Methyl-3-(4-phenylpiperazinyl)propoxy]-3,4-dihydrocarbostyril | Colorless flake-like crystals (Methanol-water) | 146–147 |
| 214 | 8-Bromo-6-chloro-7-[3-(4-phenylpiperazinyl)propoxy]-3,4-dihydrocarbostyril.dihydrochloride | Colorless needle-like crystals (Ethanol) | 229–232 (decomp.) |
| 215 | 5-[3-(4-Phenylhomopiperazinyl)propoxy]-3,4-dihydrocarbostyril | Colorless flake-like crystals (Ligroin-benzene) | 122–125 |
| 216 | 4-Methyl-7-[3-(4-phenylpiperazinyl)propoxy]carbostyril | Colorless crystals (Methanol-ether) | 253–254 (decomp.) |
| 217 | 7-{3-[3-Methyl-4-(4-chlorophenyl)piperazinyl]propoxy}-3,4-dihydrocarbostyril.dihydrochloride | Colorless crystals (Ethanol) | 235–242 |
| 218 | 4-Phenyl-7-[3-(4-phenylpiperazinyl)propoxy]carbostyril | Colorless needle-like crystals (Methanol) | 198–199 |
| 219 | 5-[3-(4-Phenylpiperazinyl)propoxy]-3,4-dihydrocarbostyril monohydrochloride | Colorless crystals (Methanol-ether) | 262 (decomp.) |
| 220 | 6-[2-(4-Phenylpiperazinyl)ethoxy]-3,4-dihydrocarbostyril.monohydrochloride.monohydrate | Colorless crystals (Methanol-ether) | 196–198 |
| 221 | 7-[3-(4-Phenylpiperazinyl)propoxy]-3,4-dihydrocarbostyril.dihydrochloride.¼ hydrate | Colorless needle-like crystals (Methanol-ether) | 213–215 |
| 222 | 8-[3-(4-Phenylpiperazinyl)propoxy]-3,4-dihydrocarbostyril | Colorless plate-like crystals (Ethanol) | 112–114 |

EXAMPLE 223

(a) 2.5 grams of 1-methyl-7-[3-(N,N-diethanolamino)propyl]-3,4-dihydrocarbostyril and 4.5 g of N,N-diethyl-1,2,2,-trichlorovinylamide are dispersed in 80 ml of tetrahydrofuran and heated for 3 hours under refluxing conditions. The reaction mixture is concentrated and then purified by silica-gel chromatography to obtain 1.5 g of 1-methyl-7-{3-[bis(β-chloroethyl)amino]-propoxy}-3,4-dihydrocarbostyril in the form of a yellowish oily substance.

(b) 1.5 grams of 1-methyl-7-{3-[bis(β-chloroethyl)amino]propoxy}-3,4-dihydrocarbostyril is dissolved in 30 ml of dimethylformamide and 1.2 g of aniline and 1.5 g of triethylamine are added thereto and warmed to 80°–90° C. for 3 hours. The reaction mixture is concentrated under reduced pressure and to the residue thus obtained are added 50 ml of 5%-NaHCO₃ aqueous solution and 50 ml of chloroform. After shaking the mixture, the chloroform layer is collected. Chloroform is removed by distillation and the residue thus obtained is purified by silica-gel chromatography. The desired compound is converted into the hydrochloride by adding concentrated hydrochloric acid. 0.7 Grams of 1-methyl-7-[3-(4-phenylpiperazinyl)propoxy]-3,4-dihydrocarbostyril.dihydrochloride in the form colorless crystals having melting point of 204°–207° C. are obtained.

EXAMPLES 224–247

Similar to the procedure mentioned in EXAMPLE 223, there are prepared the following compounds:

| EXAMPLE No. | Compound | Crystal form (Recrystallization solvent) | Melting point (°C.) |
|---|---|---|---|
| 224 | 5-[3-(4-Phenyl-piperazinyl)propoxy]-3,4-dihydrocarbostyril.monohydrochloride | Colorless crystals (Methanol-ether) | 262 (decomp.) |
| 225 | 6-[2-(4-Phenyl-piperazinyl)ethoxy]-3,4-dihydrocarbostyril.monohydrochloride.monohydrate | Colorless crystals (Methanol-ether) | 196–198 |
| 226 | 7-[3-(4-Phenyl-piperazinyl)propoxy]-3,4-dihydrocarbostyril.dihydrochloride.¾ hydrate | Colorless needle-like crystals (Methanol-ether) | 213–215 |
| 227 | 8-[3-(4-Phenyl-piperazinyl)propoxy]-3,4-dihydro-carbostyril | Colorless plate-like crystals (Ethanol) | 112–114 |
| 228 | 7-[3-(4-Phenyl-piperazinyl)propoxy]-carbostyril | Yellowish needle-like crystals (Methanol) | 237–238 |
| 229 | 7-{3-[4-(4-Methyl-phenyl)piperazinyl]-propoxy}-3,4-dihydro-carbostyril | Yellowish needle-like crystals (Ethanol) | 149–150 |
| 230 | 6-Bromo-7-[3-(4-phenylpiperazinyl)-propoxy]-3,4-dihydro-carbostyril.dihydrochloride | Colorless needle-like crystals (Methanol-ether) | 255–258 |
| 231 | 7-{3-[4-(3-Chloro-phenyl)piperazinyl]-propoxy}-3,4-dihydro-carbostyril | Colorless needle-like crystals (Ethanol) | 156–158 |
| 232 | 7-{3-[4-(2-Methoxy-phenyl)piperazinyl]-propoxy}-3,4-dihydro-carbostyril | Colorless powdery crystals (Ethanol) | 134–137 |
| 233 | 7-[4-(4-Phenyl-piperazinyl)butoxy]-3,4-dihydrocarbostyril | Colorless needle-like crystals (Isopropanol) | 123–124 |
| 234 | 1-Benzyl-7-[3-(4-phenylpiperazinyl)-propoxy]-3,4-dihydro-carbostyril | Pale yellowish needle-like crystals (Ethanol) | 125–127 |
| 235 | 1-Allyl-7-[3-(4-phenylpiperazinyl)-propoxy]-3,4-dihydro-carbostyril.dihydrochloride | Colorless crystals (Ethanol) | 189–192 |
| 236 | 1-Propargyl-7-[3-(4-phenylpiperazinyl)-propoxy]-3,4-dihydro-carbostyril.dihydrochloride | Pale yellowish needle-like crystals (Methanol) | 215–216 |
| 237 | 4-Methyl-7-[3-(4-phenylpiperazinyl)-propoxy]-3,4-dihydro-carbostyril.dihydrochloride.dihydrate | Colorless crystals (Methanol-ether) | 260–265 |
| 238 | 7-{3-[4-(3,4,5-Tri-methoxyphenyl)-piperazinyl]propoxy}-3,4-dihydrocarbo-styril.dihydrochloride | Colorless needle-like crystals (Methanol-ethanol) | 225–227 |
| 239 | 7-{3-[4-(3,4-Di-methoxyphenyl)-piperazinyl]propoxy}-3,4-dihydrocarbostyril | Brown needle-like crystals (Ethanol) | 146–147 |
| 240 | 7-[2-Methyl-3-(4-phenylpiperazinyl)-propoxy]-3,4-di-hydrocarbostyril | Colorless flake-like crystals (Methanol-water) | 146–147 |
| 241 | 8-Bromo-6-chloro-7-[3-(4-phenyl-piperazinyl)propoxy]-3,4-dihydrocarbo-styril.dihydrochloride | Colorless needle-like crystals (Ethanol) | 229–232 (decomp.) |
| 242 | 5-[3-(4-Phenyl-homopiperazinyl)-propoxy2-3,4-dihydrocarbostyril | Colorless flake-like crystals (Ligroin-benzene) | 122–125 |
| 243 | 4-Methyl-7-[3-(4-phenylpiperazinyl)-propoxy]-carbostyril | Colorless crystals (Methanol-ether) | 253–254 |
| 244 | 5-[3-(4-Cyclohexylpi-perazinyl)propoxy]-3,4-dihydrocarbostyril | Colorless needle-like crystals (Ethanol) | 173–176 |
| 245 | 7-[3-(4-Benzylpipera-zinyl)propoxy]-3,4-dihydrocarbostyril | Colorless needle-like crystals (Ethyl acetate-ether) | 126–127 |
| 246 | 7-{3-[3-Methyl-4-(4-chlorophenyl)pipera-zinyl]propoxy}-3,4-dihydrocarbostyril.dihydrochloride | Colorless crystals (Ethanol) | 235–242 |
| 247 | 4-Phenyl-7-[3-(4-phenylpiperazinyl)-propoxy]carbostyril | Colorless needle-like crystals (Methanol) | 198–199 |

EXAMPLE 248

2.3 grams of 7-[3-(N,N-diethanolamino)-propoxy]-3,4-dihydrocarbostyril are dissolved in 30 ml of pyridine, then 4.0 g of p-tosylchloride are slowly added thereto under ice-cooling and stirred for 2 hours. The reaction mixtue is poured into ice-water and the organic layer is extracted with chloroform. Chloroform is removed by distillation and the residue thus obtained is further distilled under a reduced pressure to remove pyridine remaining in the reaction mixture. The residue thus obtained is dissolved in 50 ml of ethanol and to this solution are added 1.5 g of m-fluoroaniline followed by heating for 10 hours under refluxing conditions. 0.3 g of $Na_2CO_3$ are added thereto, followed by heating for an additional 10 hours under refluxing conditions. The reaction mixture is concentrated under a reduced pressure and the residue thus obtained is shaken with 5% $NaHCO_3$-water and chloroform and the chloroform layer is collected by separation. Chloroform is removed by distillation and the residue is recrystallized from methanol to obtain 1.2 g of 7-{3-[4-(3-fluorophenyl)-piperazinyl]propoxy}-3,4-dihydrocarbostyril in the form of yellowish needle-like crystals having a melting point of 174°–176° C.

EXAMPLES 249–273

Similar to the procedures described in EXAMPLE 248, there are prepared the following compounds:

| EXAMPLE No. | Compound | Crystal form (Recrystallization solvent) | Melting point (°C.) |
|---|---|---|---|
| 249 | 5-[3-(4-Phenylipiperazinyl)propoxy]-3,4-dihydrocarbostyril. monohydrochloride | Colorless crystals (Methanol-ether) | 262 (decomp.) |
| 250 | 6-[2-(4-Phenylpiperazinyl)ethoxy]-3,4-dihydrocarbostyril. monohydrochloride. monohydrate | Colorless crystals (Methanol-ether) | 196–198 |
| 251 | 7-[3-(4-Phenyl-piperazinyl)propoxy]-3,4-dihydrocarbostyril.dihydrochloride.⅔ hydrate | Colorless needle-like crystals (Methanol-ether) | 213–215 |
| 252 | 8-[3-(4-Phenyl-piperazinyl)propoxy]-3,4-dihydrocarbostyril | Colorless plate-like crystals (Ethanol) | 112–114 |
| 253 | 7-[3-(4-Phenylpiperazinyl)propoxy]-carbostyril | Yellowish needle-like crystals (Methanol) | 237–238 |
| 254 | 7-{3-[4-(4-Methyl-phenyl)piperazinyl]-propoxy}-3,4-dihydrocarbostyril | Yellowish needle-like crystals (Ethanol) | 149–150 |
| 255 | 6-Bromo-7-[3-(4-phenyl-piperazinyl)propoxy]-3,4-dihydrocarbostyril. dihydrochloride | Colorless needle-like crystals (Methanol-ether) | 255–258 |
| 256 | 7-{3-[4-(3-Chlorophenyl)piperazinyl]-propoxy}-3,4-dihydrocarbostyril | Colorless needle-like crystals (Ethanol) | 156–158 |
| 257 | 7-{3-[4-(2-Methoxy-phenyl)piperazinyl]-propoxy}-3,4-dihydrocarbostyril | Colorless powdery crystals (Ethanol) | 134–137 |
| 258 | 7-[4-(4-Phenyl-piperazinyl)butoxy]-3,4-dihydrocarbostyril | Colorless needle-like crystals (Isopropanol) | 123–124 |
| 259 | 1-Methyl-7-[3-(4-phenylpiperazinyl)propoxy]-3,4-dihydrocarbostyril. dihydrochloride | Colorless crystals (Ethanol) | 204–207 |
| 260 | 1-Benzyl-7-[3-(4-phenylpiperazinyl)propoxy]-3,4-dihydrocarbostyril | Pale yellowish needle-like crystals (Ethanol) | 125–127 |
| 261 | 1-Allyl-7-[3-(4-phenyl-piperazinyl)propoxy]-3,4-dihydrocarbostyril. dihydrochloride | Colorless crystals (Ethanol) | 189–192 |
| 262 | 1-Propargyl-7-[3-(4-phenylpiperazinyl)propoxy]-3,4-dihydrocarbostyril. dihydrochloride | Pale yellowish needle-like crystals (Methanol) | 215–216 |
| 263 | 4-Methyl-7-[3-(4-phenylpiperazinyl)propoxy]-3,4-dihydrocarbostyril. dihydrochloride. dihydrate | Colorless crystals (Methanol-ether) | 260–265 |
| 264 | 7-{3-[4-(3,4,5-Trimethoxyphenyl)piperazinyl]propoxy}-3,4-dihydrocarbostyril. dihydrochloride | Colorless needle-like crystals (Methanol-ethanol) | 225–227 (decomp.) |
| 265 | 7-{3-[4-(3,4-Dimethoxyphenyl)-piperazinyl]-propoxy}-3,4-dihydrocarbostyril | Brown needle-like crystals (Ethanol) | 146–147 |
| 266 | 7-[2-Methyl-3-(4-phenylpiperazinyl)propoxy]-3,4-dihydrocarbostyril | Colorless flake-like crystals (Methanol-water) | 146–147 |
| 267 | 8-Bromo-6-chloro-7-[3-(4-phenylpiperazinyl)propoxy]-3,4-dihydro-carbostyril. dihydrochloride | Colorless needle-like crystals (Ethanol) | 229–232 (decomp.) |
| 268 | 5-[3-(4-Phenyl-homopiperazinyl)propoxy]-3,4-dihydrocarbostyril | Colorless flake-like crystals (Ligroin-benzene) | 122–125 |
| 269 | 4-Methyl-7-[3-(4-phenylpiperazinyl)propoxy]carbostyril | Colorless crystals (Methanol-ether) | 253–254 (decomp.) |
| 270 | 5-[3-(4-Cyclohexyl-piperazinyl)propoxy]-3,4-dihydrocarbostyril | Colorless needle-like crystals (Ethanol) | 173–176 |
| 271 | 7-[3-(4-Benzyl-piperazinyl)propoxy]-3,4-dihydro-carbostyril | Colorless needle-like crystals (Ethyl acetate-ether) | 126–127 |
| 272 | 7-{3-[3-Methyl-4-(4-chlorophenyl)piperazinyl]propoxy}-3,4-dihydrocarbostyril. dihydrochloride | Colorless crystals (Ethanol) | 235–242 |
| 273 | 4-Phenyl-7-[3-(4-phenylpiperazinyl)propoxy]carbostyril | Colorless needle-like crystals (Methanol) | 198–199 |

EXAMPLE 274

1.6 grams of 5-[2-hydroxy-3-aminopropoxy]-3,4-dihydrocarbostyril, 1.2 g of bis-N,N-(2-bromoethyl)-aniline and 0.56 g of potassium hydroxide are added to 50 ml of butanol and 3 drops of water are further added thereto and heated for 19 hours under refluxing conditions. After the reaction is completed, the solvent is removed by distillaton under a reduced pressure to dryness. The residue thus obtained is dissolved in chloroform and the chloroform solution is washed with water; then the solvent is removed by distillation. The residue thus obtained is purified by a silica-gel chromatography (eluting solvent: chloroform) and the desired compound is then converted into the hydrochloride thereof and recrystallized from water to obtain 5-[2-hydroxy-3-(4-phenylpiperazinyl)-propoxy]-3,4-dihydrocarbostyril in the form of colorless needle-like crystals having a melting point of 239°–241° C.

EXAMPLE 275–284

Similar to the procedure as described in EXAMPLE 274, there are prepared the following compounds:

| EXAMPLE No. | Compound | Crystal form (Recrystallization solvent) | Melting point (°C.) |
|---|---|---|---|
| 275 | 6-[2-Hydroxy-3-(4-phenylpiperazinyl)-propoxy]-3,4-dihydro-carbostyril. monohydrochloride.½ hydrate | Colorless needle-like crystals (Water) | 223–224 |
| 276 | 7-{2-Hydroxy-3-[4- | Colorless | 66–70 |

| EXAMPLE No. | Compound | Crystal form (Recrystallization solvent) | Melting point (°C.) |
|---|---|---|---|
| | (4-chlorophenyl)-piperazinyl]-propoxy}-3,4-dihydro-carbostyril.monohydrochloride.monohydrate | needle-like crystals (Isopropanol) | |
| 277 | 8-[2-Hydroxy-3-(4-phenylpiperazinyl)-propoxy]-3,4-dihydro-carbostyril.monohydrochloride | Colorless crystals (Methanol-ether) | 263 |
| 278 | 6,8-Dichloro-5-[2-hydroxy-3-(4-phenyl-piperazinyl)propoxy]-3,4-dihydrocarbostyril.monohydrochloride | Colorless crystals (water) | 251–253 |
| 279 | 6-Chloro-7-(2-hydroxy-3-[4-(2-methoxypheny)-piperazinyl]propoxy}-3,4-dihydrocarbostyril | Colorless crystals (Ethanol) | 183–184 |
| 280 | 1-Methyl-5-[2-hydroxy-3-(4-phenylpiperazi-nyl)propoxy}-3,4-dihydrocarbostyril | Colorless needle-like crystals (Hexane-benzen) | 143–145 |
| 281 | 1-Benzyl-5-[2-hydroxy-3-(4-phenyl-piperazinyl)propoxy]-3,4-dihydrocarbostyril | Colorless needle-like crystals (Petroleum benzine-ether) | 148–150 |
| 282 | 1-Allyl-5-{2-hydroxy-3-[4-(4-methylphenyl)pipera-zinyl]propoxy}-3,4-dihydrocarbostyril | Colorless needle-like crystals (Ligroin-benzene) | 123–124 |
| 283 | 6-[2-Hydroxy-3-(4-phenylpiperazinyl)-propoxy]carbostyril.½ haydrate | Colorless crystals (Methanol) | 218–219 |
| 284 | 4-Methyl-7-[2-hydroxy-3-(4-phenyl-piperazinyl)propoxy]-carbostyril.monohydrochloride | Colorless crystals (Ethanol-ether) | 190–191 |

EXAMPLE 285

1.5 grams of 7-[3-aminopropoxy]-3,4-dihydrocarbostyril, 1.2 g of bis-N,N-(2-bromoethyl)aniline, and 0.56 g of potassium hydroxide are added to 50 ml of butanol. 3 drops of water are added thereto followed by heating for 20 hours under refluxing conditions. After the reaction is completed, the solvent is removed by distillation under a reduced pressure. The residue thus obtained is dissolved in chloroform and the chloroform extract is washed with water; then chloroform is removed by distillation. The residue thus obtained is purified by a silica-gel column chromatography (eluting solvent: chloroform) and the desired compound is converted into it hydrochloride and recrystallized from methanolether to obtain 7-[3-(4-phenylpiperazinyl)propoxy]-3,4-dihydrocarbostyril.dihydrochloride.¾ hydrate in the form of colorless needle-like crystals having a melting point of 213°–215° C.

EXAMPLES 286–309

Similar to the procedure described in EXAMPLE 285, there are prepared the following compounds:

| EXAMPLE No. | Compound | Crystal form (Recrystallization solvent) | Melting point (°C.) |
|---|---|---|---|
| 286 | 5-[3-(4-Phenyl-piperazinyl)propoxy]-3,4-dihydrocarbostyril.monohydrochloride | Colorless crystals (Methanol-ether) | 262 (decomp.) |
| 287 | 6-[2-(4-Phenyl-piperazinyl)ethoxy]-3,4-dihydrocarbo-styril.monohydro-chloride.monohydrate | Colorless crystals (Methanol-ether) | 196–198 |
| 288 | 8-[3-(4-Phenyl-piperazinyl)propoxy]-3,4-dihydrocarbostyril | Colorless plate-like crystals (Ethanol) | 112–114 |
| 289 | 7-[3-(4-Phenyl-piperazinyl)propoxy]-carbostyril | Yellowish needle-like crystals (Methanol) | 237–238 |
| 290 | 7-{3-[4-(4-Methyl-phenyl)piperazinyl]-propoxy}-3,4-dihydrocarbostyril | Yellowish needle-like crystals (Ethanol) | 149–150 |
| 291 | 6-Bromo-7-[3-(4-phenylpiperazinyl)-propoxy]-3,4-di-hydrocarbostyril.dihydrochloride | Colorless needle-like crystals (Methanol-ether) | 255–258 |
| 292 | 7-{3-[4-(3-Chloro-phenyl)piperazinyl]-propoxy}-3,4-di-hydrocarbostyril | Colorless needle-like crystals (Ethanol) | 156–158 |
| 293 | 7-{3-[4-(2-Methoxy-phenyl)piperazinyl]-propoxy}-3,4-dihydrocarbostyril | Colorless powdery crystals (Ethanol) | 134–137 |
| 294 | 7-[4-(4-Phenyl-piperazinyl)butoxy]-3,4-dihydrocarbostyril | Colorless needle-like crystals (Isopropanol) | 123–124 |
| 295 | 1-Methyl-7-[3-(4-phenylpiperazinyl)-propoxy]-3,4-dihydro-carbostyril.dihydrochloride | Colorless crystals (Ethanol) | 204–207 |
| 296 | 1-Benzyl-7-[3-(4-phenylpiperazinyl)-propoxy]-3,4-di-hydrocarbostyril | Pale yellowish needle-like crystals (Ethanol) | 125–127 |
| 297 | 1-Ally-7-[3-(4-phenylpiperazinyl)-propoxy]-3,4-di-hydrocarbostyril.dihydrochloride | Colorless crystals (Ethanol) | 189–192 |
| 298 | 1-Propargyl-7-[3-(4-phenylpiperazinyl)-propoxy]-3,4-dihydro-carbostyril.dihydrochloride | Pale yellowish needle-like crystals (Methanol) | 215–216 |
| 299 | 4-Methyl-7-[3-(4-phenylpiperazinyl)-propoxy]-3,4-dihydrocarbostyril.dihydrochloride.dihydrate | Colorless crystals (Methanol-ether) | 260–265 |
| 300 | 7-{3-[4-(3,4,5-Tri-methoxyphenyl)-piperazinyl]propoxy}-3,4-dihydrocarbostyril.dihydrochloride | Colorless needle-like crystals (Methanol-ethanol) | 225–227 (decomp.) |
| 301 | 7-{3-[4-(3,4-Di-methoxyphenyl)-piperazinyl]propoxy}-3,4-dihydrocarbo-styril | Brown needle-like crystals (Ethanol) | 146–147 |
| 302 | 7-[2-Methyl-3-(4-phenylpiperazinyl)-propoxy]-3,4-dihydrocarbostyril | Colorless flake-like crystals (Methanol-water) | 146–147 |
| 303 | 8-Bromo-6-chloro- | Colorless | 229–232 |

| EXAMPLE No. | Compound | Crystal form (Recrystallization solvent) | Melting point (°C.) |
|---|---|---|---|
|  | 7-[3-(4-phenyl-piperazinyl)propoxy]-3,4-dihydrocarbo-styril.dihydrochloride | needle-like crystals (Ethanol) | (decomp.) |
| 304 | 5-[3-(4-Phenyl-homopiperazinyl)-propoxy]-3,4-di-hydrocarbostyril | Colorless flake-like crystals (Ligroin-benzene) | 122–125 |
| 305 | 4-Methyl-7-[3-(4-phenylpiperazinyl)-propoxy]carbostyril | Colorless crystals (Methanol-ether) | 253–254 (decomp.) |
| 306 | 5-[3-(4-Cyclohexylpipe-razinyl)propoxy]-3,4-dihydro-carbostyril | Colorless needle-like crystals (Ethanol) | 173–176 |
| 307 | 7-[3-(4-Benzyl-piperazinyl)propoxy]-3,4-dihydro-carbostyril | Colorless needle-like crystals (Ethyl acetate-ether) | 126–127 |
| 308 | 7-{3-[3-Methyl-4-(4-chlorophenyl)-piperazinyl]-propoxy}-3,4-dihydro-carbostyril. dihydrochloride | Colorless crystals (Ethanol) | 235–242 |
| 309 | 4-Phenyl-7-[3-(4-phenylpiperazinyl)-propoxy]carbostyril | Colorless needle-like crystals (Methanol) | 198–199 |

What is claimed is:

1. A carbostyril derivative represented by the formula,

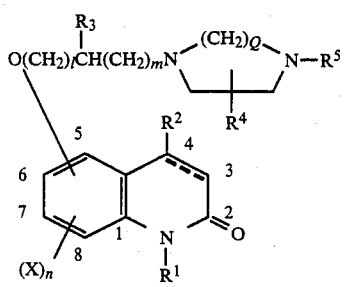

wherein R¹ is a hydrogen atom, an alkyl group having 1 to 6 carbon atoms, an alkenyl group having 2 to 4 carbon atoms, an alkynyl group having 2 to 4 carbon atoms or a phenyl alkyl group having an alkylene group having 1 to 4 carbon atoms; R² is a hydrogen atom, an alkyl group having 1 to 4 carbon atoms or a phenyl group; R³ is a hydrogen atom, a hydroxy group, an alkyl group having 1 to 4 carbon atoms, an alkanoyloxy group having 1 to 4 carbon atoms or a 3,4,5-trimethoxybenzoyloxy group; R⁴ is a hydrogen atom or an alkyl group having 1 to 4 carbon atoms; R⁵ is a cycloalkyl group having 3 to 8 carbon atoms, a phenyl group which may be substituted by 1 to 3 identical or different groups selected from the group consisting of a halogen atom, an alkyl group having 1 to 4 carbon atoms, an alkoxy group having 1 to 4 carbon atoms, a substituted alkyl group having 1 to 4 carbon atoms, having one hydroxy group, phenyl group or alkanoyloxy group having 1 to 4 carbon atoms as the substituent, an alkanoyl group having 1 to 4 carbon atoms and a benzoyl group; X is a halogen atom; n is 0 or an integer of 1 or 2; Q is an integer of 3; l and m are respectively 0 or an integer of 1 to 6, but the sum of l and m should not exceed 6; the carbon-carbon bond at the 3- and 4-positions in the carbostyril skeleton is a single or double bond; the substituted position of the side chain of

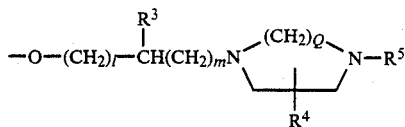

is any one of the 4-, 5-, 6-, 7- or 8-positions, or a pharmaceutically acceptable acid addition salt thereof, with the proviso that when said side chain is substituted at the 4-position and said carbon-carbon bond at the 3- or 4-positions is a double bond, then R² does not exist.

2. A carbostyril derivative or a pharmaceutically acceptable acid addition salt thereof according to claim 1, wherein R³ is a hydrogen atom or an alkyl group having 1 to 4 carbon atoms.

3. A carbostyril derivative or a pharmaceutically acceptable acid addition salt thereof according to claim 1, wherein R³ is a hydroxy group, an alkanoyloxy group having 1 to 4 carbon atoms or a 3,4,5-trimethoxybenzoyloxy group.

4. A carbostyril derivative or a pharmaceutically acceptable acid addition salt thereof according to claim 2, wherein R⁵ is a phenyl group which may be substituted by 1 to 3 identical or different groups selected from the group consisting of a halogen atom, an alkyl group having 1 to 4 carbon atoms and an alkoxy group having 1 to 4 carbon atoms.

5. A carbostyril derivative or a pharmaceutically acceptable acid addition salt thereof according to claim 2, wherein R⁵ is a substituted alkyl group having 1 to 4 carbon atoms, having one phenyl group as the substituent.

6. A carbostyril derivative or a pharmaceutically acceptable acid addition salt thereof according to claim 2, wherein R⁵ is selected from the group consisting of a cycloalkyl group having 3 to 8 carbon atoms; a substituted alkyl group having 1 to 4 carbon atoms having one hydroxy group or alkanoyloxy group having 1 to 4 carbon atoms as the substituent; an alkanoyl group having 1 to 4 carbon atoms and a benzoyl group.

7. A carbostyril derivative or a pharmaceutically acceptable acid addition salt thereof according to claim 3, wherein R⁵ is a phenyl group which may be substituted by 1 to 3 identical or different groups selected from the group consisting of a halogen atom, an alkyl group having 1 to 4 carbon atoms and an alkoxy group having 1 to 4 carbon atoms.

8. A carbostyril derivative or a pharmaceutically acceptable acid addition salt thereof according to claim 3, wherein R⁵ is selected from the group consisting of a cycloalkyl group having 3 to 8 carbon atoms; a substituted alkyl group having 1 to 4 carbon atoms having one hydroxy group, phenyl group or alkanoyloxy group having 1 to 4 carbon atoms as the substituent; an alkanoyl group having 1 to 4 carbon atoms and a benzoyl group.

9. A carbostyril derivative or a pharmaceutically acceptable acid addition salt thereof according to claim 4, wherenin the substituted position of the side chain represented by the formula,

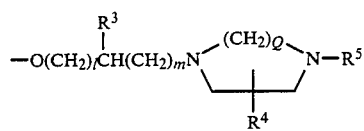

is the 5- or 7-position in the carbostyril skeleton.

10. A carbostyril derivative or a pharmaceutically acceptable acid addition salt thereof according to claim 4, wherein the substituted position of the side chain represented by the formula,

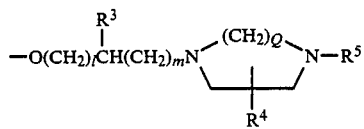

is the 4-, 6- or 8-position in the carbostyril skeleton.

11. A carbostyril derivative or a pharmaceutically acceptable acid addition salt thereof according to claim 9, wherein the substituted position of the side chain represented by the formula,

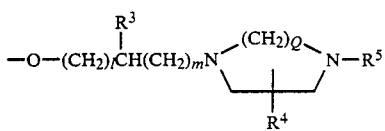

is the 5-position in the carbostyril skeleton.

12. A carbostyril derivative or a pharmaceutically acceptable acid addition salt thereof according to claim 9, wherein the substituted position of the side chain represented by the formula,

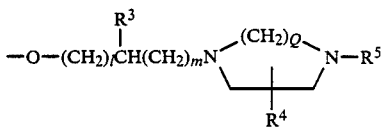

is the 7-position in the carbostyril skeleton.

13. 5-[3-(4-Phenylhomopiperazinyl)propoxy]-3,4-dihydrocarbostyril.

14. A pharmaceutical composition useful as an antihistaminic agent, comprising an antihistaminically effective amount of a carbostyril derivative or a pharmaceutically acceptable salt thereof according to claim 1 and a pharamaceutically acceptable carrier.

15. A pharmaceutical composition useful as a central nervous controlling agent, comprising an amount of carbostyril derivative or a pharmaceutically acceptable acid salt thereof according to claim 1 sufficient to affect the central nervous system and a pharmaceutically acceptable carrier.

* * * * *

UNITED STATES PATENT AND TRADEMARK OFFICE
CERTIFICATE OF CORRECTION

PATENT NO. : 4,824,840

DATED : April 25, 1989

INVENTOR(S) : KAZUO BANNO et al.

It is certified that error appears in the above-identified patent and that said Letters Patent is hereby corrected as shown below:

In The Abstract:

In the fifth line above the second formula, change "1" to --$\ell$--;

In the fourth line above the second formula, change "0 to" to --0 or-- and change "1", second occurrence, to --$\ell$--.

In The Claims:

In claim 1, column 70, line 1 thereof, delete "1" and replace it with --$\ell$--;

Column 70, line 2, immediately after "sum of" delete "1" and replace it with --$\ell$--.

Signed and Sealed this

Thirteenth Day of February, 1990

Attest:

JEFFREY M. SAMUELS

Attesting Officer     Acting Commissioner of Patents and Trademarks